United States Patent
Roberts et al.

(10) Patent No.: US 7,129,052 B1
(45) Date of Patent: Oct. 31, 2006

(54) PEPTIDES AND THEIR UTILITY IN MODULATION OF BEHAVIOR OF CELLS EXPRESSING α3β1 INTEGRINS

(75) Inventors: David D. Roberts, Bethesda, MD (US); Henry C. Krutzsch, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 630 days.

(21) Appl. No.: 10/030,735

(22) PCT Filed: Jul. 12, 2000

(86) PCT No.: PCT/US00/18986

§ 371 (c)(1), (2), (4) Date: Jan. 9, 2002

(87) PCT Pub. No.: WO01/05812

PCT Pub. Date: Jan. 25, 2001

(51) Int. Cl.
*G01N 33/53* (2006.01)
*A61K 38/04* (2006.01)

(52) U.S. Cl. .................. 435/7.1; 530/327; 530/328; 530/329; 530/330

(58) Field of Classification Search .............. 530/327, 530/326, 329, 330; 435/7.1
See application file for complete search history.

(56) References Cited

U.S. PATENT DOCUMENTS 5,696,229 A * 12/1997 Laurie et al.
5,770,563 A * 6/1998 Roberts et al.
5,789,184 A * 8/1998 Fowlkes et al.
6,020,312 A * 2/2000 Edwards

FOREIGN PATENT DOCUMENTS

| JP | 10257896 | * | 9/1998 |
| WO | WO 90 03983 | * | 4/1990 |
| WO | WO 92/09628 | * | 6/1992 |
| WO | WO 98/42737 | * | 10/1998 |

OTHER PUBLICATIONS

Prater et al. The properdin-like type I repeats of human thrombospondin contain a cell attachment site.J Cell Biol. 112(5):1031-40, 1991.*
Li et al. An all-D amino acid peptide model of alpha1(IV)531-543 from type IV collagen binds the alpha3beta 1 integrin and mediates tumor cell adhesion, spreading, and motility. Biochemistry. 36(49):15404-15410, 1997.*
Nomizu et al. Identification of cell binding sequences in mouse laminin gamma1 chain by systematic peptide screening.J Biol Chem. 272(51):32198-205, 1997.*
Chandrasekaran et al. Pro-adhesive and chemotactic activities of thrombospondin-1 for breast carcinoma cells are mediated b alpha3beta1 integrin and regulated by insulin-like growth factor-1 and CD98, J Biol Chem. 274(16):11408-16, 1999.*
krtzsch et al. Identification of an alpha(3)beta(1) integrin recognition sequence in thrombospondin-1. J Biol Chem. 274(34):24080-6, 1999.*
Khan et al Role of laminin in matrix induction of macrophage urokinase-type plasminogen activator and 92-kDa metalloproteinase expression. J Biol Chem. 272(13):8270-5., 1997.*

* cited by examiner

*Primary Examiner*—Maher M. Haddad
(74) *Attorney, Agent, or Firm*—Townsend and Townsend and Crew LLP

(57) ABSTRACT

The present invention relates to a peptide comprising the sequence $R_1-X_1-X_2-X_3-X_4-R_2$, wherein $X_1$ is selected from the group consisting of N, Q, D and S; $X_2$ is selected from the group consisting of V, I and L; $X_3$ is selected from the group consisting of R and K; and $X_4$ is selected from the group consisting of V, I, L and F; $R_1$ is a hydrogen or a peptide of 1 to 6 amino acids, and acyl or an aryl group; and $R_2$ is a peptide of 1 to 3 amino acids, a hydroxide or an amide. The invention also relates to partial or full retro-inverso peptides comprising the above sequences. The invention also relates to peptide-substrate combination comprising a substrate suitable for cell growth and the peptide of the invention, and to a vascular graft and an artificial blood vessel comprising the peptide-substrate combination. The invention also relates to a pharmaceutical composition and a peptide conjugate comprising the peptide of the invention. The invention also relates to a method of inhibiting adhesion of a cell expressing α3β1 integrin to an cellular matrix, inhibiting α3β1-integrin-mediated cell motility, inhibiting α3β1-integrin mediated cell proliferation, promoting α3β1-integrin mediated cell proliferation and inhibiting angiogenesis utilizing the peptides of the invention.

23 Claims, 20 Drawing Sheets

TSP1 | Fibronectin
 
FIG. 12A        FIG. 12B
TSP1 | Fibronectin
 
FIG. 12C        FIG. 12D
TSP1 | Fibronectin
 
FIG. 12E        FIG. 12F bar = 100 μm

SEQUENCE LISTING

```
<160> NUMBER OF SEQ ID NOS: 56

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:
      thrombospondin-1 (TSP-1) peptide 246

<400> SEQUENCE: 1

Lys Arg Phe Lys Gln Asp Gly Gly Trp Ser His Trp Ser Pro Trp Ser
 1               5                  10                  15

Ser

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:
      thrombospondin-1 (TSP-1) peptide 500

<400> SEQUENCE: 2

Asn Gly Val Gln Tyr Arg Asn Cys
 1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:
      thrombospondin-1 (TSP-1) peptide Mal II

<400> SEQUENCE: 3

Ser Pro Trp Ser Ser Cys Ser Val Thr Cys Gly Asp Gly Val Ile Thr
 1               5                  10                  15

Arg Ile Arg

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:
      thrombospondin-1 (TSP-1) peptide 4N1K

<400> SEQUENCE: 4

Lys Arg Phe Tyr Val Val Met Trp Lys Lys
 1               5                  10

<210> SEQ ID NO 5
<211> LENGTH: 19
<212> TYPE: PRT
<213> ORGANISM: Artificial Sequence
<220> FEATURE:
```

-continued

<223> OTHER INFORMATION: Description of Artificial Sequence:
      thrombospondin-1 (TSP-1) peptide HepI

<400> SEQUENCE: 5

Glu Leu Thr Gly Ala Ala Arg Lys Gly Ser Gly Arg Arg Leu Val Lys
1               5                   10                  15

Gly Pro Asp

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:
      thrombospondin-1 (TSP-1) peptide 678

<400> SEQUENCE: 6

Phe Gln Gly Val Leu Gln Asn Val Arg Phe Val Phe
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence:
      thrombospondin-1 (TSP-1) peptide 701

<400> SEQUENCE: 7

Thr Pro Gly Gln Val Arg Thr Leu Trp His Asp Pro
1               5                   10

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence:
      murine laminin-1 A chain peptide GD6

<400> SEQUENCE: 8

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:integrin
      antagonist peptide

<400> SEQUENCE: 9

Gly Arg Gly Asp Ser Pro
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:control
      peptide 686

<400> SEQUENCE: 10

```
Phe Gln Gly Val Leu Gln Ala Val Arg Phe Val Phe
 1               5                  10
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:control
      peptide 690

<400> SEQUENCE: 11

```
Phe Gln Gly Val Leu Gln Asn Val Ala Phe Val Phe
 1               5                  10
```

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence:laminin
      peptide 679

<400> SEQUENCE: 12

```
Phe Arg Gly Cys Val Arg Asn Leu Arg Leu Ser Arg
 1               5                  10
```

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:R1 peptide

<400> SEQUENCE: 13

```
Phe Gln Gly Val Leu Gln
 1               5
```

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:R1 peptide

<400> SEQUENCE: 14

```
Phe Ala Gly Val Leu Gln
 1               5
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:R1 peptide

<400> SEQUENCE: 15

```
Phe Gln Gly Val Ala Gln
 1               5
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:R1 peptide -continued

```
<400> SEQUENCE: 16

Phe Gln Gly Val Leu Ala
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:R1 peptide

<400> SEQUENCE: 17

Phe Gln Gly Val Leu Asn
 1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:peptide 719
      analog of thrombospondin-1 (TSP-1)

<400> SEQUENCE: 18

Phe Gln Gly Val Leu Gln Asn Leu Arg Phe Val Phe
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:peptide 718
      analog of thrombospondin-1 (TSP-1)

<400> SEQUENCE: 19

Phe Gln Gly Val Leu Gln Asp Val Arg Phe Val Phe
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:peptide 717
      analog of thrombospondin-1 (TSP-1)

<400> SEQUENCE: 20

Phe Gln Gly Val Leu Gln Gln Val Arg Phe Val Phe
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:peptide 705
      analog of thrombospondin-1 (TSP-1)

<400> SEQUENCE: 21

Phe Gln Gly Val Leu Gln Ser Val Arg Phe Val Phe
 1               5                  10

<210> SEQ ID NO 22
<211> LENGTH: 9
<212> TYPE: PRT
<213> ORGANISM: Artificial Sequence
```

```
<220> FEATURE:
<223> OTHER INFORMATION: Description of Artificial Sequence:peptide 704
      analog of thrombospondin-1 (TSP-1)
<220> FEATURE:
<221> NAME/KEY: MOD_RES
<222> LOCATION: (1)
<223> OTHER INFORMATION: Xaa = N-acetyl glutamine

<400> SEQUENCE: 22

Xaa Gly Val Leu Gln Asn Val Arg Phe
 1               5

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence:peptide 702
      analog of thrombospondin-1 (TSP-1)

<400> SEQUENCE: 23

Phe Gln Gly Val Leu Gln Asn Val Lys Phe Val Phe
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence:peptide 698
      analog of thrombospondin-1 (TSP-1)

<400> SEQUENCE: 24

Phe Gln Gly Val Leu Asn Asn Val Arg Phe Val Phe
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:peptide 697
      analog of thrombospondin-1 (TSP-1)

<400> SEQUENCE: 25

Ala Gln Gly Val Leu Gln Asn Val Arg Phe Val Phe
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:peptide 696
      analog of thrombospondin-1 (TSP-1)

<400> SEQUENCE: 26

Phe Ala Gly Val Leu Gln Asn Val Arg Phe Val Phe
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:peptide 695
      analog of thrombospondin-1 (TSP-1)

<400> SEQUENCE: 27
```

Phe Gln Gly Val Ala Gln Asn Val Arg Phe Val Phe
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:peptide 693
      analog of thrombospondin-1 (TSP-1)

<400> SEQUENCE: 28

Phe Gln Gly Val Leu Gln Asn Val Arg Phe Val Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:peptide 687
      analog of thrombospondin-1 (TSP-1)

<400> SEQUENCE: 29

Phe Gln Gly Val Leu Ala Asn Val Arg Phe Val Phe
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence:peptide 689
      analog of thrombospondin-1 (TSP-1)

<400> SEQUENCE: 30

Phe Gln Gly Val Leu Gln Asn Val Arg Phe Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence:peptide 685
      analog of thrombospondin-1 (TSP-1)

<400> SEQUENCE: 31

Gln Gly Val Leu Gln Asn Val Arg Phe Val Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:peptide 682
      analog of thrombospondin-1 (TSP-1)

<400> SEQUENCE: 32

Phe Gln Gly Val Leu Gln Asn Val Arg Phe
1               5                   10

<210> SEQ ID NO 33
<211> LENGTH: 11
<212> TYPE: PRT
<213> ORGANISM: Artificial Sequence -continued

```
<220> FEATURE:
<223> OTHER INFORMATION: Description of Artificial Sequence:
      thrombospondin-1 (TSP-1) peptide (598-608)

<400> SEQUENCE: 33

Asn Cys Leu Pro Cys Pro Pro Arg Phe Thr Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:
      thrombospondin-1 (TSP-1) peptide (188-199)

<400> SEQUENCE: 34

Asp Asn Phe Gln Gly Val Leu Gln Asn Val Arg Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence:
      thrombospondin-1 (TSP-1) peptide (392-405)

<400> SEQUENCE: 35

Asn Asn Arg Cys Glu Gly Ser Ser Val Gln Thr Arg Thr Cys
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence:
      thrombospondin-1 (TSP-1) peptide (1059-1077)

<400> SEQUENCE: 36

Arg Asn Ala Leu Trp His Thr Gly Asn Thr Pro Gly Gln Val Arg Thr
1               5                   10                  15

Leu Trp His

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence:type IV
      collagen peptide 674

<400> SEQUENCE: 37

Gly Glu Phe Tyr Phe Asp Leu Arg Leu Lys Gly Asp Lys Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:peptide 681
      analog of thrombospondin-1 (TSP-1)
<220> FEATURE:
<221> NAME/KEY: MOD_RES
<222> LOCATION: (1)
<223> OTHER INFORMATION: Xaa = N-acetyl leucine
```

```
<220> FEATURE:
<221> NAME/KEY: MOD_RES
<222> LOCATION: (6)
<223> OTHER INFORMATION: Xaa = phenylalanine carboxamide

<400> SEQUENCE: 38

Xaa Leu Gln Asn Val Arg Phe Xaa
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:peptide 683
      analog of thrombospondin-1 (TSP-1)

<400> SEQUENCE: 39

Gln Gly Val Leu Gln Asn Val Arg
  1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence:peptide 684
      analog of thrombospondin-1 (TSP-1)

<400> SEQUENCE: 40

Leu Gln Asn Val Arg Phe Val Phe
  1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:peptide 688
      analog of thrombospondin-1 (TSP-1)

<400> SEQUENCE: 41

Val Leu Gln Asn Val Arg Phe Val Phe
  1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:peptide 691
      analog of thrombospondin-1 (TSP-1)

<400> SEQUENCE: 42

Phe Gln Gly Val Leu Gln Asn Ala Arg Phe Val Phe
  1               5                  10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:peptide 692
      analog of thrombospondin-1 (TSP-1)

<400> SEQUENCE: 43

Phe Gln Gly Val Leu Gln Asn Val Arg Ala Val Phe
  1               5                  10
```

```
<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:peptide 694
      analog of thrombospondin-1 (TSP-1)

<400> SEQUENCE: 44

Phe Gln Gly Val Leu Gln Asn Val His Phe Val Phe
  1               5                  10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:peptide 703
      analog of thrombospondin-1 (TSP-1)

<400> SEQUENCE: 45

Phe Gln Gly Val Leu Gln Asn Val Gln Phe Val Phe
  1               5                  10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence:peptide 716
      analog of thrombospondin-1 (TSP-1)
<220> FEATURE:
<221> NAME/KEY: MOD_RES
<222> LOCATION: (1)
<223> OTHER INFORMATION: Xaa = carboxamidomethyl-thioproprionyl
      phenylalanine

<400> SEQUENCE: 46

Xaa Gln Gly Val Leu Gln Asn Val Arg Phe Val Phe
  1               5                  10

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence:peptide 701
      context surrounding Arg

<400> SEQUENCE: 47

Gln Val Arg Thr
  1

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence:entactin
      region related sequence

<400> SEQUENCE: 48

Phe Ser Gly Ile Asp Glu His Gly His Leu Thr Ile
  1               5                  10

<210> SEQ ID NO 49
<211> LENGTH: 4
```

```
<212> TYPE: PRT
<213> ORGANISM: Artificial Sequence
<220> FEATURE:
<223> OTHER INFORMATION: Description of Artificial Sequence:entactin
      domain NXR sequence

<400> SEQUENCE: 49

Asn Asn Arg His
 1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence:entactin
      domain NXR sequence

<400> SEQUENCE: 50

Asn Gly Arg Gln
 1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:consensus
      sequence

<400> SEQUENCE: 51

Asn Val Arg Phe
 1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence:
      X-1-X-2-X-3-X-4 peptide

<400> SEQUENCE: 52

Ser Val Arg Phe
 1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:
      X-1-X-2-X-3-X-4 peptide

<400> SEQUENCE: 53

Gln Val Arg Phe
 1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence:
      X-1-X-2-X-3-X-4 peptide

<400> SEQUENCE: 54

Asp Val Arg Phe
```

```
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence:
      X-1-X-2-X-3-X-4 peptide

<400> SEQUENCE: 55

Asn Leu Arg Phe
  1

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence:
      thrombospondin-1 (TSP-1) peptide

<400> SEQUENCE: 56

Leu Gln Asn Val Arg Phe
  1               5
```

PEPTIDES AND THEIR UTILITY IN MODULATION OF BEHAVIOR OF CELLS EXPRESSING α3β1 INTEGRINS

FIELD OF THE INVENTION

The present invention relates generally to peptides that bind to or are recognized by α3β1 integrins, to pharmaceutical compositions containing such peptides and to methods for inhibiting various functions of cells that express α3β1 integrins utilizing these peptides. The cell functions include cell adhesion to extracellular matrix, cell motility and proliferation, and angiogenesis. The present invention also relates to methods for promoting proliferation of enodothelial cells and to methods for treating angiogenesis-mediated diseases utilizing these peptides.

BACKGROUND OF THE INVENTION

Integrins are transmembrane α, β-heterodimer receptors expressed on a wide variety of cells which are involved in extracellular matrix interactions. There are eight known β (beta) subunits and 14 known α (alpha) subunits that associate with each other to give at least twenty receptors with different ligand specificities. The ligands for several of the integrins are adhesive extracellular matrix (ECM) proteins such as fibronectin, vitronectin, collagens and laminin.

It is becoming increasingly clear that the ECM influences gene expression, and changes in expression of genes encoding matrix proteins alter the composition of the ECM. Thus information flows in both directions between cells and their surrounding matrix. Integrins appear to transmit messages from the exterior to the interior of the cell, inducing various kinds of changes in gene expression. In this capacity, the integrins control cell growth, motility, differentiation, and survival. Defects in the regulation of these processes result in many medically important diseases, such as inheritable developmental disorders, defective wound repair, hematological disorders, cardiovascular diseases, immunological disorders, neurodegenerative diseases, and cancer initiation, invasion, and metastasis.

α3β1 integrins have been reported to recognize several extracellular matrix ligands, including some laminins, type IV collagen, fibronectin, and thrombospondin-1. A need exists for methods that affect the interaction of α3β1 integrin-expressing cells with their environment. The present invention fulfills this and other needs.

SUMMARY OF THE INVENTION

In one aspect, the present invention relates to a peptide comprising the sequence $R_1$-$X_1$-$X_2$-$X_3$-$X_4$-$R_2$, wherein $X_1$ is selected from the group consisting of N, Q, D and S; $X_2$ is selected from the group consisting of V, I and L; $X_3$ is selected from the group consisting of R and K; and $X_4$ is selected from the group consisting of V, I, L and F; $R_1$ is a hydrogen or a peptide of 1 to 6 amino acids, an acyl or an aryl group; and $R_2$ is a peptide of 1 to 3 amino acids, a hydroxide or an amide. In one embodiment, the peptides are partial or full retro-inverso peptides comprising the above sequences In another aspect, the present invention relates to peptide-substrate combination comprising a substrate suitable for cell growth and the peptide of the invention, and to a vascular graft and an artificial blood vessel comprising the peptide-substrate combination.

The invention also relates to a pharmaceutical composition comprising the peptide of the invention and a pharmaceutically acceptable carrier.

In another aspect, the invention relates to a peptide conjugate comprising the peptide of the invention and a water-soluble polymer.

The invention also relates to a method of inhibiting adhesion of a cell expressing α3β1 integrin to an extracellular matrix comprising contacting the cell with the peptide of the present invention.

The invention also relates to a method of inhibiting α3β1-integrin-mediated cell motility, comprising contacting the cell with the peptide of the present invention.

The invention also relates to a method of inhibiting α3β1-integrin mediated cell proliferation comprising contacting the cell with the peptide of the present invention and to a method of promoting α3β1-integrin mediated cell proliferation comprising contacting the cell with the peptide-substrate combination of the present invention.

The invention also relates to a method of treating an angiogenesis-mediated disease in an animal comprising administering to the animal an effective amount of the peptide of the present invention.

BRIEF DESCRIPTION OF THE DRAWINGS

FIG. 12 displays electron micrographs showing that spreading on TSP1 induced by loss of cell—cell contact is inhibited by the α3β1 integrin-binding peptide from TSP1. BAE cells from confluent (a, b) or sparse (c–f) cultures were incubated for 60 min on substrates coated with 40 μg/ml TSP1 (a, c, e) or 20 μg/ml fibronectin (b, d, f). Inhibition by 30 μM TSP1 peptide 678 is presented in (e–f). Cells were fixed with 1% glutaraldehyde and stained using Diff-quik. Bar in panel a=25 μm.

(striped bars), or type I collagen (open bars). The percent spread cells was determined at 60 min.

Figure 14A:
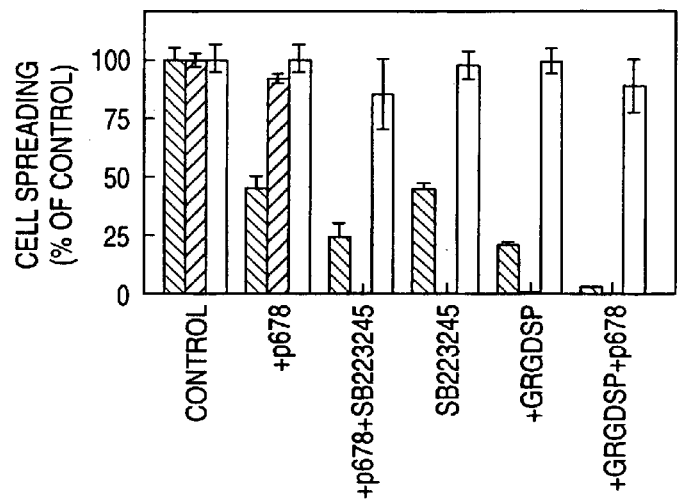
Figure 14B:
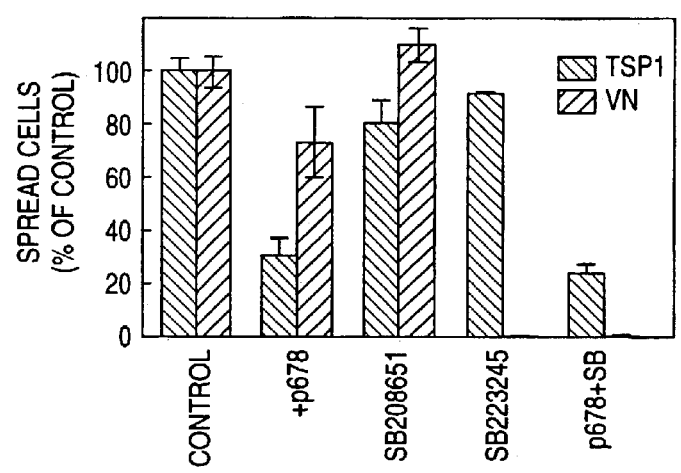
Figure 14C:
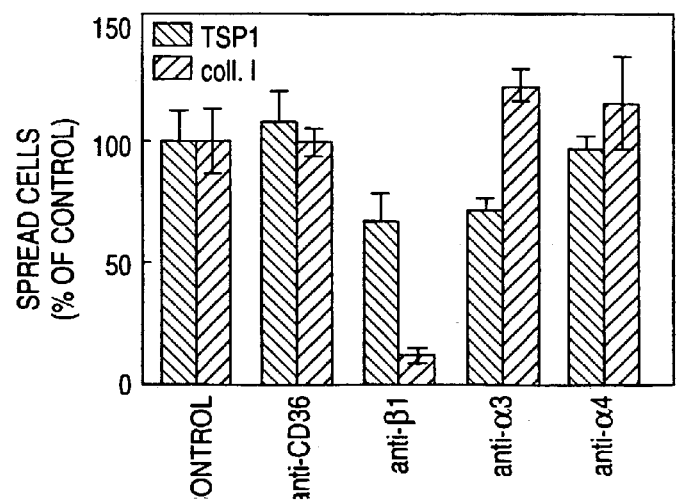

FIGS. 14A, 14B and 14C display α3β1 and αvβ3 integrin-mediated spreading of endothelial cells on thrombospondin-1. Panel A: BAE cell adhesion to TSP1 (solid bars), vitronectin (striped bars), or plasma fibronectin (open bars) was measured in the presence of 30 μM TSP1 peptide 678, 1 μM of the αvβ3 integrin antagonist SB223245, 300 μM of the integrin antagonist peptide GRGDSP (SEQ ID NO:9), or the indicated combinations. Results are expressed as percent of the response for untreated cells, mean±S.D., n=3. Panel B: HUVEC spreading on substrates coated with TSP1 (solid bars) or vitronectin (striped bars) was determined in the presence of 20 μM peptide 678, 1 μM αIIbβ3 antagonist SB208651, 1 μM αvβ3 antagonist SB223245, or 20 μM peptide 678 plus 1 μM SB223245. Spreading is presented as a percent of the respective controls without inhibitors (31 cells/mm2 for TSP1 and 10 cells/mm2 for vitronectin). Panel C: Inhibition of HDME cell spreading on TSP1 (solid bars) or type I collagen (striped bars) was determined in the presence of the indicated function blocking antibodies at 5 μg/ml: anti-CD36 (OKM5), anti-integrin β1 (mAb13), anti-integrin α3 (P1B5), and anti-integrin α4 (P4C2).

FIG. 15 displays fluorescence micrographs showing integrin and CD98 localization in endothelial cells spreading on TSP1 or TSP1 peptide 678 substrates. Cells attached on TSP1 (panels a–d) or TSP1 peptide 678 (panels e, f) were stained using antibodies to α3β1 integrin (a, e), CD98 (b, f), phosphotyrosine (c), or vinculin (d). Bar in panel a=25 μm.

Figure 16:
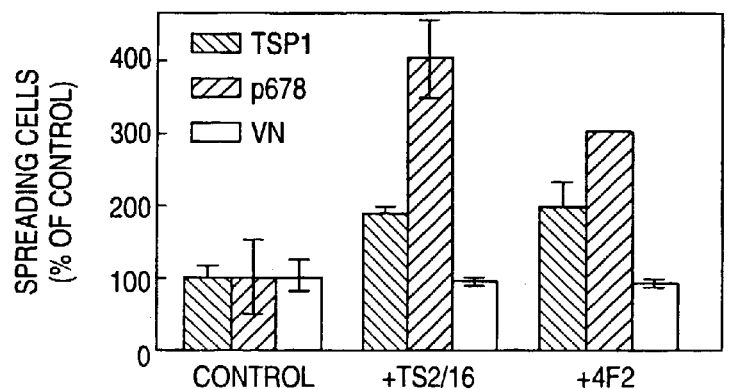

FIG. 16 displays histograms showing that β1 Integrin- and CD98-activating antibodies induce HUVEC spreading on TSP1 and TSP1 peptide 678. Untreated HUVEC (control) or cells in the presence of 5 μg/ml of the β1 integrin activating antibody (TS2/16) or CD98 antibody (4F2) were incubated on substrates coated with 40 μg/ml TSP1 (solid bars), 5 μM peptide 678 (striped bars), or 5 μg/ml vitronectin (open bars). Cell spreading is expressed as a percent of the response for untreated cells, mean±S.D., n=3.

FIGS. 17A, 17B, 17C and 17D display the adhesion characteristics of various small cell lung carcinoma lines to TSP1 at various concentrations of TSP1. Bacteriological polystyrene was coated with the indicated concentrations of TSP1(●), laminin (○), or fibronectin (▲). Small cell lung carcinoma lines H128 (Panel A), OH-1 (Panel C), OH-1 variant (Panel D), and melanoma cell line A2058 (Panel B) were allowed to attach on each substrate for 60 minutes. Adherent cells were counted microscopically and are presented as the mean of triplicate determinations.

Figure 18A:
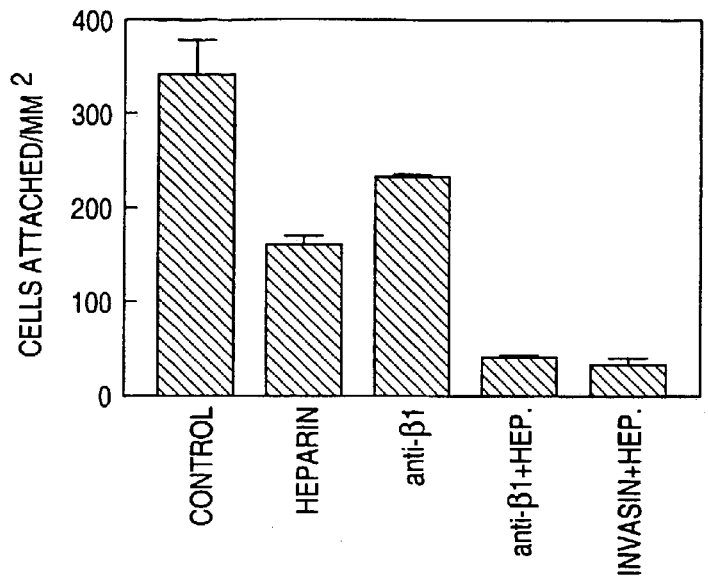
Figure 18B:
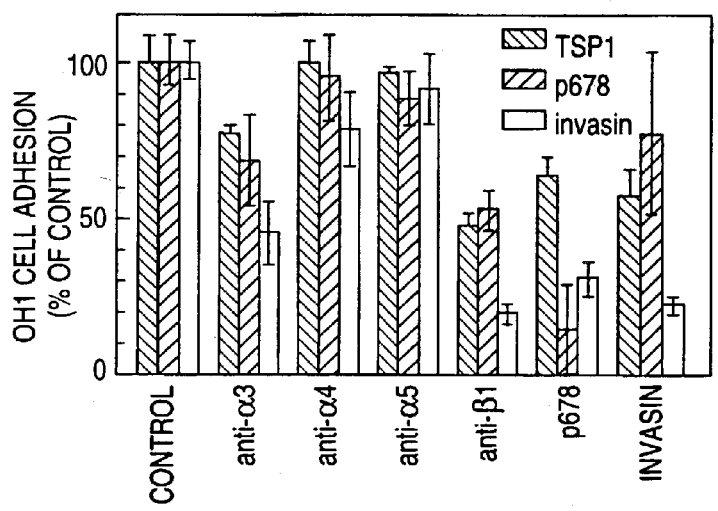
Figure 18C:
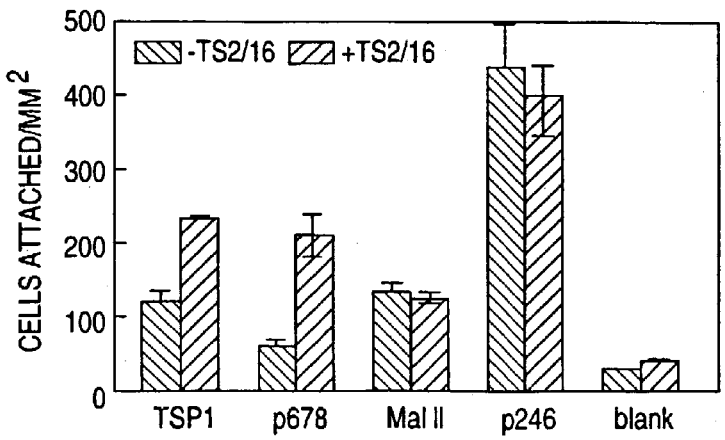

FIGS. 18A, 18B and 18C display graphs of OH-1 SCLC cell adhesion on TSP1 in the presence and absence of various integrin function-blocking antibodies, integrin ligands and peptides. Panel A: OH-1 cell adhesion on a substrate coated with 40 μg/ml TSP1, mean±SD, n=3, was determined in RPMI containing 1 mg/ml BSA (control) or the same medium containing 25 μg/ml heparin, 5 μg/ml mAb13 (anti-β1), mAb13 and heparin (anti-β1+hep.), or 40 μg/ml MBP-invasin fusion protein and 25 μg/ml heparin (invasin+hep.). Panel B: OH1 SCLC cell adhesion on substrates coated using 40 μg/ml TSP1 (solid bars), 5 μM TSP1 peptide 678 (striped bars), or 0.2 μg/ml MBP-invasin (open bars) was determined in the presence of 5 μg/ml antibody P1B5 (anti-α3), 5 μg/ml antibody P4C2 (anti-α4), 5 μg/ml antibody P1D6 (anti-α5), 5 μg/ml antibody mAb13 (anti-β1), 20 μM TSP1 peptide 678 (p678), or 40 μg/ml MBP-invasin (invasin). Results are presented as a percent of control adhesion determined for each protein without inhibitors, mean±SD, n=3. Panel C: OH-1 cell adhesion to substrates coated with 25 μg/ml TSP1 or 5 μM of TSP1 peptides that bind to α3β1 integrin (p678), CD36 (Mal II), or heparin (p246) was determined in the absence (solid bars) or presence of the β1 integrin-activating antibody TS2/16 at 5 μg/ml (striped bars). Results are presented as mean±SD, n=3.

Figure 19A:
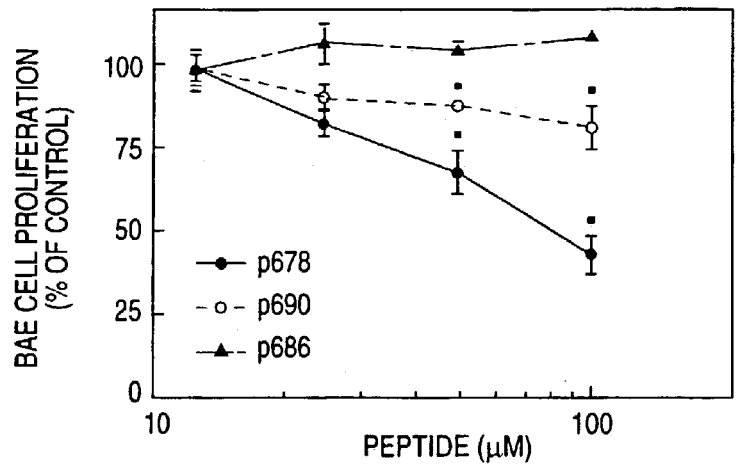
Figure 19B:
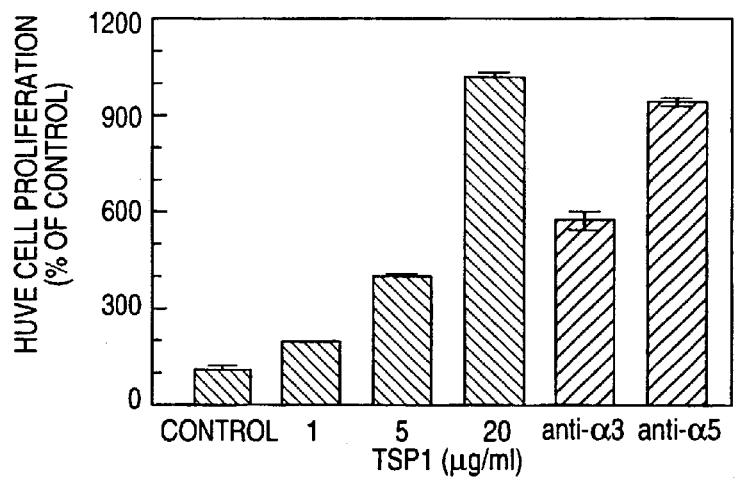
Figure 19C:
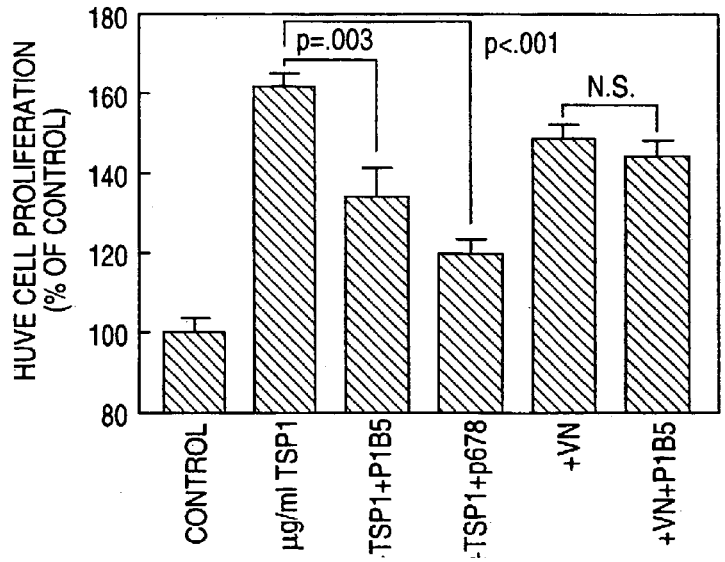
Figure 19D:
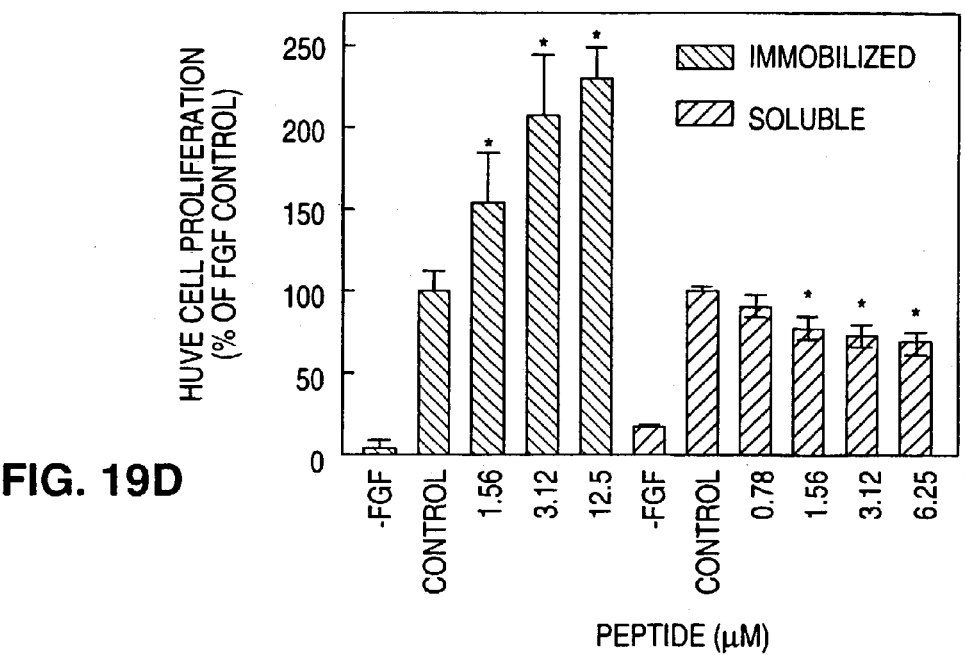
Figure 19E:
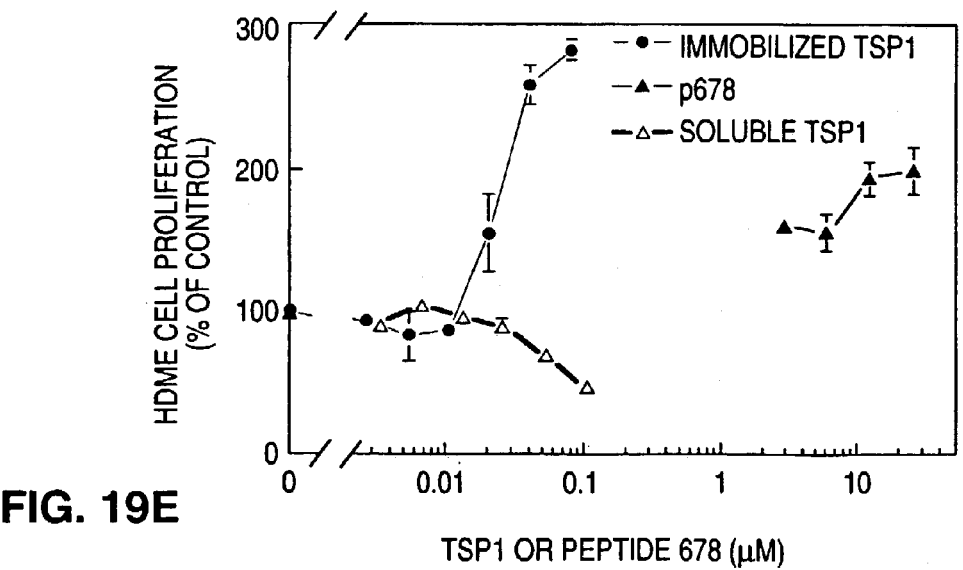

FIGS. 19A, 19B, 19C, 19D and 19E display the modulation of endothelial cell proliferation by an α3β1 integrin binding peptide from TSP1. FIG. 19A: Proliferation of BAE cells was assayed in the presence of the indicated concentrations of TSP1 peptide 678 (FQGVLQNVRFVF (SEQ ID NO:6), ) or the control peptides 686 (FQGVLQ$\overline{A}$VRFVF (SEQ ID NO:10), ▲), and 690 (FQGVLQNV$\overline{A}$FVF (SEQ ID NO:11), O). Briefly, 100 μl of a 5×10⁴ cell/ml suspension of BAE cells were seeded in triplicate into 96 well tissue culture plate in DMEM medium containing 1% FCS, 10 ng/ml of FGF2 and peptides at 1–40 μM concentrations. Cells were incubated for 72 h, and proliferation was measured using the Celltiter tetrazolium assay (Promega). FIG. 19B: HUVE cell proliferation was measured at 72 h for cells plated on wells coated with the indicated concentrations of TSP1(solid bars) or 1 μg/ml of antibody P1B5 (anti-α3β1 integrin) (striped bar) or P1D6 (anti-α5β1 integrin) in medium 199 containing 5% FCS (striped bar). FIG. 19C: α3β1 integrin mediates the proliferative response to immobilized TSP1. HUVE cells were plated in medium 199 containing 20% FCS on wells coated using 5 μg/ml TSP1, 5 μg/ml vitronectin, or BSA (control) alone or in the presence of 5 μg/ml of the α3β1 blocking antibody P1B5 or 20 μM of TSP1 peptide 678. Proliferation was determined at 72 h, and is presented as a percent of the control, mean±S.D., n=3 for experimental points and n=6 for control. FIG. 19D: HUVE cell proliferation was determined in the presence of the indicated concentrations of TSP1 peptide 678 immobilized on the substrate (solid bars) or added in solution (striped bars). Conditions that significantly differed from their respective controls based on a 2-tailed t test with p<0.05 are marked with an "*". FIG. 19E: HDME cell proliferation in MCDB growth medium with 5% FCS was determined in the presence of 10 ng/ml FGF2 and the indicated concentrations of TSP1 added in the medium (Δ) or immobilized on the substrate (●) or in wells coated with the indicated concentrations of peptide 678 (▲). Results are presented as mean±S.D. and are normalized to controls without TSP1 or peptide.

FIGS. 20A, 20B, 20C, 20D and 20E display the inhibition of .SCLC cell proliferation by TSP1. Panel A: Soluble TSP1 and α3β1 integrin ligands inhibit SCLC cell proliferation. OH1 cells (1×10⁴/well) were incubated for 72 h in growth medium containing the indicated concentrations of TSP1 (●), MBP-invasin (○), TSP1 peptide 678 (▲), or the inactive peptide analog 686 (Δ). Net proliferation was determined by the CellTiter assay (Promega) and is presented as mean±SD, n=3. Panel B: OH1 cells grow as monolayers on a TSP1 substrate. OH1 cells were allowed to attach on a dish coated with 50 μg/ml of TSP1 sterilized by filtration through a 0.22 μm Millex GV filter and grown in RPMI medium containing 4% Ultroser HY for 5 days. The cells were fixed and photographed using Nomarski optics. Bar=100 μm. Panel C: Growth on immobilized TSP1 inhibits proliferation in the presence of EGF. OH1 cell proliferation in growth medium (●) or medium supplemented with 10 ng/ml EGF (○) was determined after 72 h on substrates coated with the indicated concentrations of TSP1, mean±SD, n=3. Panel D: Cell proliferation was determined in the presence of the indicated concentrations of EGF in wells coated with BSA (●) or with 50 μg/ml TSP1 (○). Panel E: α3β1 Integrin ligands cooperate with EGF to inhibit OH1 cell proliferation. Proliferation in the absence (solid bars) or presence of 10 ng/ml EGF (striped bars) was determined in wells coated with 10 μM of the TSP1 peptides 678 (α3β1 ligand), 246 (heparin-binding peptide), 7N3 (CD47 ligand), or 1 μg/ml MBP-invasin (α3β1 ligand). Net proliferation is presented as a percent of the -EGF control (mean±SD, n=3 for treated groups and n=6 for control groups).

Figure 21:
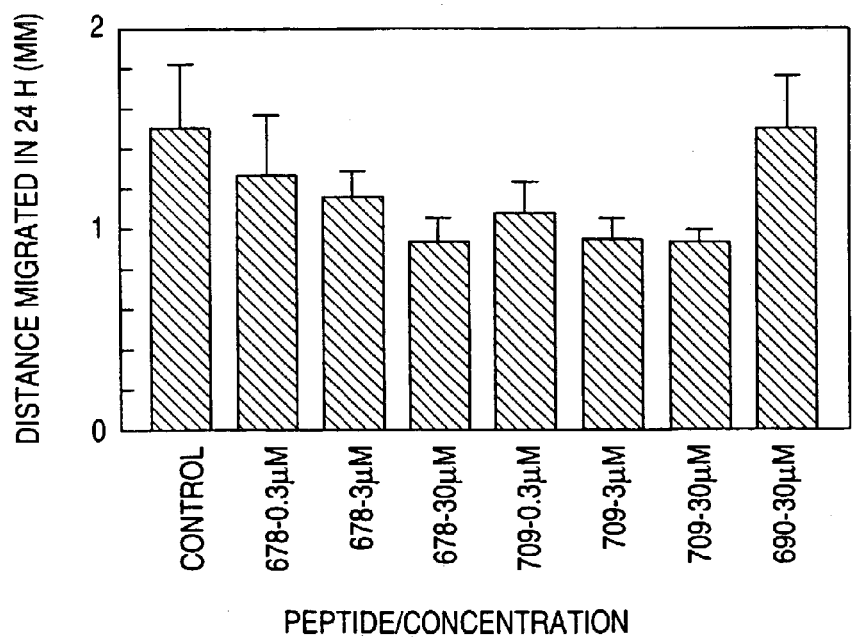

FIG. 21 is a histogram exhibiting inhibition of wound healing of BAE cells by TSP1 peptides 678, 690 and 709. BAE cells were seeded at a density of 2×10$^5$ cells/well of 6 well tissue culture plates in complete growth medium supplemented with 10% FBS. After the cells formed a confluent cobblestone, cells were arrested using 10 μg/ml 5-fluorouracil for 48 h. Scrape wounds of 2 mm width were made in the wells, and the cells were further incubated with medium containing 10% FBS, 10 μg/ml 5 fluorouracil and peptides 678, 709, or 690. Measurements of the distance between the wound margins were taken at 0 and 24 h, and the net migration is expressed as mean±SEM for triplicates.

DESCRIPTION OF THE SPECIFIC EMBODIMENTS

I. Introduction

Integrins are receptors that are expressed on a wide variety of cells which are involved in extracellular matrix interactions. Expression of the α3 β1 integrin is essential for normal development in the kidney and lungs (Kreidberg et al., 1996). Targeted mutation of the murine α3 integrin gene resulted in abnormal branching morphogenesis of kidney capillary loops and lung bronchi. Based on antibody inhibition, this integrin may also be important for branching morphogenesis in mammary epithelia (Stahl et al., 1997). In addition to its essential roles in normal development, the α3β1 integrin may play important roles in disease processes such as cancer. Loss of integrin α3 subunit expression is a negative prognostic factor in lung adenocarcinoma (Adachi et al., 1998). Conversely, over-expression of α3β1 integrin in a human rhabdomyosarcoma line suppressed tumor formation in mouse xenografts (Weitzman et al., 1996).

The α3β1 integrin has been reported to recognize several extracellular matrix ligands, including some laminins, type IV collagen, fibronectin, thrombospondin-1, and entactin/nidogen (DeFreitas et al., 1995; Elices et al., 1991; Hemler et al., 1990; Wu et al., 1995). Although short peptide recognition motifs have been identified in ligands for some integrins (reviewed in Yamada, K. M., 1991), previous attempts to define recognition sequences for binding of matrix ligands to the α3β1 integrin have produced conflicting results. High affinity binding of recombinant soluble α3β1 could be detected only to laminin-5 (Eble et al., 1998), so binding to other matrix ligands may be of relatively low affinity. Under specific conditions, this integrin can recognize the common integrin binding sequence Arg-Gly-Asp (RGD) in fibronectin (Elices et al., 1991). However, recombinant entactin with the RGD sequence deleted (Gresham et al., 1996) and synthetic peptides from laminin-1 and type IV collagen that lack the RGD motif (Gehlsen et al., 1992; Miles et al., 1995) also bound specifically to the α3β1 integrin. Laminin peptide GD6 and the type IV collagen peptide affinity purified α3β1 integrin from cell extracts when immobilized on agarose beads (Gehlsen et al., 1992; Miles et al., 1995), but the active peptides from these two proteins share no apparent sequence homology. These data combined with the evidence that RGD-dependent and RGD-independent adhesion are differentially regulated in α3β1 integrin (Elices et al., 1991) has lead to the proposal that the α3β1 integrin uses distinct mechanisms to interact with each of its ligands and that no conserved binding motif may exist (Elices et al, 1991).

It has recently been found that α3β1 is the major human thrombospondin-1 (TSP1)-binding integrin on several human breast carcinoma cell lines (Chandrasekaran et al., 1999) Thrombospondins are a family of matrix proteins that have diverse effects on cell adhesion, motility, proliferation and survival (reviewed in Bornstein, P., 1992, 1995; Roberts, 1996). Screening of recombinant fusion proteins and synthetic peptides covering 85% of the TSP1 sequence, however, failed to identify an α3β1 integrin binding site. This interaction has been further examined and is disclosed herein. This invention relates to the identification of a peptide sequence that supports α3β1-dependent adhesion and chemotaxis and that is a potent inhibitor of adhesion to TSP1. This invention also relates to the modulation of angiogenesis and the behavior of endothelial cells using the peptides and peptide analogs disclosed herein. Thrombospondin-1 (TSP1) also plays a role in the process of angiogenesis. It is known that angiogenesis under normal and pathological conditions is regulated by both positive and negative signals received from soluble growth factors and components of the extracellular matrix (reviewed in: Folkman, J. 1995; Hanahan et al., 1996; Polyerini, P. J., 1995). TSP1 and thrombospondin-2 (TSP2), have been reported to inhibit angiogenesis (Good, 1990; Volpert, 1995). TSP1 inhibits growth, sprouting, and motility responses of endothelial cells in vitro (Good et al., 1990; Taraboletti et al, 1990; Iruela Arispe et al., 1991; Canfield et al., 1995) and, under defined conditions, induces programmed cell death in endothelial cells (Guo et al., 1997). TSP1 inhibits angiogenesis in vivo in the rat corneal pocket and chick chorioallantoic membrane (CAM) angiogenesis assays (Good et al., 1990; Iruela-Arispe et al., 1999). The ability of TSP1 over-expression to suppress tumor growth and neovascularization in several tumor xenograft models provides further evidence for an anti-angiogenic activity of TSP1 (Weinstat-Saslow et al., 1994; Dameron et al., 1994; Hsu et al., 1996; Sheibani et al., 1995). Circulating TSP1 may also inhibit neovascularization of micrometastases in some cancers (Morelli et al., 1998; Volpert et al., 1998). A few studies, however, reported that TSP1 also has pro-angiogenic activities under specific conditions (BenEzra et al., 1993; Nicosia et al., 1994). Observations of elevated TSP1 expression during endothelial injury and wound repair are also difficult to rationalize with a purely anti-angiogenic activity for TSP1 (Vischer, 1988; Munjal, 1990; Reed, 1995). These apparently contradictory reports have led to confusion in the past about the true role of TSP1 as an angiogenesis regulator.

A need exists for compounds that bind to α3, 1 integrins that exert their respective therapeutic and prophylactic functions in treating or alleviating various conditions and diseases and that modulate various functions of cells that express α3β1 integrins. The present invention fulfills this and other needs.

II. Definitions

The following definitions are provided to assist the reader in the practice of the invention.

Peptide

As used herein, the term "peptide" is used in its broadest sense to refer to conventional peptides (i.e. short polypeptides containing L or D-amino acids), as well as peptide equivalents, peptide analogs and peptidomimetics that retain the desired functional activity. Peptide equivalents can differ from conventional peptides by the replacement of one or more amino acids with related organic acids (such as PABA), amino acids or the like, or the substitution or modification of side chains or functional groups.

The terms "peptide equivalents", "peptide analogs", "peptide mimetics", and "peptidomimetics" are used interchangeably unless specified otherwise. Peptide analogs are commonly used in the pharmaceutical industry as non-peptide drugs with properties analogous to those of the template peptides. (Fauchere, J. (1986) Adv. Drug Res. 15: 29; Veber and Freidinger (1985) TINS p. 392; and Evans et al. (1987) J. Med. Chem 30: 1229). Peptide analogs are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH═CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R. G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—). Portions or all of the peptide backbone can also be replaced by conformationally constrained cyclic alkyl or aryl substituents to restrict mobility of the functional amino acid sidechains specified herein as described in the following references:

1. Bondinell et al. Design of a potent and orally active nonpeptide platelet fibrinogen receptor (GPIIb/IIIa) antagonist. Bioorg Med Chem 2:897 (1994).

2. Keenan et al. Discovery of potent nonpeptide vitronectin receptor (alpha v beta 3) antagonists. J Med Chem 40:2289 (1997).

3. Samanen et al. Potent, selective, orally active 3-oxo-1,4-benzodiazepine GPIIb/IIIa integrin antagonists. J Med Chem 39:4867 (1996).

The peptides of this invention may be produced by recognized methods, such as recombinant and synthetic methods that are well known in the art. Recombinant techniques are generally described in Sambrook, et al., Molecular Cloning: A Laboratory Manual, (2nd ed.) Vols. 1–3, Cold Spring Harbor Laboratory, (1989). Techniques for the synthesis of peptides are well known and include those described in Merrifield, J. Amer. Chem. Soc. 85:2149–2456 (1963), Atherton, et al., Solid Phase Peptide Synthesis: A Practical Approach, IRL Press (1989), and Merrifield, Science 232:341–347 (1986).

As used herein, unless otherwise indicated, the term "peptide" and "polypeptide" are used interchangably.

Retro-Inverso Peptide

As used herein, the term "retro-inverso peptide" refers to a peptide that typically comprises the same amino acid sequence as a peptide having L-amino acids, but whose sequence is comprised partially or entirely of D-amino acids, thus having a reversed stereochemistry from a peptide which is synthesized using L-amino acids. By constructing a peptide using the D-amino acids in inverse order (i.e. the sequences are denoted from left to right, from C-terminal to N-terminal amino acid as opposed to from N-terminal to C-terminal as written or denoted in the case of L-amino acids; see infra), one obtains a retro-inverso peptide that restores the same stereochemistry for the side chains as the parent L-amino acid peptide. Use of retro-inverso peptide sequences minimizes enzymatic degradation and, therefore, extends biological half-life of the peptide moiety. Also, these sequences may favorably alter potential immunogenic properties of the analogous conjugates prepared from normal L-amino acid sequences. The retro-inverso sequences (as free peptides or conjugates) are particularly useful in those applications that require or prefer orally active agents (due to resistance to enzymolysis).

For the purposes of the present invention, retro-inverso peptides are denoted by "ri", and are written, from left to right, from the C-terminal to the N-terminal amino acid, e.g. the opposite of typical L-peptide notation. In one embodiment, the retro-inverso peptide of the present invention incorporates all D isomer amino acids. When the retro-inverso peptide incorporate all D isomer amino acids, it is termed a "D-reverse peptide".

The peptides may be prepared under sterile, aseptic, or antiseptic conditions. Alternatively, compositions containing the peptides may be sterilized by, e.g., using heat, filtration, irradiation, or other means. The peptides may be stored or used in solid form (e.g., as a powder, such as a lyophilized powder) or may be prepared as a sterile solution (e.g., a sterile aqueous solution, such as a buffered aqueous solution).

Substantially Pure

The terms "substantially pure," or "isolated" when used to describe peptides, refers to a peptide separated from proteins or other contaminants with which they are naturally associated or with which they are associated during synthesis. In one embodiment, a peptide or polypeptide makes up at least 50% of the total polypeptide content of the composition containing the peptide, and in one embodiment, at least 60%, in one embodiment, at least 75%, in one embodiment at least 90%, and in one embodiment, at least 95% of the total polypeptide content.

Amino Acid

As used herein, the term "amino acid" and any reference to a specific amino acid is meant to include naturally occurring amino acids as well as non-naturally occurring amino acids such as amino acid analogs. Thus, unless otherwise specifically indicated, the term "amino acid" refers to naturally occurring (D) or (L) amino acids, chemically modified amino acids, including amino acid analogs such as penicillamine (3-mercaptol-D-valine), naturally occurring amino acids such as norleucine and chemically synthesized compounds that have properties known in the art to be characteristic of an amino acid.

Amino acid residues in peptides are abbreviated as follows: Phenylalanine is Phe or F; Leucine is Leu or L;

Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Peptides that are acetylated at the amino terminal group will possess the prefix "ac". Similarly, carboxamide amino acids at the C-terminal will possess the suffix "am". Thus, peptides which have the sequences described herein, but which have been modified to include an amino-terminal N-acyl or aryl group and/or a carboxyl-terminal amide or alkyl amide group are also included in the present invention. The abbreviation "tp" denotes thiopropionyl.

The choice of including an (L)- or a (D)-amino acid into a peptide of the present invention depends, in part, on the desired characteristics of the peptide. For example, the incorporation of one or more (D)-amino acids can confer increasing stability on the peptide in vitro or in vivo. In some cases it is desirable to design a peptide which retains activity for a short period of time, for example, when designing a peptide to administer to a subject. In these cases, the incorporation of one or more (L)-amino acids in the peptide can allow endogenous peptidases in the subject to digest the peptide in vivo, thereby limiting the subject's exposure to an active peptide.

Effective Amount

The term "effective amount" as used in relation to pharmaceutical compositions, typically refers to the amount of the active ingredient, e.g. the peptides of the invention, which are required to achieve the desired goal. For example, in therapeutic applications, an effective amount will be the amount required to be administered to a patient to result in treatment of the particular disorder for which treatment is sought. The term "treatment of a disorder" denotes the reduction or elimination of symptoms of a particular disorder. Effective amounts will typically vary depending upon the nature of the disorder, the peptides used, the mode of administration, and the size and health of the patient.

In one embodiment, the effective amount of the peptides of the invention ranges from 1 µg to 1 g of peptide for a 70 kg patient, and in one embodiment, from 1 µg to 10 mg. In one embodiment, the concentration of peptide (or peptide analog) administered ranges from 0.1 µM to 10 mM, and in one embodiment, from 5 µM to 1 mM, in one embodiment, from 5 µM to 100 µM, and in one embodiment from 5 µM to 40 µM.

III. Peptides of the Invention

The present invention generally provides peptides, comprising the sequence

$R_1\text{-}X_1\text{-}X_2\text{-}X_3\text{-}X_4\text{-}R_2$ (I)

wherein X1 is selected from the group consisting of N, Q, D and S; X2 is selected from the group consisting of V, I and L; X3 is selected from the group consisting of R and K; and X4 is selected from the group consisting of V, I, L and F;

$R_1$ is a hydrogen or a peptide of 1 to 6 amino acids, an acyl or an aryl group; and R2 is a peptide of 1 to 3 amino acids, a hydroxide or an amide. In one embodiment of the invention, peptides having the sequence FQGVLQNVRFVF (SEQ ID NO:6) or FRGCVRNLRLSR (SEQ ID NO:12) are specifically excluded. In one embodiment, the peptides contain from 4 to 12 amino acids, i.e., has a length of 4 to 12 amino acid residues. In one embodiment, the peptides comprise additional residues, e.g., typically up to a length of 15, 20, 25, or 40 residues that includes the core sequence (I).

In one embodiment of the present invention, $R_1$ is a peptide comprising the sequence selected from the group consisting of FQGVLQ (SEQ ID NO:13), FAGVLQ (SEQ ID NO:14), FQGVAQ (SEQ ID NO:15), FQGVLA (SEQ ID NO:16), and FQGVLN (SEQ ID NO:17).

In one embodiment, the peptide of the present invention comprises at least one sequence selected from the group consisting of FQGVLQNLRFVF (SEQ ID NO:18), FQGVLQDVRFVF (SEQ ID NO:19), FQGVLQQVRFVF (SEQ ID NO:20), FQGVLQSVRFVF (SEQ ID NO:21), acQGVLQNVRF (SEQ ID NO:22), FQGVLQNVKFVF (SEQ ID NO:23), FQGVLNNVRFVF (SEQ ID NO:24), AQGVLQNVRFVF (SEQ ID NO:25), FAGVLQNVRFVF (SEQ ID NO:26), FQGVAQNVRFVF (SEQ ID NO:27), FQGVLQNVRFVA (SEQ ID NO:28), FQGVLANVRFVF (SEQ ID NO:29), FQGVLQNVRFV (SEQ ID NO:30), QGVLQNVRFVF (SEQ ID NO:31), FQGVLQNVRF (SEQ ID NO:32), and FQGVLQNVRFVF (SEQ ID NO:6).

In one embodiment, the peptides of the present invention comprise both D and L amino acids. As such the peptides of the present invention include retro-inverso peptides. Thus, in one aspect, the present invention relates to a retro-inverso synthetic peptide of 4 to 12 amino acids in length, wherein said retro-inverso peptide comprises the amino acids sequence, from C-terminal (left) to N-terminal (right): ri-R'1-X'1-X'2-X'3-X'4-R'2, wherein ri denotes a retro-inverso peptide and all amino acids are D amino acids; X'1 is selected from the group consisting of N, Q, D and S; X2 is selected from the group consisting of V, I and L; X3 is selected from the group consisting of R and K; and X4 is selected from the group consisting of V, I, L and F; R1 is a hydrogen or a peptide of 1 to 6 amino acids, a hydroxide or an amide; and R2 is a peptide of 1 to 3 amino acids, an acyl or an aryl group.

Retro-inverso peptides have been successfully applied to increase the stability and biological activity of peptide sequences for therapeutic applications (reviewed in Chorev M, Goodman M (1993), Acc. Chem. Res. 26:266–273. See also Goodman et al., (1979), Acc. Chem. Res. 12:1–7.) The methods of Goodman et al. can be used to prepare retro-inverso peptides of the present invention.

In certain embodiments, the peptides of the invention are immobilized, e.g., by attachment to a substrate suitable for cell growth. As such the present invention also relates to peptide-substrate combinations comprising the peptides of the inventions and suitable substrates wherein the peptides are attached to suitable substrates. Suitable substrates include synthetic or natural polymers, metals, glass, glass fibers, ceramics, polyethylene, cellulose, nylon, polycarbonate, polyurethane, polyester, tetrafluoroethylene polymers, polyester, silicone rubbers, and the like, and may be in the form of an, e.g., plate, bottle, bead, fabric or other surface. The peptide-substrate combinations of the present invention are useful for promoting adhesion, migration, and growth of anchorage-dependent cells, e.g., endothelial cells, in vitro and in vivo.

In the peptide-substrate combinations of the invention, peptides are attached, directly or indirectly, to a substrate by adsorption (e.g., by overnight incubation of a peptide composition in PBS on a polystyrene substrate), via a linker, ligand/receptor interaction, covalent bonding, hydrogen bonding, and/or ionic bonding. In one embodiment, the peptide is linked to a cell culture substrate, e.g., as described in U.S. Pat. Nos. 5,330,911; 5,278,063; 4,822,741; and 4,789,602.

In contrast to the use of the term "immobilized" (in the context of being immobilized to a substrate as in the peptide-substrate combination of the present invention), the peptides of the invention may be used in peptide conjugates. As such, the present invention also relates to peptide conjugates comprising the peptides of the invention and a water-soluble polymer as described, for example, in U.S. Pat. No. 5,770,563. In one embodiment, such peptide conjugates are used to provide peptides with increased the stability in body fluids, decreased the sensitivity to proteases, or with a decreased rate of clearance from circulation. The water soluble polymers used to form said peptide conjugates include polysucrose, dextran, polystyrene, polyethylene glycol, polyvinyl alcohol, polylactide, poly(lactide-co-glycolactide), poly(oxyethylene)-poly(oxypropylene) (PEO-PPO) block copolymers. In one embodiment, the water soluble polymer is a branched carbohydrate polymer, e.g., polysucrose (such as FICOLL™) or dextran.

The term "polylactide" is used in a generic sense to include polymers of lactic acid alone, copolymers of lactic acid and glycolic acid, mixtures of such polymers, mixtures of such copolymers, and mixtures of such polymers and copolymers, the lactic acid being either in racemic or in optically active form.

IV. Pharmaceutical Compositions

The present invention also provides a pharmaceutical composition comprising a peptide of the present invention, and a pharmaceutically acceptable excipient or carrier.

While it is possible to administer the peptide of the invention alone, it is preferable, in some cases, to present it as part of a pharmaceutical formulation. Pharmaceutically acceptable carriers typically include carriers known to those of skill in the art, including pharmaceutical adjuvants. Generally these pharmaceutically acceptable carriers will include water, saline, Ringers solution, Ringer's lactate, 5% dextrose, buffers, and other compounds described, e.g., in the MERCK INDEX, Merck & Co., Rahway, N.J. See, also, Bioreversible Carriers in Drug Design, Theory and Application, Roche (ed.), Pergamon Press, (1987). The peptides may be mixed with a variety of carrier compounds depending on the form of preparation desired for administration.

These formulations typically comprise the pharmacological agent (i.e., the peptide) in a therapeutically or pharmaceutically effective dose together with one or more pharmaceutically or therapeutically acceptable carriers and optionally other therapeutic ingredients. Various considerations are described, e.g., in Gilman et al. (eds) (1990) Goodman and Gilman's: The Pharmacological Bases of Therapeutics, 8th Ed., Pergamon Press; Novel Drug Delivery Systems, 2nd Ed., Norris (ed.) Marcel Dekker Inc. (1989), and Remington's Pharmaceutical Sciences. Methods for administration are discussed therein. In particular, the pharmaceutical compositions of the invention may be administered intravenously, subcutaneously, orally, transdermally, intramuscularly, topically (e.g., by intravascular injection into vessels infiltrating a tumor or tumor metastasis), or by intracavity or peristaltic administration.

V. Methods of Using the Peptides of the Present Invention

It has been discovered that the peptide compositions of the invention inhibit angiogenesis, cell adhesion and proliferation, and wound repair when administered in a soluble form. However, when, the peptides are immobilized on a substratum, as in the case of peptide-substrate combination of the present invention, they promote adhesion, spreading and proliferation of cells. Thus, the peptides of the invention have diverse uses, including in treatment of angiogenesis-mediated diseases, production of vascular grafts and artificial blood vessels containing endothelial cells or readily infiltrated by endothelial cells, and other uses, some which are discussed in this section and in the Examples, infra.

A) Inhibition of Cell Adhesion to an Extracellular Matrix

The present invention provides reagents and methods for inhibiting adhesion of a cell to an extracellular matrix, and/or for inhibiting proliferation of cells on an extracellular matrix. Usually, the adhesion is mediated by $\alpha_3\beta_1$ integrin and the cell (e.g., an endothelial, epithelial, smooth muscle, hematopoietic, or a tumor cell) expresses, or is capable of expressing, the $\alpha_3\beta_1$ integrin. Exemplary extracellular matrices include those comprising thrombospondin-1 (TSP1), type IV collagen, laminins, and entactin/nidogen.

The inhibition may take place in vivo or in vitro, and is accomplished by contacting the cell and/or extracellular matrix with a composition comprising a peptide of the invention. Usually, the cell and extracellular matrix are contacted together with the compositions of the invention. Contacting in vitro may be accomplished, for example, by adding the peptide to a cell culture medium. Contacting in vivo may be accomplished by administering a sterile or pharmaceutically acceptable composition comprising the peptide to an animal (e.g., patient). The composition may be administered systemically or, alternatively, may be administered locally (e.g., topically to a blood vessel wall).

In one embodiment, a peptide conjugate of this invention is used to enhance the inhibition of cell adhesion to extracellular matrix compared to the use of the peptide alone.

The amount or concentration of the peptide administered in vivo or in vitro will vary according to the specific application, and can be determined by one of skill following the guidance of this disclosure. In one embodiment, the concentration of peptide administered ranges from 1 μM to 10 mM, and in one embodiment, from 5 μM to 1 mM, in one embodiment, from 5 μM to 100 μM, and in one embodiment, from 5 μM to 40 μM. The adhesion- or proliferation-inhibiting amount of a peptide composition can be determined as described in the Examples infra, e.g., by assaying the adhesion and/or proliferation of cells such as bovine aorta endothelial cells (BAE) in the presence of the peptide to be tested. The adhesion/proliferation inhibiting amount can be described as the amount that inhibits adhesion or proliferation of a specified cell type by at least 10%, and in one embodiment, at least 20%, and in one embodiment at least 50% compared to a control peptide or BSA In one embodiment, the peptides of the present invention are administered to a cancer patient, wherein that patient's tumor expresses $\alpha_3\beta_1$ integrin, to inhibit adhesion of the tumor cells to their surrounding matrix. Such inhibition of adhesion can suppress tumor growth or increase responsiveness to chemotherapy or radiotherapy. Cancers amenable to this treatment would include carcinomas (including breast carcinoma and small cell lung carcinoma), neuroectoderm-derived tumors, hemangiomas, endotheliomas and Kaposi's sarcoma.

In one embodiment, the peptides are used in an in vitro adhesion assay to define function of the $\alpha_3\beta_1$ integrin in a specific cell type.

B) Inhibition of Cell Motility

As discussed infra, the peptides of the invention inhibit cell motility (e.g., motility of an endothelial cell), and such inhibition may occur even in the absence of proliferation. As used herein in this context, cell motility refers to the movement or cells across a substrate and can be measured using a scratch wound repair assay as described infra.

Specific inhibitors of cell motility have a variety of uses. The peptides in soluble forms can be used to inhibit the motility of tumor cells invading surrounding tissue from a primary tumor. Such treatment would prevent tumor metastasis.

The peptides could be used to inhibit motility of endothelial cells invading a tumor or other tissue associated with pathological angiogenesis. Inhibition of motility would alleviate symptoms of these diseases. It is to be noted that a peptide can both promote and inhibit motility. Examples are provided (in the "Examples" section infra) where the peptide stimulates motility to itself, but the same peptide can be used as a soluble inhibitor to prevent motility stimulated by other α3β1 integrin ligands such as thrombospondin-1, laminins, entactin, or type IV collagen).

C) Inhibition of Angiogenesis

In one aspect, the invention provides a method of treating an angiogenesis-mediated disease in an animal by administering to the animal an effective amount of a composition containing a peptide of the invention. As used herein, "angiogenesis" has its normal meaning in the art and refers to the generation of new blood vessels into a tissue or organ, a process that involves endothelial cell proliferation. Under normal physiological conditions, humans or animals undergo angiogenesis only in restricted situations. For example, angiogenesis is normally observed in wound healing, fetal and embryonic development, and formation of the corpus luteum, endometrium and placenta. However, persistent, unregulated angiogenesis occurs in a multiplicity of disease states, tumor metastasis and abnormal growth by endothelial cells and supports the pathological damage seen in these conditions.

Both controlled and uncontrolled angiogenesis are thought to proceed in a similar manner. Endothelial cells and pericytes, surrounded by a basement membrane, form capillary blood vessels. Thus, angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. The diverse pathological disease states in which unregulated angiogenesis is present are referred to herein as "angiogenesis-mediated" conditions or diseases. Angiogenesis-mediated diseases include, without limitation, diabetic retinopathy, retinopathy of prematurity, rheumatoid arthritis, macular degeneration, atherosclerosis plaque formation, psoriasis, restenosis, and cancers. Additional diseases are associated with inadequate angiogenesis, including without limitation peripheral vascular disease, diabetes, and coronary artery disease.

The inhibition of angiogenesis according to the methods of the invention is particularly important in treatment of cancer because of the important role neovascularization plays in tumor growth. In the absence of neovascularization of tumor tissue, the tumor tissue does not obtain the required nutrients, slows in growth, ceases additional growth, regresses and ultimately becomes necrotic, resulting in killing of the tumor. This is characteristic of most solid tumors, but also is important in other cancers, for example B cell lymphoproliferative diseases (Vacca, et al Leukemia and Lymphoma 20:27–38, 1995). Thus, the methods of the invention are useful for treatment of cancers including solid tumors of the lung, pancreas, breast, colon, larynx, ovary, prostate, liver, stomach, brain, and head and neck. Angiogensis-depdendent tumors also include various hematological malignancies, Kaposi's sarcoma, endotheliomas, and hemangiomas. In one embodiment, the invention provides a method of inducing solid tumor tissue regression in a patient comprising administering a composition comprising a peptide of the invention, e.g., by systemic administration, intravascular injection into a tumor or tumor site. The dose administered is the amount sufficient to inhibit neovascularization of a solid tumor tissue, and is typically administered in the ranges described supra. In one embodiment, the concentration of peptide administered ranges from 0.1 µM to 10 mM, and in one embodiment, 5 µM to 1 mM, in one embodiment, 5 µM to 100 µM, and in one embodiment, 5 µM to 40 µM. The angiogenesis-inhibiting activity of a peptide composition can be determined as described in the Examples infra, e.g. using a rat corneal pocket and chick chorioallantoic membrane (CAM) angiogenesis assays (Good et al., 1990; Iruela-Arispe et al., 1999).

In the treatment of cancer, the invention contemplates the administration of the anti-angiogenic agent either as a sole therapy or in conjunction with other therapies such as conventional chemotherapy, gene therapy, or radiotherapy directed against solid tumors. In one embodiment, the administration of the peptides of the invention is conducted during or after other therapeutic intervention, e.g., chemotherapy, although it is preferable to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

D) Inhibition of Cell Proliferation

The peptides of the present invention can be used for inhibiting proliferation of cells expressing α3β1 integrin. The cells can be any type, including endothelial and SCLC cells. Cell proliferation can be measured using the Cell-Titer calorimetric assay as detailed in the Examples.

E) Promotion of Proliferation of Cells

The invention provides methods for promoting proliferation of cells (e.g., endothelial cells), by contacting the cells with a peptide-substrate combination (immobilized peptide) of the invention in vitro or in vivo, under conditions supportive of cell division. This method provides an efficient method for growing endothelial or other cells, e.g., for transplantation, for preparing material to be infiltrated or coated with cells (e.g., for implantation or use as a prosthesis), or other uses. The cells can be of any type that express α3β1 including endothelial cells and carcinoma cells. The cells may be of human or non-human origin (e.g., from rat, mouse, human and non-human primate).

The phrase "under conditions supportive of cell division," as used herein, refers to an in vitro environment in which cells are maintained at a suitable temperature (e.g., about 37° C.), and in the presence of nutrients (e.g., RPMI medium), growth factors (e.g., 15% FBS), and appropriate pH and atmosphere (e.g., 5% $CO_2$), and the like. Cell and tissue culture conditions and techniques are well known and are described, for example, in Freshney, R. I. Culture of animal cells. $3^{rd}$ edition, John Wiley and Sons, New York, 1994. The phrase "under conditions supportive of cell division," as used herein, also refers to an in vivo environment such as the surface of blood vessels or elsewhere in a living animal.

In one embodiment, the substrate to which the peptide is attached or adsorbed is a substrate suitable for culturing cells, e.g., endothelial cells. Suitable substrates for cell culture are well known and include without limitation glass or plastic plates, bottles, beads.

Additional substrates suitable for supporting cells include materials such as synthetic or natural polymers, metals, glass, glass fibers, ceramics, polyethylene, cellulose, nylon, polycarbonate, polyurethane, polyester, tetrafluoroethylene polymers, polyester, and silicone rubbers, which are particularly useful for producing materials that can be used as medical or prosthetic devices, e.g., vascular patches or artificial blood vessels.

In a particular embodiment of the invention, the peptides of the invention are immobilized on a substrate to promote proliferation of endothelial cells for use as vascular grafts or artificial blood vessels. In one embodiment, endothelial cells are grown on the substrate in vitro and the substrate is subsequently introduced into the animal (e.g., patient). In a related embodiment, the contacting of peptide with the endothelial cell takes place in a blood vessel (including both natural and artificial blood vessels). For example, a material (e.g., artificial blood vessel) to which a peptide of the invention is adsorbed or attached is introduced into an animal (e.g., patient) and endothelial cells from adjacent tissue are allowed to migrate into the surface of the material (e.g., the luminal surface of an artificial vessel) and proliferate in situ. The amount or density of the peptide used can be any density that increases cell proliferation over background levels (e.g., proliferation on a material coated with human serum albumin). In one embodiment, the effective density of the surface immobilized peptide ranges from 1 to 5 pmoles/mm$^2$.

Suitable peptides are disclosed herein and others/dosages may be identified by the methods described in the Examples and other methods known in the art. For example, as described in greater detail infra, a peptide (e.g., 10 μM) may be adsorbed to a glass or polystyrene substrate and the ability of MDA-MB-435 breast carcinoma cells (ATCC # HTB-129) to adhere and proliferate can be determined as described in the Examples, infra. See, e.g., Guo et al., J. Biol. Chem., 267: 19349–19355 (1992). Using this assay or equivalent assays known in the art, the adhesion-promoting and proliferation-stimulating activity of a composition can be determined (e.g., compared to a standard such as peptide 678 or BSA).

In a related embodiment, the invention provides substrates onto which a peptide of the invention is adsorbed or attached, for use in vivo or in vitro for stimulation of cell adhesion and growth, e.g., endothelial cell growth. In one embodiment, the present invention provides an artificial blood vessel comprising a tube of a porous synthetic polymer on a surface of which the peptide of the present invention is covalently bonded. Such bonding could take place, for example, through hydroxyl groups, sulfhydryl groups, carboxyl groups, epoxy groups or amino groups. The porous synthetic polymer includes such materials as a tube of a woven or knitted fabric of polyester fibers or expanded polytetrafluoroethylene, and other suitable polymers for use as an artificial blood vessel. See, e.g., U.S. Pat. No. 5,591,225.

EXAMPLES

Example 1

General Procedures

Proteins and peptides—Calcium replete TSP1 was purified from human platelets (Roberts et al., 1994). Synthetic peptides containing TSP1 sequences were prepared as previously described (Guo et al., 1992 (both references); Guo et al., 1997; Prater et al., 1991; Murphy-Ullrich et al., 1993; Gao et al., 1996). Recombinant fragments (provided by Dr. Tikva Vogel) and GST fusion proteins expressing fragments of TSP1 (provided by Dr. Jack Lawler, Harvard) were prepared as previously described (Vogel et al., 1993; Legrand et al., 1992). Bovine type I collagen and murine Type IV collagen were obtained from Becton Dickenson Labware Division, and human vitronectin was from Sigma. Fibronectin was purified from human plasma (National Institutes of Health Blood Bank) as described (Akiyama et al., 1985). Murine laminin-1 purified from the EHS tumor was provided by Dr. Sadie Aznavoorian (National Cancer Institute). Recombinant human insulin-like growth factor-1 (IGF1) was from Bachem.

The peptide GRGDSP (SEQ ID NO:9) was obtained from Gibco/BRL. A non-peptide antagonist of αv integrins was provided by Dr. William H. Miller (SmithKline Beecham Pharmaceuticals, King of Prussia, Pa.) (Keenan, 1997).

Bovine aortic endothelial (BAE) cells were isolated from fresh bovine aortae and were used at passages 3–10. BAE cells were maintained at 37 o in 5% $CO_2$ in DMEM (low glucose) medium, containing 10% FCS, 4 mM glutamine, 25 μg/ml ascorbic acid, and 500 U/ml each of penicillin G potassium and streptomycin sulfate. Media components were obtained from Biofluids Inc., Rockville, Md. Primary human umbilical vein endothelial cells (HUVEC) were provided by Dr. Derrick Grant, NIDCR, and human dermal microvascular endothelial (HDME) cells were purchased from Clonetics Corp., San Diego, Calif. HUVEC cells were maintained in medium 199E supplemented with 20% FCS, 10 μg/ml heparin, 80 μg/ml endothelial mitogen (Biomedical Technologies, Inc., Stoughton, Mass.), glutamine, penicillin, and streptomycin sulfate. HDME cells were maintained in MCDB medium containing glutamine, 5% FCS, 10 ng/ml epidermal growth factor, 1 μg/ml hydrocortisone, 50 μg/ml ascorbic acid, 30 μg/ml heparin, 4 ng/ml FGF2, 4 ng/ml VEGF, 5 ng/mil IGF1, and 50 μg/ml gentamicin.

The OH-1 cell line (Adachi et al., 1998) was provided by Dr. Joel Shaper (Johns Hopkins University, Baltimore, Md.). Variant OH-1 arose after prolonged culture of OH-1 and lost the classical morphology. H128, H69, H82, and H209 cell lines were purchased from the American Type Culture Collection, Rockville, Md. Those cell lines were established from pleural fluids of SCLC patients (Wu et al., 1995). N417 and H345 cell lines (Shrive et al., 1996) were provided by Dr. A. Gazdar. N417 originated from lung and H345 from a bone marrow metastasis. All cell lines were cultured suspended in RPMI 1640 medium with 15% fetal calf serum (Biofluids Inc., Rockville, Md.) at 37° C. in a 5% $CO_2$ incubator. The medium was changed every 5 days. These cells were passaged every 9–11 days. In brief, cells were centrifuged at 400×g for 2 min, and the medium was aspirated. Cell pellets were washed once with RPMI 1640 containing 5 mM $MgCl_2$ and treated for 5 min with 1/16 volume of deoxyribonuclease-1 (Biofluids Inc., Rockville, Md.) in 5 ml RPMI 1640 containing 5 mM magnesium chloride. Cells were triturated three times, and 1/10 volume of trypsin (10×, Biofluids Inc.) was added for 5 min and triturated as above. The cells were washed once with the same medium, centrifuged and suspended in fresh medium.

Cell proliferation was measured using the Cell-Titer colorimetric assay (Promega) as previously described (Vogel et al., 1993). A 100 μl volume of BAE cell suspension at 50,000 cells/ml in DMEM containing 1% FBS and supplemented with 10 ng/ml FGF2 was plated in triplicate in 96 well tissue culture plates either in the presence of peptides in solution or in wells that were pre-coated with 100 μL of the peptides at 40° C. overnight and aspirated just before adding cells. Cells were grown for 72 hours at 37° C. in a humidified incubator with 5% CO2. HUVEC proliferation was measured by the same protocol but using medium 199 containing 5% FCS without heparin. HDME cell proliferation was measured in MCDB growth medium without heparin, VEGF, or FGF2.

Figure 1:
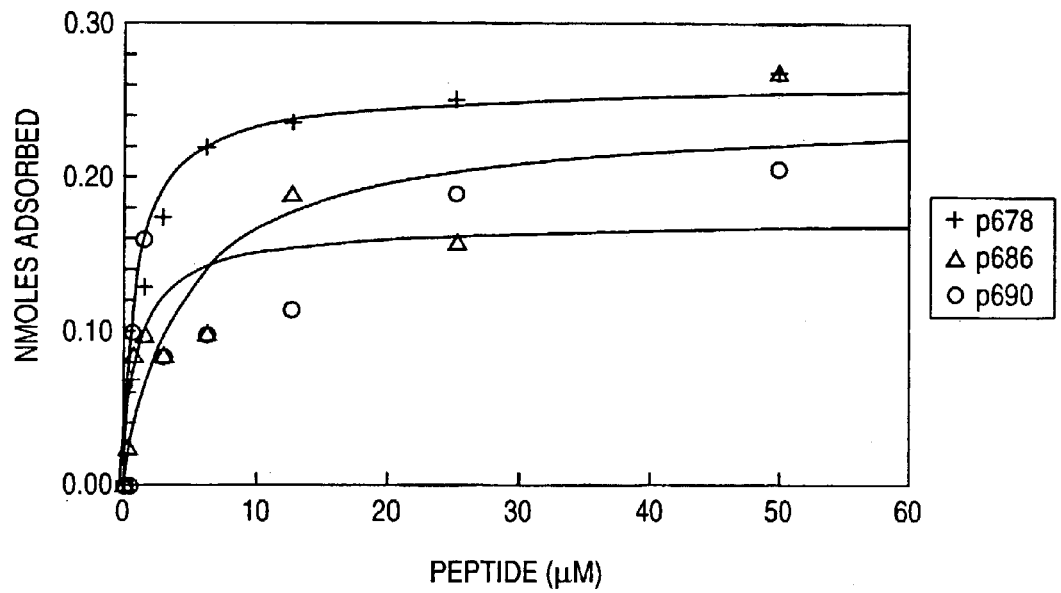
FIG. 1 displays a plot of amount (moles) of adsorbed peptide onto polystyrene versus concentration for three different peptides: peptide 678 (+), peptide 686 (Δ) and peptide 690 (○). Peptides dissolved in PBS at 0.4 to 50 μM were incubated in polystyrene microliter plate wells overnight at 4° C. The wells were washed 3 times with distilled water. Adsorbed peptide was quantified using the BCA assay (Pierce Chemical) measuring absorbance at 570 and 630 nm as described by the suppliers protocol. The assay was calibrated using purified peptide in solution as a standard. Results are presented as the mean of duplicate determinations at each concentration. Adsorption is for a 67 mm² area of polystyrene.

Adhesion assays of cells other than small cell lung carcinoma (SCLC)-Adhesion was measured on polystyrene or glass substrates coated with peptides or proteins as previously described (Guo et al., 1992). Peptides dissolved in PBS at 0.4 to 50 μM were incubated in polystyrene microliter plate wells overnight at 4° C. The wells were washed 3 times with distilled water. Adsorbed peptide was quantified using the BCA assay (Pierce Chemical) measuring absorbance at 570 and 630 nm as described by the supplier's protocol. The assay for adsorption was calibrated using purified peptide in solution as a standard. An example for such assay is provided in FIG. 1. After blocking with 1% BSA in Dulbecco's PBS, adhesion assays were performed by adding cells suspended in DMEM (BAE cells) or medium 199 (human cells) containing 1 mg/ml BSA. Cell attachment and spreading was quantified microscopically.

For adhesion assays of SCLC, these cells were washed once with RPMI 1640 and centrifuged at 400×g for 3 min. The pellet was suspended in 2.5 mM EDTA in PBS, pH 7.4 and incubated for 10 min at 37° C. After trituration three times and centrifugation, the cells were resuspended in RPMI 1640 containing 0.1% BSA (Sigma Co. St Louis, Mo.). Trypan blue staining showed greater than 90% cell viability.

Adhesion of SCLC cells to extracellular matrix proteins. Extracellular matrix proteins or peptides in Dulbecco's PBS were adsorbed onto polystyrene by incubating overnight at 4° C. Adsorption isotherms of TSP1 on plastic have been reported previously (Hudson et al., 1979). The supernatant fluid was removed, and the dishes were incubated with Tris-gelatin (ICN) (50 mM Tris-HCl, 110 mM NaCl, 5 mM $CaCl_2$, 0.1 mM phenylmethylsulfonyl fluoride, 0.2% gelatin and 0.02% $NaN_3$, pH 7.8) or Dulbeccos PBS with 1% BSA, as indicated, for 30 min to minimize nonspecific adhesion. The disks were washed twice with cold PBS, pH 7.2 and overlayed with dissociated SCLC cells prepared as described above at a density of $2.5×10^5/cm^2$.

Inhibition assays were performed using the following function blocking antibodies: 6D7 (α2β1), P1B5 (Gibco-BRL, α3β1), 407279 (Calbiochem, α4β1), and P1D6 (Gibco-BRL, α5β1), P4C2 (Gibco-BRL, α4β1), and mAb13 (Dr. Ken Yamada, anti-β1). The function blocking CD36 antibody OKM-5 was purchased from Ortho-mune (Raritan, N.J.). The integrin $α_vβ_3$ antibody LM609 was the gift of Dr. David Cheresh, Scripps Research Institute (Fernandez et al., 1998). Rat monoclonal antibodies to the human β1 integrin (mAb 13) and $α_5$ subunits (mAb16) were provided by Dr. Kenneth Yamada (National Institute for Dental Research) (Adams, 1995). The β1 integrin-activating antibody TS2/16 (Hemler et al., 1984) and the CD98 antibody 4F2 were prepared from hybridomas obtained from the American Type Culture Collection. Immunofluorescence analysis of cell adhesion was performed as described previously, using BODIPY TR-X phallacidin (Molecular Probes, Inc. Eugene, Oreg.) to visualize F-actin or using murine primary antibodies followed by BODIPY FL anti-mouse IgG to localize integrins, vinculin (Sigma), or focal adhesion kinase (clone 77, Transduction Laboratories; Sipes et al., 1999).

For inhibition studies with SCLC cells, inhibitors or antibodies were added and incubated with SCLC cells at the indicated concentrations. After incubation for 60–90 min at 37° C., the disks were washed by dipping six times in PBS, pH 7.2, fixed with 1% glutaraldehyde in PBS, pH 7.2, and stained with Diff-Quik. Attached cells were counted microscopically.

Scratch Wound Repair

The in vitro wound healing assay used was a slight modification of that described by Joyce et al. (Joyce et al., 1989). A confluent monolayer of BAE cells pretreated with 10 μg/ml 5-fluorouracil for 24 hours were used in this assay. A straight wound about 2.0 mm wide was made in the monolayers using the flat edge of a sterile cell scraper (Costar #3010), and the cells were allowed to migrate back into the wound site in the presence of TSP1 peptides. Mitosis of the BAE cells in the monolayers was inhibited by addition of 5-fluorouracil, so that the rate of wound closure was due solely to the migration of cells into the wound sites. The distances between the wound margins were measured as soon as the wound was made and 24 hours later using a grid incorporated into the eye piece of the microscope. All data represent the results obtained from three independent scratch wounds for each peptide tested.

Proliferation of SCLC Cells

Effects of soluble and substrate-bound TSP1 or TSP1 peptides on cell proliferation were quantified using a tetrazolium proliferation assay (Celltiter, Promega). Treatment with soluble TSP1 was performed in 96-well tissue culture plates, and proliferation was determined after 72 h in RPMI medium containing 15% FCS. Proteins and peptides were immobilized on Nunc Maxisorp 96 well plates by overnight incubation with the proteins or peptides dissolved in 50 μl of sterile Dulbecco's PBS. The supernatant fluid was removed, and the wells were incubated for 30 min. in DPBS containing 1% BSA. OH1 cells ($1×10^4$/well) were added in RPMI containing 15% FCS and incubated for 72 h at 370 in 5% $CO_2$. For assessing inhibition by soluble proteins or peptides, OH1 cells were grown in suspension in Nunclon 96 well tissue culture plates using the same medium.

Chorioallantoic Membrane (CAM) Angiogenesis Assay

Fertilized Leghorn chicken eggs were obtained from Ramona Duck farm (Westminster, Calif.). At day 3 of development, the embryos were placed on 100 mm petri dishes. Assays were performed as previously described (Iruela-Arispe et al., 1999). Briefly, vitrogen gels containing growth factors (FGF-2 (50 ng/gel) and VEGF (250 ng/gel)) were allowed to polymerize in the presence or absence of TSP1 peptides. Peptides were filtered on Centricon P100 prior to their analysis on the CAM assays to eliminate traces of endotoxin. Pellets were applied to the outer 1/3 of the CAM, and the assay was performed for 24 h. Detection of capillary growth was done by injection of FITC-dextran in the bloodstream and observation of the pellets under a fluorescent inverted microscope. Positive controls (growth factors and vehicle), as well as negative controls (vehicle alone) were placed in the same CAM and used as reference of 100% stimulation or baseline inhibition (0%), and response to the peptides was determined according to these internal controls. Assays were performed in duplicate in each CAM and in four independent CAMs (total of 8 pellets). Statistical evaluation of the data were performed to check whether groups differ significantly from random by analysis of contingency with Yates' correction.

Motility Assays—Chemotaxis of MDA-MB-435 cells to TSP1 peptides was measured in modified Boyden chambers using polylysine coated 8 μm polycarbonate filters as previously described for intact TSP1 (Chandrasekaran et al., 1999).

Multiple Sequence Alignment—Protein sequences were compared using MACAW software (National Center for Biotechnology Information, National Library of Medicine, version 2.0.5) by the segment pair overlap and Gibbs sampler methods (Schuler et al., 1991; Lawrence et al., 1993).

Example 2

Localization of Region of TSP1 Recognized by the α3β1 Integrin

Figure 2:
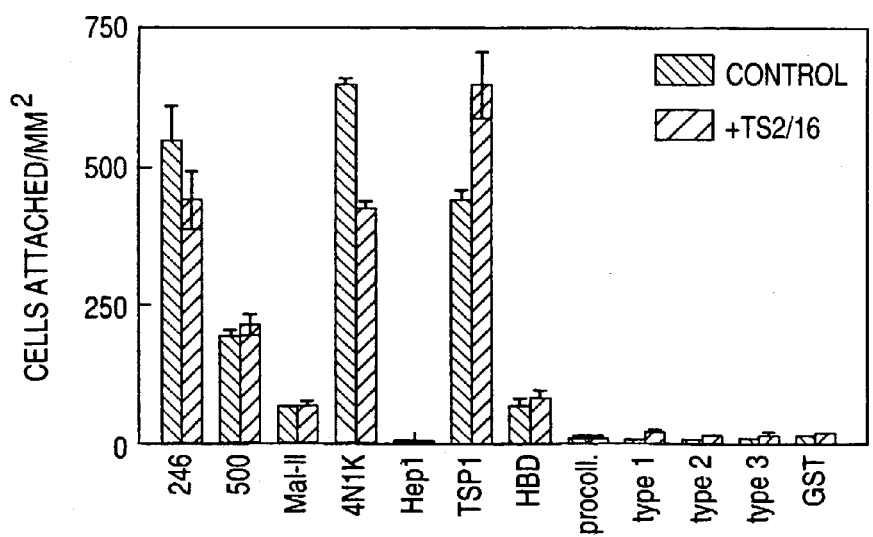
FIG. 2 is a graph illustrating the adhesion of MDA-MB-435 breast carcinoma cells to recombinant thrombospondin-1 (TSP1) fragments and TSP1 peptides. Adhesion to synthetic TSP1 peptides adsorbed at 10 μM (Peptide 246, KRFKQDGGWSHWSPWSS (SEQ ID NO:1); 500, NGVQYRNC (SEQ ID NO:2); Mal II, SPWSSCS-VTCGDGVITRIR (SEQ ID NO:3); 4N1K, KRFYVVM-WKK (SEQ ID NO:4); HepI, ELTGAARKGSGR-RLVKGPD (SEQ ID NO:5)), TSP1 (0.11 μM), recombinant 18 kDa heparin-binding domain (HBD, 2.7 μM), or GST-fusion proteins expressing the TSP1 procollagen domain, type 1, type 2, type 3 repeats, or GST alone (2 μM) was measured in the absence (solid bars) or presence of 20 μg/ml of the β1 integrin-activating antibody TS2/16 (striped bars). Results (mean±SD) are presented for a representative experiment performed in triplicate.

In initial attempts to localize the region of TSP1 recognized by the α3β1 integrin, approximately 85% of the TSP1 sequence in the form of synthetic peptides or GST or T7-fusion proteins were tested for promotion of β1 integrin-dependent adhesion of MDA-MB-435 breast carcinoma cells (FIG. 2). Among the recombinant fragments tested, only an 18 kDa fragment of the amino-terminal heparin-binding domain had significant adhesive activity, although the recombinant type I repeats had adhesive activity for MDA-MB-435 cells in some experiments (results not shown). A recombinant GST-fusion of the type 3 repeats of TSP1 including the RGD sequence had minimal adhesive activity for MDA-MB-435 cells (FIG. 2), in contrast to human melanoma cells, which avidly attached on substrates coated with the same concentrations of this fragment (Sipes et al., 1999). The β1 integrin activating antibody TS2/16 did not enhance cell attachment to any of these recombinant fragments but reproducibly stimulated attachment on intact TSP1 (FIG. 2). Synthetic heparin-binding peptides from the type 1 repeats (peptide 246) (Guo et al., 1992) and the CD47-binding peptide 4N1K (Gao et al., 1996) also promoted adhesion, but TS2/16 did not enhance adhesion of MDA-MB-435 cells to these peptides. CD36-binding peptides from the procollagen domain (peptide 500) or the type I repeats (Mal-II) (Dawson et al., 1997) had weaker adhesive activities and were also insensitive to TS2/16. The focal adhesion disrupting peptide Hep I from the amino terminal domain of TSP1 (Murphy-Ullrich et al., 1993) did not promote MDA-MB-435 cell adhesion. Although these experiments did not detect a β1 integrin-dependent adhesive sequence in TSP1, the possibility remains that these regions of TSP1 contain a conformation-dependent recognition motif that is inactive in the recombinant fusion proteins due to misfolding.

Figure 3A:
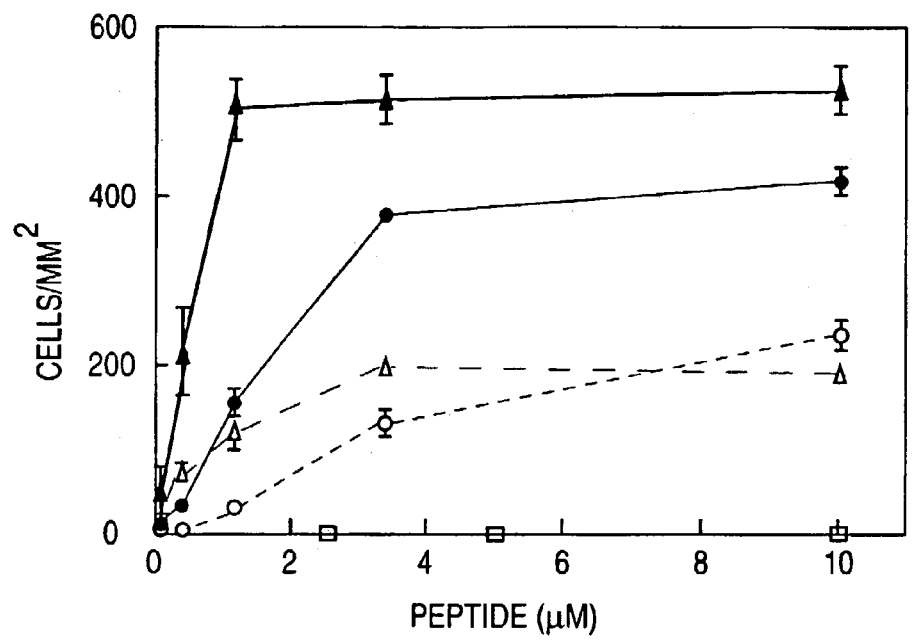
FIGS. 3A and 3B are graphs illustrating the adhesion of MDA-MB-435 breast carcinoma cells to TSP1 peptides and laminin-1 peptide GD6. Panel A: MDA-MB-435 breast carcinoma cell attachment (closed symbols) and spreading (open symbols) was determined on polystyrene substrates coated with the indicated concentrations of TSP1 peptide 678 (FQGVLQNVRFVF (SEQ ID NO:6), circles), TSP1 peptide 701 (TPGQVRTLWHDP (SEQ ID NO:7), squares), or the murine laminin-1 peptide GD6 (KQNCLSSRAS-FRGCVRNLRLSR (SEQ ID NO:8), triangles). Results are presented as mean±SD, n=3. Panel B: Spreading of MDA-MB-435 or MDA-MB-231 cells on substrates coated with 3.3 μM TSP1 peptide 678, 1.1 μM laminin-1 peptide GD6, or 50 μg/ml TSP1 was determined using untreated cells (solid bars), or cells treated with 5 μg/ml of the β1 activating antibody TS2/16 (gray bars), or 3 nM IGF1 (striped bars, MDA-MB-435 cells only), mean±SD, n=3.

A multiple alignment search using MACAW software was used to identify TSP1 sequences that might be related to the α3β1 integrin-binding murine laminin-1 peptide KQNCLSSRASFRGCVRNLRLSR (GD6 peptide; SEQ ID NO:8) derived from the A chain of murine laminin-1 (Gehlsen et al., 1992), which strongly promoted MDA-MB-435 cell adhesion (FIG. 3A). This search identified four TSP1 sequences related to the laminin peptide (Table 1).

TABLE 1

TSP1 sequences related to murine laminin-1 peptide GD6. The amino acid sequences for human and murine TSP1 and laminin-1 peptide GD6 were compared by multiple alignment using MACAW. Alignment scores were determined by segment pair overlap or Gibbs sampler (*) methods.

| Peptide origin | sequence | MP score vs. GD6 | p value | SEQ ID NO: |
|---|---|---|---|---|
| laminin GD6 | KQNCLSSRASFRGCVRNLRLSR | — | — | 8 |
| laminin p679 | FRGCVRNLRLSR | — | — | 12 |
| TSP1(598–608) | NCLPCPPRFTG | 42.0 | $5.9 \times 10^{-8}$ | 33 |
| TSP1(188–199) | DNFQGVLQNVRF | 39.0 | $5.9 \times 10^{-7}$ | 34 |
| TSP1(392–405) | NNRCEGSSVQTRTC | 35.0 | $4.5 \times 10^{-4}$ | 35 |
| TSP1(1059–1077) | RNALWHTGNTPGQVRTLWH | 43.3* | $2.1 \times 10^{-8}$ | 36 |

The single peptide identified by the Gibbs Sampler method, derived from the C-terminal domain of TSP1 (residues 1059–1077), did not support adhesion nor inhibit adhesion of MDA-MB-435 cells to TSP1 or other α3β1 integrin ligands (FIG. 3A and results not shown). Because a synthetic peptide containing the last 12 residues of peptide GD6 (peptide 679, Table 1) had similar activity to the intact peptide (see below), the two peptides identified by Segment Pair Overlap that aligned outside this sequence were not tested. Both of these peptides were derived from regions of the type 1 (residues 392–405) or type 2 repeats sequences (residues 598–608) that did not support α3β1-dependent adhesion when expressed as GST-fusion proteins (FIG. 2).

Figure 3B:
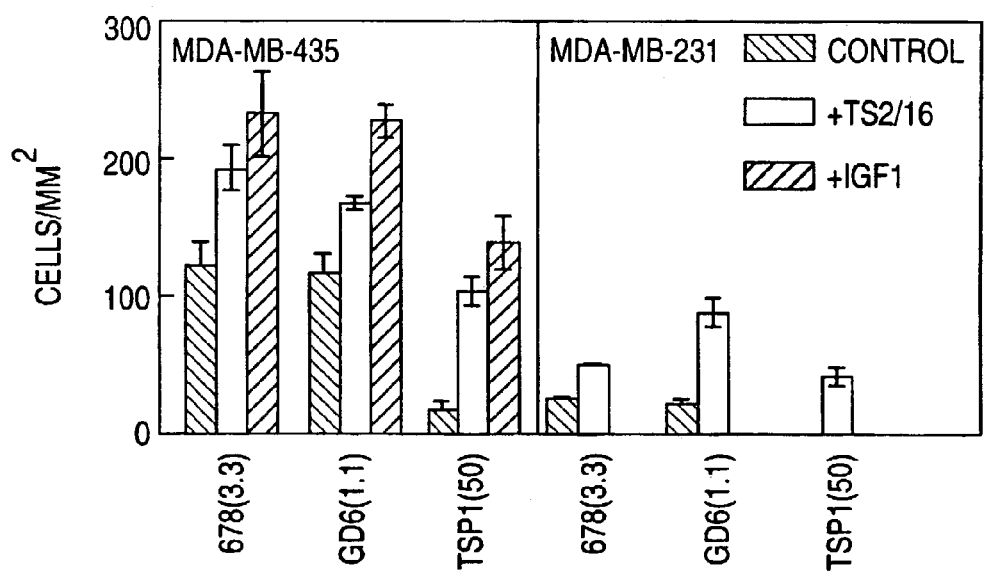

The remaining sequence is from a region of the N-terminal domain of TSP1 (residues 188–199) that was not covered by the recombinant fragments tested in FIG. 2 and conserves most of the hydrophilic residues in the laminin-1 GD6 peptide that could mediate protein—protein interactions. This sequence also overlaps with a region identified in a screen of amino-terminal TSP1 peptides as having heparin-independent adhesive activity (Clezardin et al., 1997). A synthetic peptide containing this TSP1 sequence (peptide 678) had strong adhesive activity for MDA-MB-435 cells (FIG. 3A). Spreading of two breast carcinoma cell lines on this peptide, laminin peptide GD6, and TSP1 were enhanced in the presence of the β1 integrin-activating antibody TS2/16 (FIG. 3B). It has been found that IGF1 strongly stimulated β1-integrin-mediated adhesion to TSP1 (Chandrasekaran et al., 1999). IGF1 similarly stimulated spreading of MDA-MB-435 cells on the TSP1 peptide 678 and to the laminin peptide GD6 (FIG. 3B).

Figure 4A:
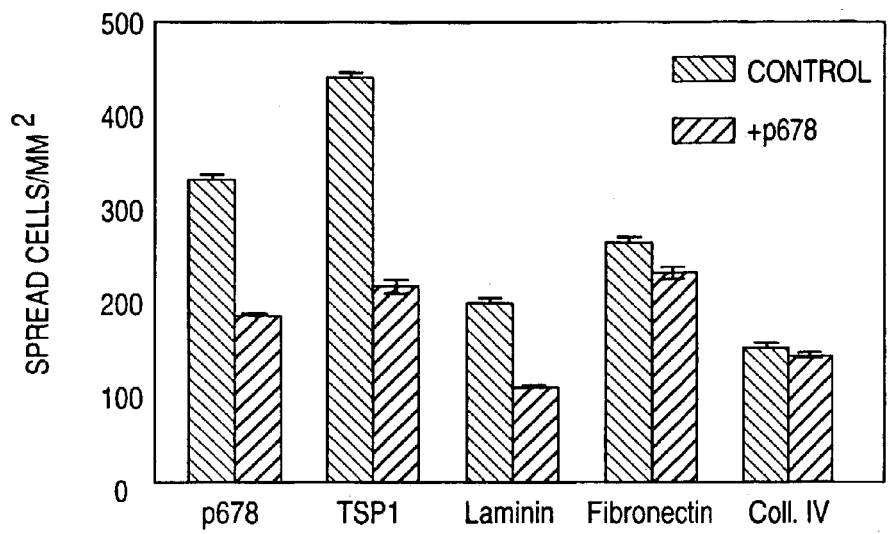
FIGS. 4A and 4B are graphs illustrating the inhibition of breast carcinoma cell spreading on matrix proteins by peptide 678. Panel A: MDA-MB-435 cell spreading was determined in the absence (solid bars) or presence of 10 μM TSP1 peptide 678 (striped bars) on substrates coated with 10 μM peptide 678, 40 μg/ml TSP1, 10 μg/ml murine laminin-1, 10 μg/ml human plasma fibronectin, or 10 μg/ml type IV collagen. Cell spreading is presented as mean±SD, n=3. Panel B: Inhibition of MDA-MB-435 cell attachment to surfaces coated with 10 μM peptide 678 (●) or laminin peptide GD6 (○) was measured in the presence of the indicated concentrations of peptide 678 added in solution.
Figure 4B:
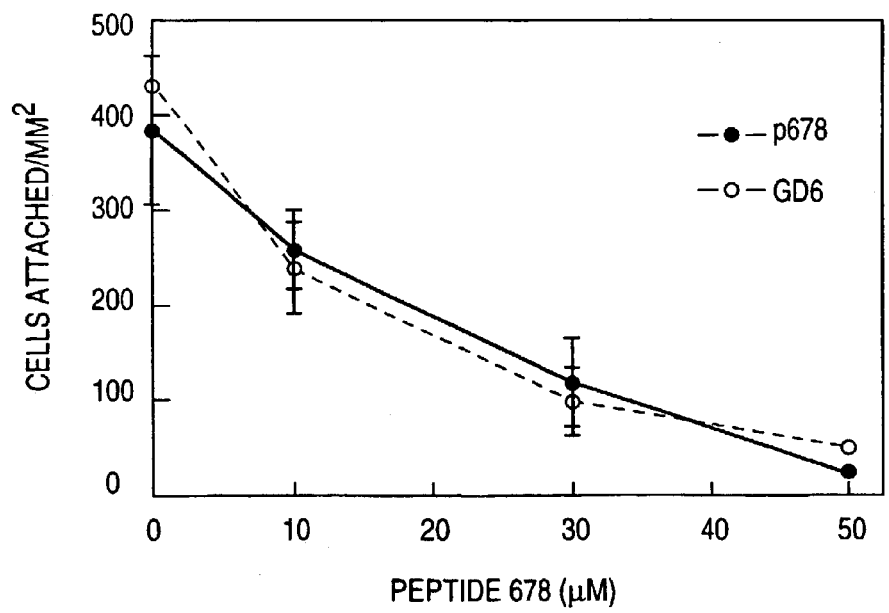

The TSP1 peptide 678 strongly inhibited spreading of MDA-MB-435 cells on TSP1 and murine EHS tumor-derived laminin-1/entactin but did not inhibit spreading of the same cells on the α5β1 integrin ligand fibronectin or on type IV collagen (FIG. 4A). The TSP1 peptide in solution strongly inhibited MDA-MB-435 cell attachment to itself and to GD6 (FIG. 4B), a known α3β1 integrin binding peptide from murine laminin-1 (Gehlsen et al., 1992). In contrast, the laminin peptide was a relatively weak inhibitor of adhesion to either peptide or TSP1 when tested in solution (IC50=700 μM, data not shown).

Figure 5A:
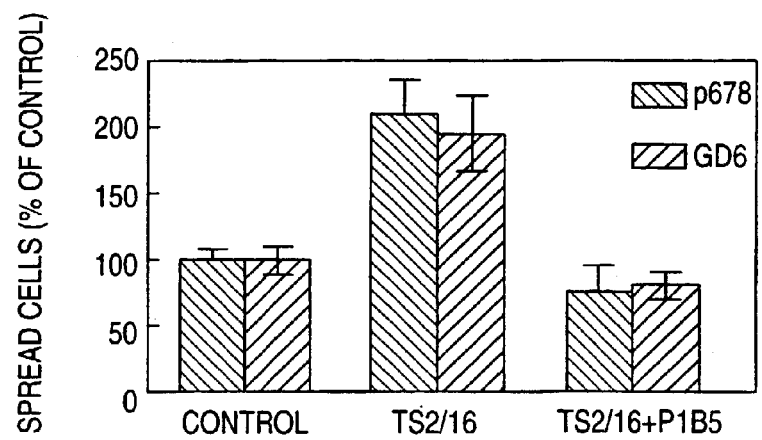
FIGS. 5A, 5B and 5C are graphs illustrating α3β1 integrin mediated adhesion to TSP1 peptide 678 and laminin-1 peptide GD6. Panel A: MDA-MB-435 cell spreading on TSP1 peptide 678 (solid bars) or laminin-1 peptide GD6 (striped bars) was determined with no additions (control) or in the presence of 5 μg/ml of β1-integrin antibody TS2/16 or in the presence of 5 μg/ml each of antibody TS2/16 and the α3β1-blocking antibody P1B5. Results are normalized to the control and are presented as mean±SD, n=3. Panel B: MDA-MB-435 cell spreading on substrates coated with 10 μM TSP1 peptide 678 (solid bars), 5 μM laminin-1 peptide GD6 (striped bars), or 5 μg/ml type I collagen (gray bars) was determined in the presence of 5 μg/ml of the α2β1 blocking antibody 6D7 (anti-α2) or the α3β1 blocking antibody P1B5 (anti-α3). Results are normalized to untreated controls and presented as mean±SD, n=3. Panel C: Divalent cation dependence for adhesion on TSP1 peptide 678 and intact TSP1. MDA-MB-435 cells were suspended in calcium-free Hams F12(K) medium containing 2 mM magnesium and the indicated concentrations of divalent cations or 2.5 mM EDTA. Cell spreading on substrates coated with 5 μM peptide 678 (solid bars) or 40 μg/ml TSP1 (striped bars) was determined in the absence or presence of 5 μg/ml of the β1 integrin activating antibody TS2/16.
Figure 5B:
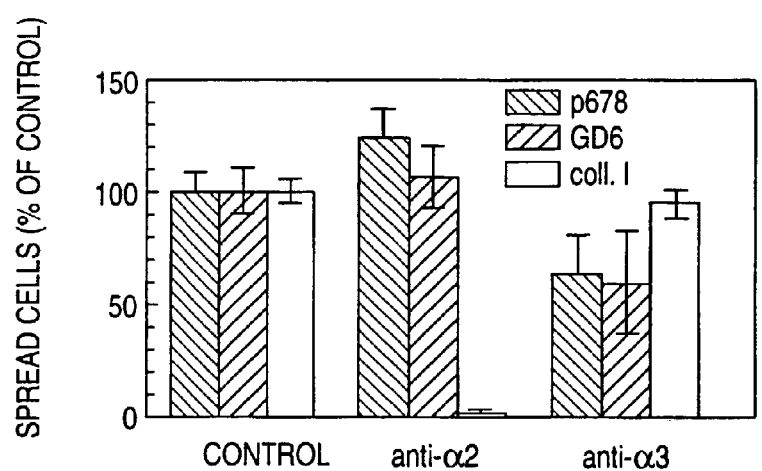

To verify that the TSP1 peptide 678 contains an α3β1 integrin recognition sequence, integrin α-subunit antibodies were tested for blocking adhesion to the peptide (FIG. 5). The α3-specific blocking antibody P1B5, which were shown to inhibit adhesion of the same cells to intact TSP1 (Chandrasekaran et al., 1999), partially inhibited adhesion of MDA-MB-435 cells on peptide 678 and completely reversed the enhancement of MDA-MB-435 cell adhesion to the same peptide stimulated by the β1 integrin-activating antibody TS2/16. In a further control experiment, the α2β1 blocking antibody 6D7 inhibited adhesion of MDA-MB-435 cells to type I collagen but not to peptide 678 (FIG. 5B). Function blocking antibodies for α4β1 and α5β1 integrins also had no effect on adhesion to peptide 678 (data not shown). Therefore, the peptide does not support adhesion mediated by α4β1 or α5β1 integrins nor inhibit adhesion to other integrin ligands.

Figure 5C:
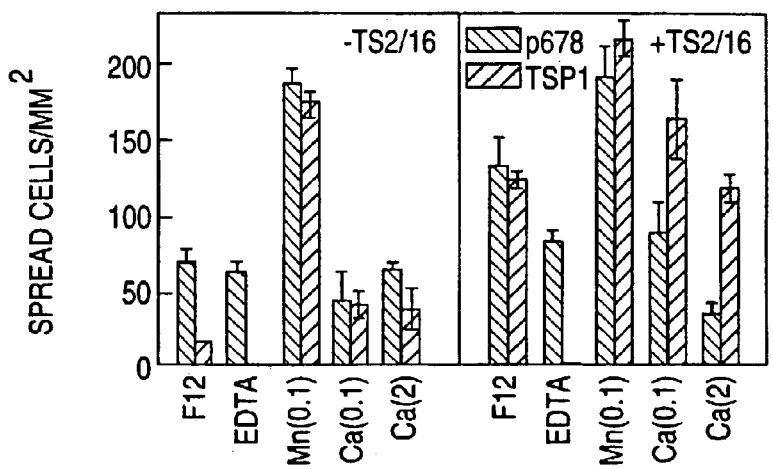

Divalent cation-dependence is also characteristic for binding of integrin ligands. Although $Mn^{2+}$ but not $Ca^{2+}$ induced the expected increase in MDA-MB-435 cell spreading on TSP1 peptide 678 and intact TSP1 (FIG. 5C), addition of EDTA only minimally inhibited basal spreading on peptide 678. EDTA completely inhibited the spreading on TSP1 observed in medium containing $Mg^{2+}$ as the sole divalent cation, although it did not inhibit cell attachment on TSP1 (FIG. 5C and results not shown). This residual adhesion probably results from the significant contribution of proteoglycans to adhesion of MDA-MB-435 cells on TSP1 (Chandrasekaran et al., 1999). Spreading on peptide 678 with $Mg^{2+}$ as the divalent cation became partially sensitive to EDTA, however, in the presence of the β1-activating antibody TS2/16. Addition of $Mn^{2+}$ further stimulated spreading on peptide 678 and intact TSP1 in the presence of TS2/16, but addition of $Ca^{2+}$ produced a dose-dependent inhibition of spreading on both substrates. Specific inhibition by $Ca^{2+}$ is consistent with previous data for the α3β1 integrin (Weitzman et al., 1993). These results suggest that integrin binding to peptide 678 is partially independent of divalent cations, but MDA-MB-435 cell spreading on this peptide may involve both α3β1 integrin binding and divalent cation-independent interactions with another cell surface molecule.

Figure 6:
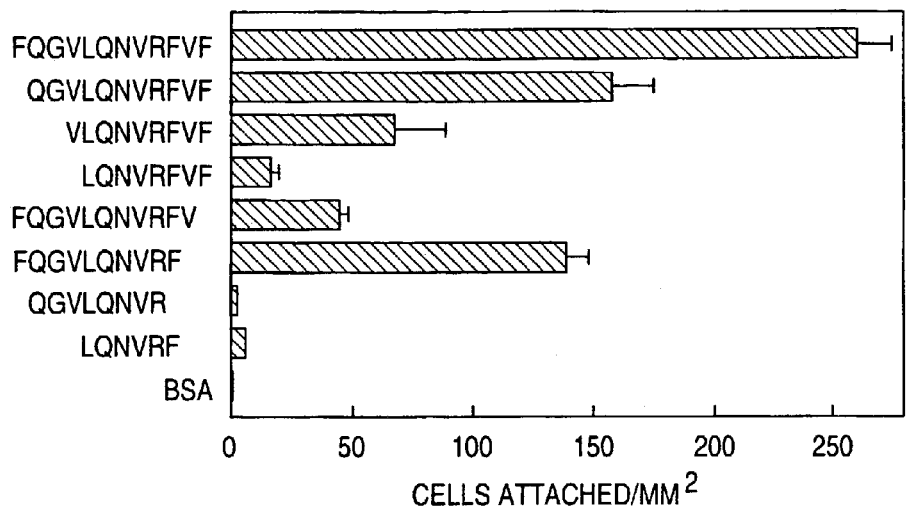
FIG. 6 is a histogram showing the determination of the minimal active TSP1 sequence to promote breast carcinoma cell adhesion. MDA-MB-435 cell adhesion was determined to polystyrene coated with 10 μM of the indicated TSP1 peptides (SEQ ID NOS:6, 31, 41, 40, 30, 32, 39 and 56, respectively) or with bovine serum albumin (BSA). Cell attachment is presented as the mean±SD for triplicate determinations.

Truncated peptides that contained portions of peptide 678 were synthesized to identify essential residues (FIG. 6). Truncation of the N-terminal Phe or the C-terminal Val-Phe only moderately decreased adhesive activity, but further truncations from either end of the peptide greatly diminished its activity. Inhibition assays confirmed that the loss of adhesive activity reflected loss of integrin binding rather than loss of ability to adsorb on the substrate (Table 2).

TABLE 2

Inhibition of MDA-MB-435 cell adhesion to immobilized peptide 678 by peptide analogs of TSP1 as well as direct adhesion of immobilized peptide analogs to MDA-MB-435 cells. Mean doses to achieve 50% inhibition of control adhesion ($IC_{50}$) to polystyrene coated with 5 μM peptide 678 were determined from at least three independent experiments, each performed in triplicate. Peptides were tested at up to 300 μM or to the solubility limit for each peptide where lower limits for inhibitory activity are indicated.

| # | Sequence (SEQ ID NO:) | MW | Source | Inhibition of peptide 678 ($IC_{50}$) | Direct adhesion# |
|---|---|---|---|---|---|
| 674 | GEFYFDLRLKGDKY (37) | 1751 | type IV coll. | | |
| 675 | KQNCLSSRASFRGCVRNLRLSR (8) | 2552 | laminin GD6 | | +++ |
| 678 | FQGVLQNVRFVF (6) | 1454 | TSP1 | 3.5((15)) | +++ |
| 679 | FRGCVRNLRLSR (12) | 1477 | part of GD6 | ((700)) | +++ |
| 681 | ac-LQNVRF-am (38) | 815 | part of 678 | 500 | − |
| 682 | FQGVLQNVRF (32) | 1207 | | 6 | ++ |
| 683 | QGVLQNVR (39) | 913 | | >300 | − |
| 685 | QGVLQNVRFVF (31) | 1307 | | 24 | ++ |
| 684 | LQNVRFVF (40) | 1022 | | 300 | +/− |
| 688 | VLQNVRFVF (41) | 1121 | | >100 | + |
| 689 | FQGVLQNVRFV (30) | 1307 | | + | + |
| 686 | FQGVLQAVRFVF (10) | 1411 | | >300 | ++ |
| 687 | FQGVLANVRFVF (29) | 1397 | | 3 | ++ |
| 690 | FQGVLQNVAFVF (11) | 1369 | | >300 | − |
| 691 | FQGVLQNARFVF (42) | 1426 | | >300 | ++ |
| 692 | FQGVLQNVRAVF (43) | 1378 | | 18 | ++ |
| 693 | FQGVLQNVRFVA (28) | 1378 | | 27 | ++ |
| 694 | FQGVLQNVHFVF (44) | 1435 | | 54 | +/− |
| 695 | FQGVAQNVRFVF (27) | 1412 | | 5 | ++ |
| 696 | FAGVLQNVRFVF (26) | 1397 | | 1.8((12)) | ++ |
| 697 | AQGVLQNVRFVF (25) | 1378 | | 5 | ++ |
| 698 | FQGVLNNVRFVF (24) | 1440 | | 3 | ++ |
| 701 | TPGQVRTLWHDP (7) | 1407 | (part of C6) | >300 | − |
| 702 | FQGVLQNVKFVF (23) | 1426 | | 6((25)) | +++ |
| 703 | FQGVLQNVQFVF (45) | 1426 | | >100((300)) | +/− |
| 704 | acQGVLQNVRF (22) | 1060 | | 15((~100)) | ++ |
| 705 | FQGVLQSVRFVF (21) | 1427 | | ((15)) | ++ |
| 709 | D reverse-678 (—) | | | ((18)) | |
| 716** | carboxamidomethyl-thioproprionyl-FQGVLQNVRFVF (46) | 1538 | | ((100)) | |
| 717 | FQGVLQQVRFVF (20) | 1468 | | ((30)) | |
| 718 | FQGVLQDVRFVF (19) | 1455 | | ((12)) | |
| 719 | FQGVLQNLRFVF (18) | 1468 | | ((16)) | |

*Inhibition constants ($IC_{50}$) were determined by microscopic adhesion assays except where indicated by (( )) in which case the inhibition constants were determined by the hexosaminidase hexosaminidase method.
Activity to promote MDA-MB-435 cell adhesion in a direct adhesion assay using peptides adsorbed on polystyrene.

Figure 7:
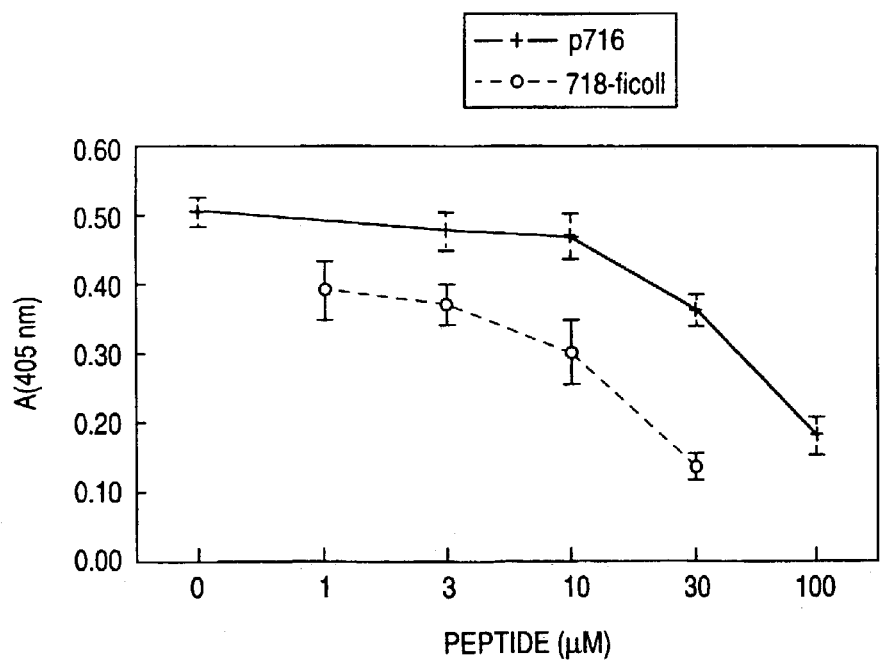
FIG. 7 displays the inhibition of MDA-MB-435 cell adhesion by free and conjugated TSP1 peptide analogs. MDA-MB-435 cell adhesion to microliter plate wells coated with 5 uM peptide 678 was determined in the presence of the indicated concentrations of soluble carboxamidomethyl-peptide 716 or peptide 716 covalently linked to FICOLL™ as previously described (Guo et al., 1997). After washing twice to remove unattached cells, adherent cells were quantified by detection of cellular hexosaminidase using p-nitrophenyl-N-acetylglucosaminide as substrate. Released p-nitrophenol was detected by absorbance at 405 nm. Results are mean +/−SD, n=3.

When peptide 716 is conjugated to FICOLL™, its inhibition of adhesion of MDA-MB-435 breast cell to peptide 678 is enhanced compared to the unconjugated or free peptide 716. This is shown in FIG. 7. In this case, the adherent cells are quantified by detection of cellular hexosaminidase using p-nitrophenyl-N-acetylglucosaminidine as substrate. Released p-nitrophenol is detected by absorbance at 405 nm.

As found in the direct adhesion assays, peptides without the N-terminal Phe or the C-terminal Val-Phe retained significant inhibitory activities, but all shorter peptides were weak inhibitors or inactive. These results imply that the integrin recognizes an extended sequence, but this approach could not discriminate conformational effects of flanking sequences from a direct contribution to integrin binding.

Figure 8:
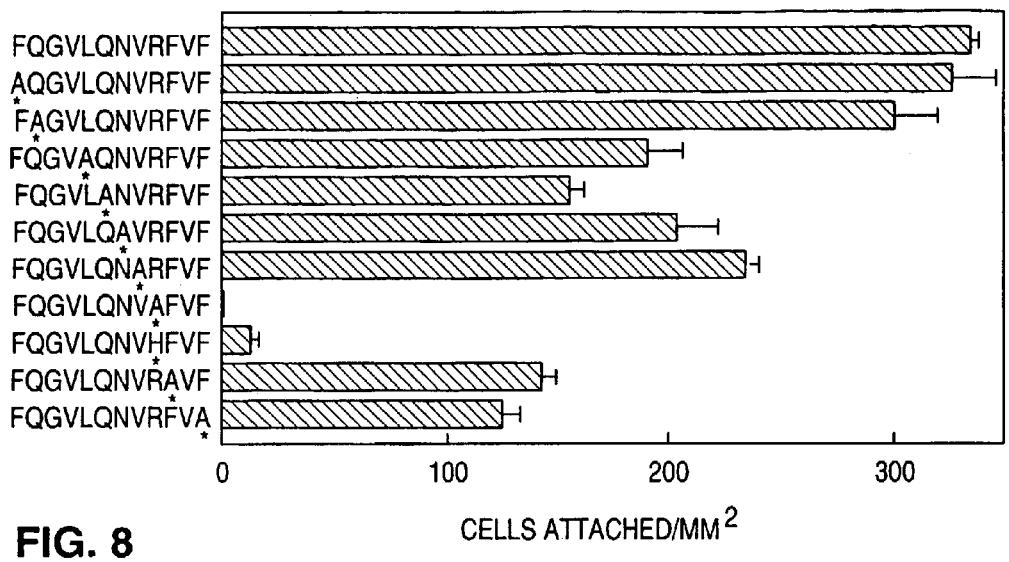
FIG. 8 is a histogram showing the effect of systematic substitution of Ala residues on adhesive activities of the TSP1 sequence 190–201 (SEQ ID NOS:6, 25, 26, 27, 29, 10, 42, 11, 44, 43 and 28, respectively) for breast carcinoma cells. Cell attachment was determined to substrates coated with each peptide at 10 μM and is presented as mean±SD, n=3. Residues substituted in the native TSP1 sequence are indicated with an asterisk.

To better define those residues involved in α3β1 integrin binding, Ala residues were sytsematically substituted into the peptide 678 and each peptide was tested for adhesive activity (FIG. 8). Based on the complete loss of adhesion activity for MDA-MB-435 cells following its substitution, only Arg(198) was essential for adhesive activity of peptide 678 (FIG. 8). Replacement of Arg(198) with a His also dramatically reduced adhesive activity. Ala substitutions at several other positions significantly decreased adhesive activity, except for the two N-terminal residues, which only slightly decreased adhesive activity.

Although only the Arg residue was essential for direct adhesion, substitution of several additional residues with Ala markedly decreased or abolished inhibitory activity of the respective soluble peptides in solution to block α3β1-dependent adhesion to immobilized peptide 678 (Table 3).

TABLE 3

Mapping of essential residues for inhibition of MDA-MB-435 cell adhesion to immobilized peptide 678.
Mean doses to achieve 50% inhibition of control adhesion to 5 μM peptide 678 ($IC_{50}$) were determined from at least three independent experiments, each performed in triplicate. Residues substituted in the native TSP1 sequence are underlined. substituted in the native TSP1 sequence are underlined.

| Peptide | Sequence | SEQ ID NO: | $IC_{50}$ (μM) |
| --- | --- | --- | --- |
| 678 | FQGVLQNVRFVF (TSP1) | 6 | 3.5 |
| 697 | AQGVLQNVRFVF | 25 | 5 |
| 696 | FAGVLQNVRFVF | 26 | 1.8 |
| 695 | FQGVAQNVRFVF | 27 | 5 |
| 687 | FQGVLANVRFVF | 29 | 3 |
| 686 | FQGVLQAVRFVF | 10 | >300 |
| 691 | FQGVLQNARFVF | 42 | >300 |
| 690 | FQGVLQNVAFVF | 11 | >300 |
| 702 | FQGVLQNVKFVF | 23 | 6 |
| 694 | FQGVLQNVHFVF | 44 | 54 |
| 703 | FQGVLQNVQFVF | 45 | >100 |
| 692 | FQGVLQNVRAVF | 43 | 18 |
| 693 | FQGVLQNVRFVA | 28 | 27 |

These experiments showed that Arg(198), Val(197), and Asn(196) are essential for inhibitory activity of the peptides in solution. Substitution of Phe(199) and Phe(201) decreased the inhibitory activities of the respective peptides 5- to 8-fold, indicating that these flanking residues also contribute to activity of the peptides in solution. In contrast, peptides with Ala substitutions at 4 of the 6 N-terminal residues in this sequence had inhibitory activities equivalent to that of the native TSP1 sequence. Therefore, NVR is the essential sequence for binding to the α3β1 integrin, but flanking residues may be necessary for inducing the proper conformation of this minimal sequence in peptide 678.

The specificity for an Arg residue at position 198 was further examined using conservative amino acid substitutions (Table 3). Substitution with Lys decreased activity approximately 2-fold, whereas substitution with Gln, to retain hydrogen-bonding ability while removing the positive charge, abolished the inhibitory activity. A His substitution showed intermediate activity, indicating that a positive charge rather than a large side chain with hydrogen bonding ability is required at this position.

Figures 9A, 9B:
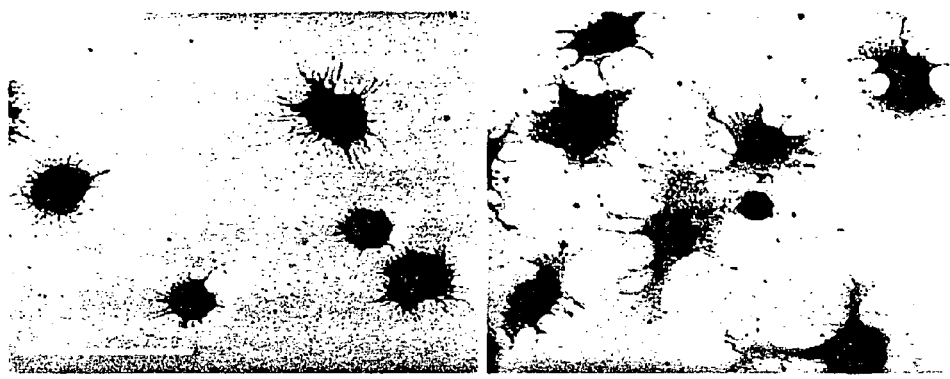
FIG. 9 shows the morphology of MDA-MB-435 cells attaching on TSP1 peptide 678. Panel a: Direct adhesion on TSP1 peptide 678 stimulates formation of filopodia (bar=50 μm). Panel b: IGF1 stimulates increased spreading with formation of lamellipodia. Panel c: Staining of F-actin using BODIPY TR-X phallacidin (bar=20 μm). Panel d: Double labeling of the field in panel C with anti-vinculin antibody. Panel e: Immunolocalization of β1 integrin subunits in cells attached on peptide 678 using antibody TS2/16 (bar=10 μm). Panel f: immunolocalization of α3 integrin subunits using antibody P1B5.
Figures 9C, 9D:
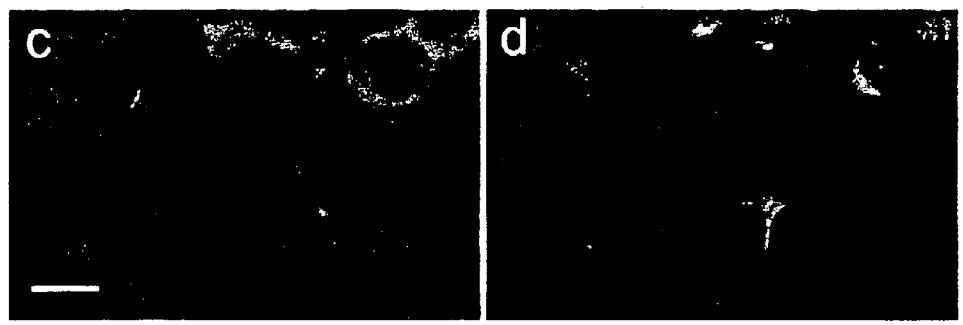
Figures 9E, 9F:
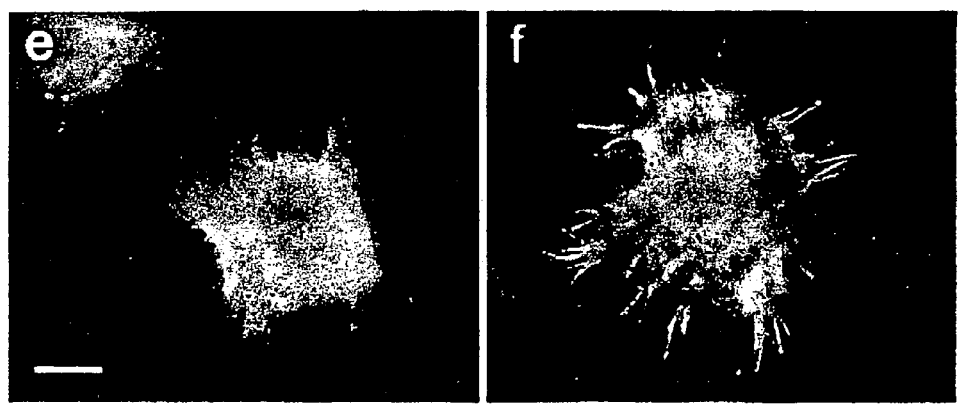

The active peptides strongly promoted formation of filopodia in MDA-MB-435 cells (FIG. 9a) similar to those induced by attachment on intact TSP1 (Chandrasekaran et al., 1999). Addition of IGF1 enhanced spreading and increased formation of lamellipodia on the same peptide (FIG. 9b). Phallacidin staining demonstrated organization of F-actin at the cell periphery but no organization of stress fibers across the cell body (FIG. 9c). Using antibodies recognizing vinculin (FIG. 9d) and focal adhesion kinase (data not shown) as markers of focal adhesion formation, no induction of focal adhesions in MDA-MB-435 cells attaching on these peptides could be detected, although the same markers showed typical focal adhesion staining patterns in the cells when attaching on vitronectin or fibronectin substrates (results not shown). Staining for the α3β1 integrin was punctate and prominently localized in filopodia extended by MDA-MB-435 cells on immobilized peptide 678 (FIG. 9f), whereas total β1 integrin staining was more diffuse and concentrated over the cell body.

Figure 10A:
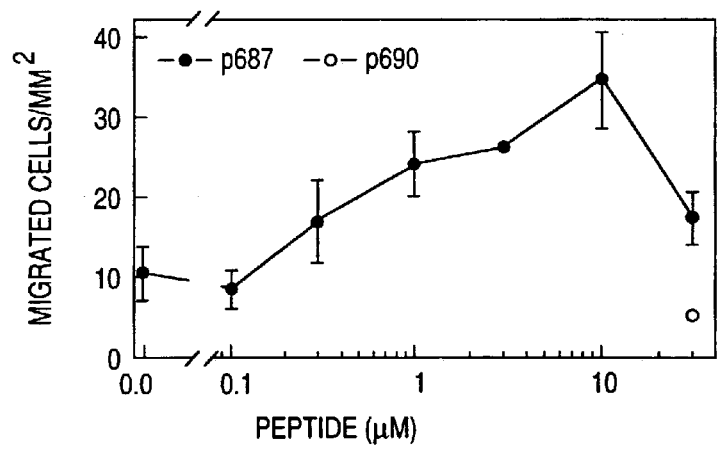
FIGS. 10A and 10B display the measurement of MDA-MB-435 cell chemotaxis. Panel A: Dose-dependence for stimulation of MDA-MB-435 cell motility by peptide 678 added to the lower well of a modified Boyden chamber. Cells migrated to the lower surface of an 8 μm pore polycarbonate filter were quantified microscopically after 7 h, mean±SD, n=3 for a representative experiment. Panel B: MDA-MB-435 cell chemotaxis was measured to medium alone (blank), to 10 μM TSP1 peptide 678, or to 10 μM of the inactive analog peptide 690 added to the lower chamber. Chemotaxis of untreated cells (striped bars) or cells treated with 10 nM IGF1 in the upper chamber (solid bars) was determined after 7 h and is presented as mean±S.D., n=3.
Figure 10B:
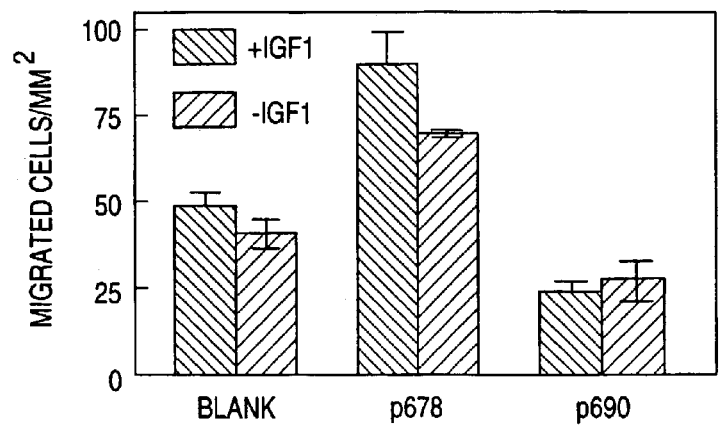

TSP1 stimulates chemotaxis of MDA-MB-435 cells, and this response is inhibited by the α3β1 blocking antibody P1B5 (Chandrasekaran et al., 1999). Peptide 678 also stimulated chemotaxis of MDA-MB-435 cells (FIG. 10). Chemotaxis to peptide 678 was dose dependent with a maximal response at 10 μM (FIG. 10A). This response was specific in that peptide 690 was inactive. In agreement with the observations that IGF1 stimulated β1 integrin-dependent chemotaxis of MDA-MB-435 cells to TSP1 (Chandrasekaran et al., 1999) and adhesion of the same cells to peptide 678 (FIGS. 3 and 9), the chemotactic response of MDA-MB-435 cells to peptide 678, but not to peptide 690, was increased in the presence of IGF1 (FIG. 10B).

Based on examination of synthetic peptides and recombinant fragments representing approximately 90% of the TSP1 sequence, only the sequence FQGVLQNVRFVF (SEQ ID NO:6) from the amino terminal domain exhibited activities that are expected for an α3β1 integrin binding sequence in TSP1. A recombinant fragment of TSP1 containing this sequence also promoted β1 integrin-dependent adhesion. In solution, this peptide specifically inhibited adhesion to TSP1 but not to ligands recognized by other integrins. Adhesion to this peptide and to TSP1 was stimulated by IGF1 receptor ligands that stimulate integrin-dependent adhesion to intact TSP1, by $Mn^{2+}$, and by a β1 integrin-activating antibody and partially inhibited by an α3β1 function blocking antibody. Based on systematic amino acid substitutions in the active sequence, NVR appears to be the essential core sequence in this TSP1 peptide for recognition by the α3β1 integrin.

Adhesive activities of the immobilized peptides imply that only Arg(198) may directly participate in this interaction, although the partial resistance to inhibition by an α3β1 integrin antibody and EDTA suggest that the peptides with Arg may also support adhesion independent of integrin binding. The context surrounding the Arg is important, however, because other peptides with similar sequences (such as peptide 701 with a QVRT (SEQ ID NO:47) sequence) had no activity, and Ala substitutions of the flanking residues in peptide 678 eliminated or markedly decreased its inhibitory activity in solution. The essential amino acid residues are completely conserved in human, murine, bovine, and Xenopus TSP1, although in chicken TSP1 a His replaces the Arg. A similar motif is found in murine and human TSP2, with a His residue replacing the Arg. As a free peptide the TSP1 sequence with a His substitution was much less active, so it is not clear whether the TSP2 sequence could be recognized by α3β1 integrin. Activity of the latter sequence may be increased in an environment that increases protonation of the imidazole in His.

A consensus α3β1 integrin recognition sequence in α3β1 ligands has not been reported. One hypothesis is that different ligands have unrelated binding sequences, which is supported by a recent mutagenesis study (Krukonis et al., 1998). However, other recent data has raised questions about whether all of the proteins reported to mediate α3β1-dependent adhesion are true α3β1 ligands (Krukonis et al., 1998). LamA2 and LamA3 were verified to bind α3β1 integrin and have potential binding motifs based on the data, but human LamA1, which was found not to bind α3β1 with high avidity, has an Ala in the position occupied by the essential Arg in the TSP1 sequence. Substitution of Ala for the Arg in the TSP1 sequence abolished all activity of the synthetic TSP1 peptide. Although RGD was reported to be an α3β1 ligand, the RGD in entactin is not required for recognition. A binding site for the α3β1 integrin in entactin was mapped to the G2 domain (residues 301–647) (Gresham et al., 1996). Multiple alignment of this region of entactin against the TSP1 sequence and the murine laminin-1 peptide GD6 identified a related sequence FSGIDEHGHLTI (SEQ ID NO:48), but this sequence lacks any of the essential residues in the TSP1 sequence. This domain of entactin also contains two NXR sequences: NNRH (SEQ ID NO:49) and NGRQ (SEQ ID NO:50). It remains to be determined whether either of these can function as an α3β1 integrin recognition sequence.

The absence of an Asp residue in peptide 678 may account for its partial independence of divalent cations. An Asp residue is usually considered an essential element for integrin peptide ligands (Aota et al., 1995; Ruoslahti, 1996). According to one model for integrin ligand binding, the divalent cation participates directly in binding an Asp-containing peptide ligand (reviewed in (Fernandez et al., 1998). Thus an integrin peptide ligand without a carboxyl side chain can not coordinate with a bound divalent cation and therefore may not have a divalent cation requirement for binding to the integrin. The alternate model, proposing an indirect role of divalent cations in integrin activation (Fernandez et al., 1998), would be consistent with the observed stimulation of cell spreading on peptide 678 by Mn2+ but not Ca2+ and the partial inhibition following chelation of divalent cations.

Another interpretation of the partial divalent cation-independence for the adhesive activity of peptide 678 is that ionic interactions of the Arg side chain in the TSP1 peptide with the negatively charged cell surface contribute to the adhesive activity of this peptide. Weak ionic interactions could promote adhesion to the immobilized peptide through multivalent interactions with negatively charged glycoproteins and proteoglycans on the cell but would not significantly contribute to binding of the same monovalent peptide to the cell in solution. This hypothesis would explain why the Arg-containing peptides 686 and 691, in which the essential Val or Asn residues were substituted with Ala, lacked activity in solution to inhibit adhesion to α3β1 ligands but retained some adhesive activity when immobilized. Thus, inhibitory activities in solution may provide a more reliable assessment of integrin binding specificity for Arg-containing peptides.

Spreading of MDA-MB-435 breast carcinoma cells on intact TSP1 (Chandrasekaran et al., 1999) or the α3β1 integrin binding peptide 678 induces formation of filopodia. In cells plated on peptide 678, these structures are enriched in the α3 integrin subunit, suggesting that engagement of this integrin by TSP1 triggers formation of filopodia. Formation of filopodia or microspikes have been noted during attachment of other cell types on TSP1 (Adams, 1995). This response may be mediated by the α3β1 integrin, because lamellar spreading rather than formation of filopodia was typically observed on melanoma cells that predominantly use the αvβ3 integrin receptor for spreading on TSP12.

Using multiple sequence alignment, the N-terminal domains of thrombospondins were recently shown to contain a module related to pentraxins and to the G domain modules of laminins (Beckmann et al., 1998). Based on this alignment, both the α3β1 integrin-binding sequence from TSP1 identified here and the GD6 sequence of laminin are located at the C-terminus of a pentraxin module. The known three dimensional structures of other members of the same superfamily (Shrive et al., 1996) predict that both potential integrin binding sequences are located in the last β-strand of a pentraxin module and, therefore, may be presented with similar topologies on the laminin G domain and the N-terminal domain of TSP1. This observation suggests an evolutionary relationship between the thrombospondin N-terminal domains and laminin G domains that is consistent with their proposed common function as recognition sites for a β1 integrin receptor.

Example 3

Recognition of α3β1 Integrin-Binding Sequence from TSP1 by Endothelial Cells and SCLC and Modulation of SCLC and Endothelial Cell Behavior and Angiogenesis by α3β1 I Integrin-Binding Peptides from Thrombospondin-1

Figure 11A:
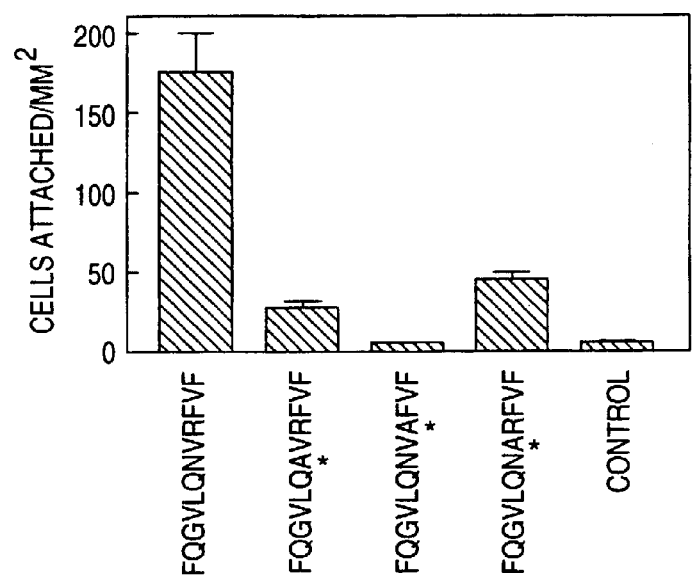
FIGS. 11A and 11B display adhesion of endothelial cells on an α3β1 integrin-binding peptide from TSP1. Panel A: TSP1 peptide 678 (FQGVLQNVRFVF; SEQ ID NO:6) or analogs of this peptide with the indicated Ala substitutions (*) were adsorbed on bacteriological polystyrene substrates at 10 μM in PBS. Direct adhesion of BAE cells to the adsorbed peptides or uncoated substrate (control) are presented as mean±SD, n=3. Panel B: Loss of cell—cell contact stimulates endothelial cell spreading on TSP1. Two flasks of BAE cells were grown to confluence. One flask was harvested and replated in fresh medium at 25% confluency. Fresh medium was added at the same time to the second flask. After 16 h, cells from both flasks were dissociated using EDTA and adhesion was measured on substrates coated with 40 μg/ml TSP1, 10 μg/ml vitronectin, 20 μg/ml plasma fibronectin, or 5 μg/ml type I collagen. The percent spread cells after 60 min is presented as mean±SD, n=3 for a representative experiment.

Adhesion assays were used to determine whether the α3β1 integrin-binding sequence from TSP1 is recognized by endothelial cells. Endothelial cells attached specifically on immobilized TSP1 peptide 678 but not on the inactive analog peptide 690 (FIG. 11A). Two related peptides with amino acid substitutions that diminished their activity for mediating α3β1-dependent adhesion of breast carcinoma cells (Chandrasekaran et al., 1999) only weakly supported endothelial cell adhesion (FIG. 11A). All of the peptides had similar capacities for adsorption on the polystyrene substrate used for these assays (2.5 to 3.8 pmoles/mm$^2$), so the differences in activities of these peptides did not result from differences in their adsorption.

Proliferation of Endothelial Cells

Figure 11B:
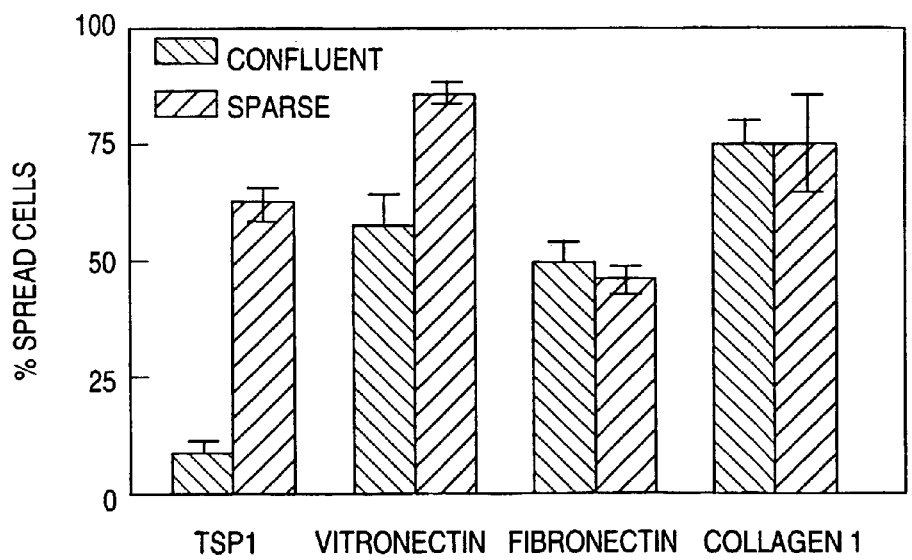

Although some previous publications have reported that TSP1 promotes spreading of endothelial cells (Taraboletti et al., 1990; Morandi et al., 1993), other investigators have concluded that TSP1 can not promote endothelial cell spreading and disrupts spreading of endothelial cells attached on certain other matrix proteins (Lawler et al., 1988; Lahav, 1988; Murphy-Ullrich et al., 1989; Chen et al., 1996). In agreement with the latter reports, bovine aortic endothelial cells harvested from a confluent cobblestone did not spread on TSP1(FIG. 11B and FIG. 12A). However, when a duplicate culture of the same cells was replated at low density to minimize cell—cell contact and harvested at the same time post feeding, they did (FIG. 11B and FIG. 12C). Up-regulation of spreading on TSP1 following loss of cell—cell contact was specific for TSP1, because fibronectin and collagen spreading were not induced under the same conditions (FIG. 11B and FIG. 12B, D). Sparse cells displayed some increase in spreading on vitronectin, although approximately 60% of the cells harvested from a confluent monolayer also spread on vitronectin, compared to less than 10% on TSP1.

Figure 13A:
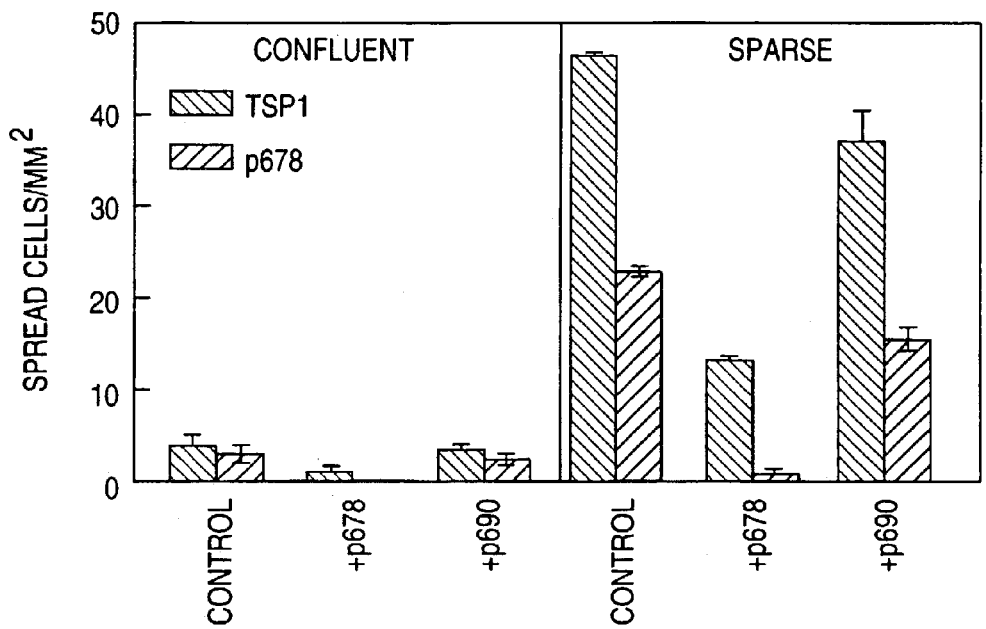
FIGS. 13A and 13B display endothelial cell spreading on TSP1 peptide 678. Loss of cell—cell contact induces endothelial cell spreading on TSP1 peptide 678. Panel A: Adhesion of sparse or confluent BAE cells to substrates coated with 40 μg/ml TSP1 (solid bars) or 10 μM TSP1 peptide 678 (striped bars) was determined as in FIG. 1B. Spreading was determined microscopically for cells with no additions, in the presence of 10 μM peptide 678, or in the presence of 30 μM of the control peptide 690. Results are presented as mean±SD, n=3. Panel B: HDME cells harvested from confluent or sparse cultures as in FIG. 10 were plated on substrates coated with TSP1 (solid bars), peptide 678

Similar induction of BAE cell spreading following loss of cell—cell contact was observed using the TSP1 peptide 678 (FIG. 13A). Density-dependent spreading on intact TSP1 and the TSP1 peptide were both inhibited by peptide 678 added in solution but were not significantly inhibited by the control peptide 690 (FIG. 12E and FIG. 13A).

Inhibition by the peptide was specific for endothelial cell spreading on TSP1 or the TSP1 peptide, because peptide 678 did not inhibit spreading on fibronectin (FIG. 12F).

Figure 13B:
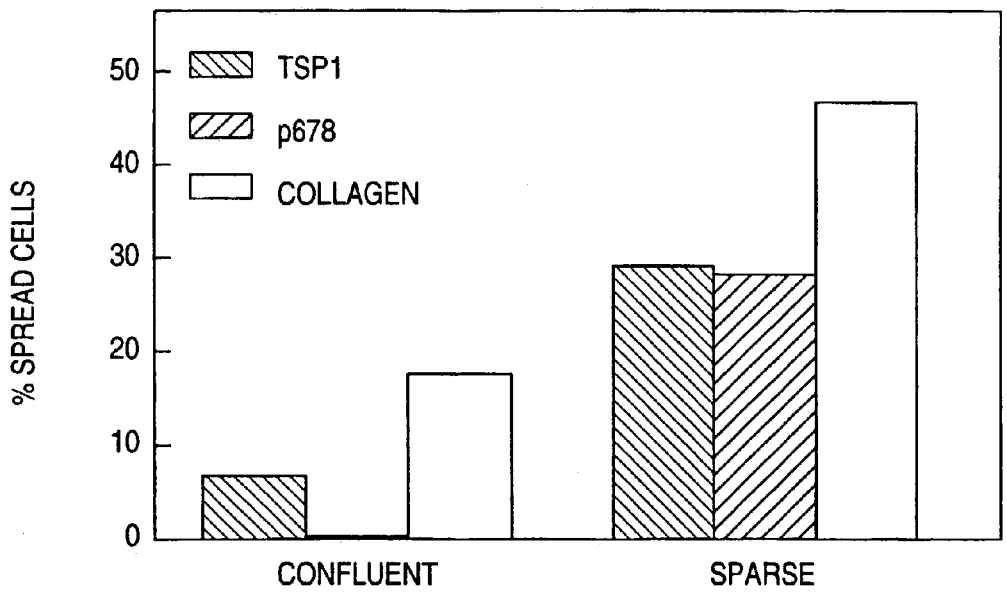

Similar density dependence for spreading on TSP1 and peptide 678 was observed with HDME cells (FIG. 13B). Although only 6% of HDME cells harvested from a confluent monolayer spread following attachment on immobilized TSP1, 29% of those from a duplicate sparse culture spread on the same substrate. No spreading of the confluent culture was detected on peptide 678, but 28% of HDME cells from the sparse culture spread on this peptide. Using HUVEC, sparse cultures showed only a slight increase in spreading (46±7% versus 41±5% for confluent cells), but spreading on the peptide 678 was significantly induced (12±3% for sparse cultures versus 3±1% for confluent, data not shown). These data demonstrate that loss of cell—cell contact induces spreading on TSP1 and its α3β1 integrin-binding peptide for both bovine and human endothelial cells.

The increased spreading of BAE cells on TSP1 is mediated at least in part by α3β1 integrin, because a TSP1 peptide that binds to this integrin inhibited spreading on TSP1 by 55% but did not inhibit spreading on fibronectin or vitronectin substrates (FIG. 14A). The αvβ3 integrin also plays some role in BAE cell spreading on TSP1, since the αv integrin antagonist SB223245 partially inhibited spreading on TSP1. The effect of these two inhibitors was additive, producing a 76% inhibition of spreading when combined. Similar results were obtained using the αvβ3 peptide antagonist GRGDSP (SEQ ID NO:9) alone and in combination with peptide 678. Approximately 20% of the spreading response on TSP1 was resistant to the GRGDSP (SEQ ID NO:9) peptide, but combining this peptide with the α3β1 binding peptide completely inhibited spreading on TSP1.

Primary human umbilical vein and dermal microvascular endothelial cells also showed similar role for the α3β1 integrin in spreading on TSP1 (FIG. 14B and results not shown). HUVEC spreading on TSP1 was inhibited 70±7% by peptide 678, whereas spreading on vitronectin was not significantly inhibited (FIG. 14B). Conversely, the αv antagonist SB223245 completely inhibited spreading on vitronectin but did not significantly inhibit spreading on TSP1. HDME cell spreading on TSP1 was partially inhibited by the function blocking integrin antibodies specific for β1 (mAb13) and α3 subunits (P1B5) but not by the α4β1 blocking antibody P4C2 (FIG. 14C), which verified that spreading of these cells on TSP1 is also mediated by α3β1 integrin.

The possible involvement of other TSP1 receptors, including αvβ3 integrin, CD36, and heparin sulfate proteoglycans, were also examined. The TSP1-binding integrin αvβ3 did not contribute to adhesion of the human endothelial cells, based on insensitivity to the αv integrin antagonist SB223245 (FIG. 14B and results not shown). Likewise, a function blocking antibody to the TSP1 receptor CD36 did not block adhesion of HDME cells (FIG. 14C). Of the human endothelial cells used, only HDME cells expressed CD36 as measured by RT-PCR (results not shown). Therefore, expression of CD36 is not required for endothelial cell spreading on TSP1. Heparin also had no effect on spreading of HDME cells on a TSP1 substrate (data not shown). These results demonstrate that α3β1 integrin contributes to spreading of several types of endothelial cells on TSP1 and are consistent with the previous report that HDME cell adhesion on TSP1 is independent of CD36 and the αvβ3 integrin (Chen et al., 1996)

Figure 15A:
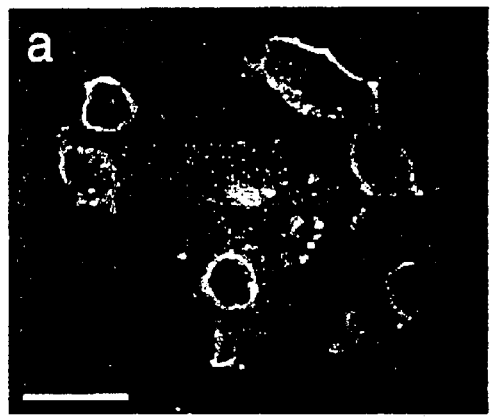
Figure 15B:
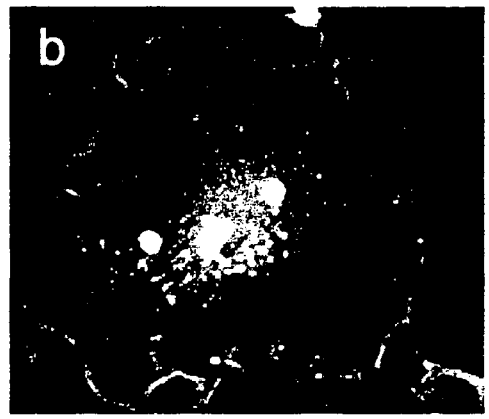
Figure 15C:
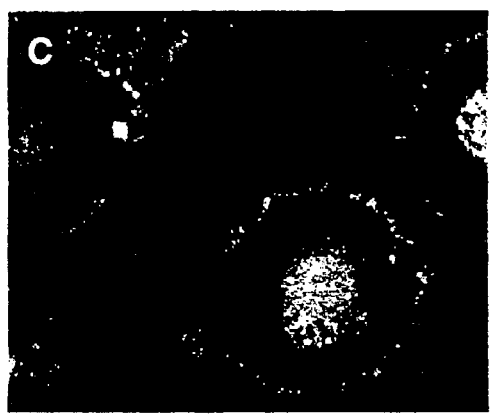
Figure 15D:
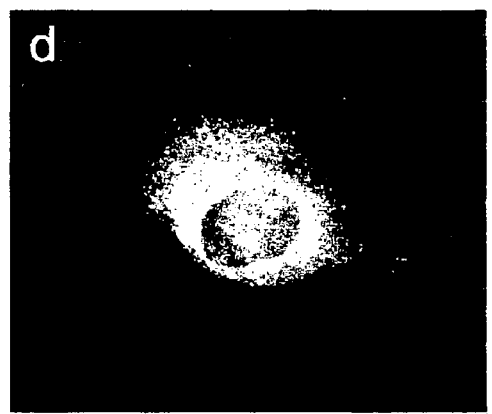
Figure 15E:
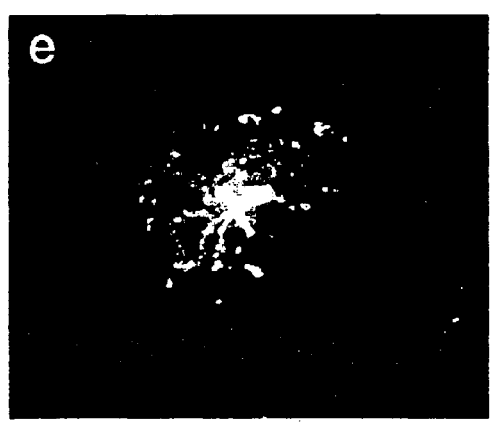
Figure 15F:
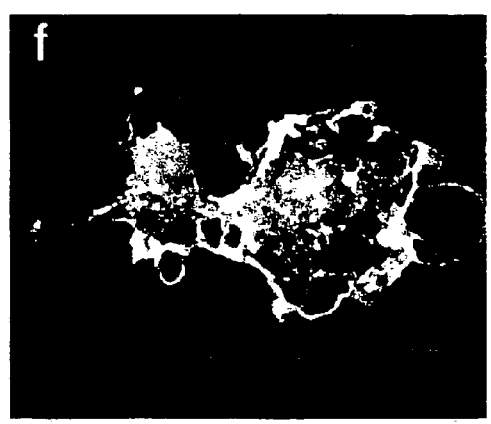

The α3β1 integrin was localized in lamellopodia of cells spreading on TSP1 (FIG. 15A). The β1 integrin activating protein CD98 showed a similar distribution in cells spreading on TSP1 (FIG. 15B). Lamellar spreading on TSP1 was associated with tyrosine phosphorylation at the leading edge (FIG. 15C). Vinculin antibody staining showed no evidence for formation of focal adhesions on TSP1, but some cells showed limited radial organization of vinculin in lamellopodia (FIG. 15D). These structures were not observed in cells stained with the α3β1 antibody and may therefore be induced by another TSP1 receptor, such as the αvβ3 integrin.

Cells spreading on peptide 678 also showed organization of α3β1 integrin (FIG. 15E) and CD98 (FIG. 15F) at the cell periphery, supporting their role in mediating spreading on this TSP1 peptide. However, the spreading observed on glass substrates coated with peptide 678 was consistently weaker than observed using the same peptide adsorbed on polystyrene, so immunofluorescent analysis of endothelial cells on this peptide was limited by lack of a suitable substrate.

Based on the organization of CD98 in endothelial cells spreading on TSP1 and its ability to activate β1 integrins (Fenczik et al., 1997; Chandrasekaran et al., 1999) the effect of the CD98 antibody 4F2 on HUVEC spreading on TSP1 was examined (FIG. 16). The CD98 antibody enhanced spreading on TSP1 and peptide 678 to a similar degree as the β1 integrin activating antibody TS2/16. Stimulation of spreading by both antibodies was specific in that spreading of the treated cells on vitronectin, an αvβ3 integrin ligand, was not affected (FIG. 16).

TSP1 specifically promotes adhesion of SCLC cells. Several SCLC lines were tested for adhesion on substrates coated with TSP1, laminin, or fibronectin (FIG. 17 and Table 4).

TABLE 4

SCLC cell adhesion to extracellular matrix proteins

| | | Concentration (µg/ml) | | | |
|---|---|---|---|---|---|
| Cell line | Substrate | 6.2 | 12.5 | 25 | 50 |
| H69 | TSP1 | 6 ± 1 | 46 ± 8 | 94 ± 6 | 110 ± 14 |
| | fibronectin | 1 ± 1 | 5 ± 1 | 13 ± 3 | 22 ± 7 |
| | laminin | 1 ± 1 | 16 ± 1 | 82 ± 8 | 108 ± 11 |
| H345 | TSP1 | 1 ± 1 | 7 ± 1 | 124 ± 17 | 165 ± 6 |
| | fibronectin | 0 | 6 ± 2 | 25 ± 5 | 17 ± 5 |
| | laminin | 6 ± 2 | 8 ± 1 | 151 ± 31 | 148 ± 9 |
| N417 | TSP1 | 15 ± 2 | 30 ± 4 | 48 ± 4 | 55 ± 10 |
| | fibronectin | 19 ± 2 | 48 ± 4 | 86 ± 6 | 78 ± 2 |
| | laminin | 5 ± 1 | 78 ± 3 | 151 ± 6 | 160 ± 3 |

Adhesion of SCLC cell lines (4 × 105 cells/well) was determined using substrates coated with TSP1, fibronectin, or laminin at the indicated concentrations. Adhesion was quantified microscopically and is presented as cells/mm2, mean ± S.D., n = 3.

Figure 17A:
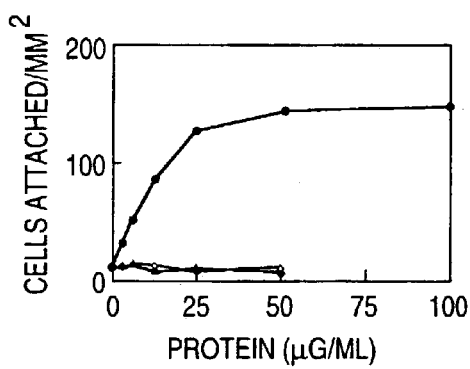
Figure 17B:
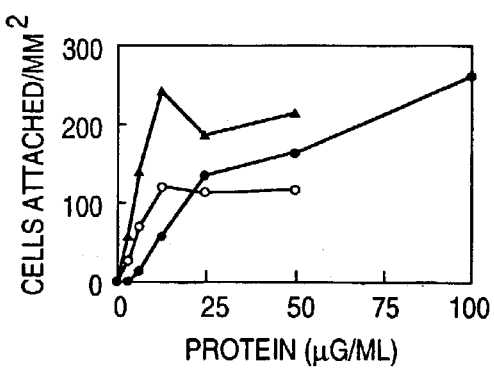
Figure 17C:
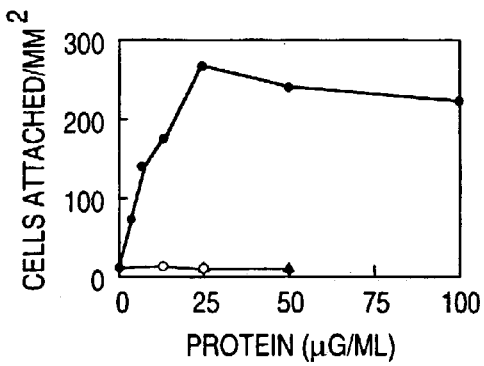
Figure 17D:
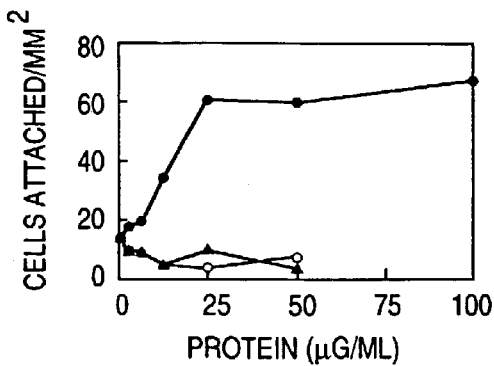

The cell lines OH-1 (FIG. 17A), H128 (FIG. 17C), and a variant of OH-1 (FIG. 17D) that lost the classic tight aggregate morphology (Goodwin, 1982) all attached avidly on TSP1 but failed to attach on murine laminin-1 or human plasma fibronectin. All three proteins were functional, because the human melanoma cell line A2058 attached at comparable levels on all three substrates (FIG. 17B). OH-1 SCLC cells also failed to attach on substrates coated with vitronectin, fibrinogen, type IV collagen, or gelatin (data not shown). Thus, the OH1 SCLC line lacks adhesion receptors for all matrix proteins tested except TSP1.

Several additional SCLC cell lines attached on TSP1 but also exhibited some adhesion to laminin or fibronectin (Table 4). All of the SCLC lines tested grew as aggregates in suspension with no adhesion to the substratum when cultured in serum-based media. H345 attached on TSP1 better than on laminin or fibronectin substrates. H169 cells, which originated from pleural fluid of patient with SCLC, had similar adhesion on the three extracellular matrix proteins, and N417 cells adhered preferentially on laminin.

Adhesion of SCLC on TSP1 is mediated by α3β1 integrin. Because TSP1 was the only extracellular matrix protein recognized by OH1 cells, we used this cell line to identify the specific TSP1 receptor expressed on SCLC cells. Several function-blocking antibodies that recognize known TSP1 receptors were examined. Antibodies against the TSP1 receptors, $\alpha_v\beta_3$ integrin (LM609) and CD36 (OKM5) had no effect on adhesion to TSP1 (results not shown). A function blocking antibody recognizing $\beta_1$ integrin was a dose-dependent inhibitor of OH1 cell adhesion on TSP1, but only inhibited adhesion by half at saturating concentrations (FIG. 18A and data not shown). Similar results were obtained using the β1 integrin ligand invasin (Krukonis et al., 1998) to inhibit adhesion on TSP1 (FIG. 18A). The residual integrin-independent adhesion of OH1 cells on TSP1 may be mediated by the heparin-binding sites of TSP1, because heparin also partially inhibited adhesion of OH1 cells on TSP1, and a combination of heparin with either the β1-blocking antibody or invasin completely inhibited adhesion (FIG. 18B).

Function-blocking integrin a subunit antibodies were used to define the specific β1 integrin that recognized TSP1 (FIG. 18B). An α3β1 integrin function-blocking antibody (P1B5) but not anti-$\alpha_4$ or anti-$\alpha_5$ integrin antibodies, which have been reported to recognize TSP1 in other cell types (Yabkowitz et al., 1993; Chandrasekaran et al., 1999), partially inhibited adhesion on TSP1. The α3 and β1 function-blocking antibodies also inhibited adhesion of OH1 cells on an immobilized TSP1 peptide that is recognized by the α3β1 integrin on breast carcinoma cells (Chandrasekaran et al., 1999), peptide 678, and on immobilized invasin (FIG. 18B). Invasin binds to several β1 integrins, including α3β1, α4β1, and α5β1 (Krukonis et al, 1998), so the failure of the α4β1 and α5β1 antibodies to significantly inhibit adhesion to immobilized invasin indicates that OH1 cells do not express functional α4β1 or α5β1 integrins.

The β1 integrin-activating antibody TS2/16 enhanced adhesion on TSP1 and TSP1 peptide 678 but not on a CD36-binding peptide (Mal II) or a heparin-binding peptide (p246) from TSP1 (FIG. 18C). This further confirmed that recognition of TSP1 peptide 678 by OH1 cells is β1 integrin-mediated and suggested that this integrin exists in a partially inactive state on OH1 cells.

TSP1 Modulates Endothelial Cell Proliferation Through α3β1 Integrin:

Interaction of the α3β1 integrin with its ligands can regulate epithelial cell proliferation (Gonzales et al., 1999). We therefore examined the effect of the α3β1 integrin-binding sequence from TSP1 on endothelial cell proliferation. Peptide 678 inhibited BAE cell proliferation in a dose-dependent manner when added in solution (FIG. 19A). Of two control peptides with amino acid substitutions that diminish integrin binding, (Krutzsch et al., 1999), 686 was inactive and 690 only inhibited proliferation of BAE cells by 19% at the highest dose tested (100 μM).

Previous publications have consistently reported that soluble TSP1 inhibits proliferation of endothelial cells (Bagavandoss et al., 1990; Taraboletti et al., 1990; Panetti et al., 1997; Sheibani et al., 1995). In contrast, TSP1 immobilized on the growth substrate stimulated dose-dependent proliferation of HUVE cells (FIG. 19B). Ligation of the α3β1 integrin was sufficient to stimulate this proliferative response, since immobilized α3β1 integrin antibody also stimulated proliferation (FIG. 19B). In this experiment, an α5β1 integrin antibody was used as a positive control, since ligation of this integrin is known to promote endothelial cell proliferation and survival. Stimulation of proliferation by immobilized TSP1 was α3β1-dependent, based on significant reversal of the growth stimulation in the presence of either the function blocking α3β1 antibody or TSP1 peptide 678 in solution (FIG. 19C). Specificity of the antibody inhibition was verified by its lack of a significant effect on endothelial cell proliferation stimulated by immobilized vitronectin (FIG. 19C). Consistent with the activity of the immobilized α3β1 antibody, plating of HUVE cells on immobilized TSP1 peptide 678 increased their proliferation (FIG. 19D). However, adding the same peptide in solution significantly inhibited HUVE cell proliferation (FIG. 19D).

Similar enhancement of microvascular (HDME) cell proliferation was observed after plating on immobilized TSP1 or TSP1 peptide 678 (FIG. 19E). As reported previously for several types of endothelial cells, however, soluble TSP1 inhibited proliferation of HDME cells stimulated by FGF2 (FIG. 19E). Therefore, even microvascular endothelial cells that express the anti-angiogenic TSP1 receptor CD36 (Dawson et al., 1997) can proliferate in response to TSP1 when it is immobilized.

Figure 20A:
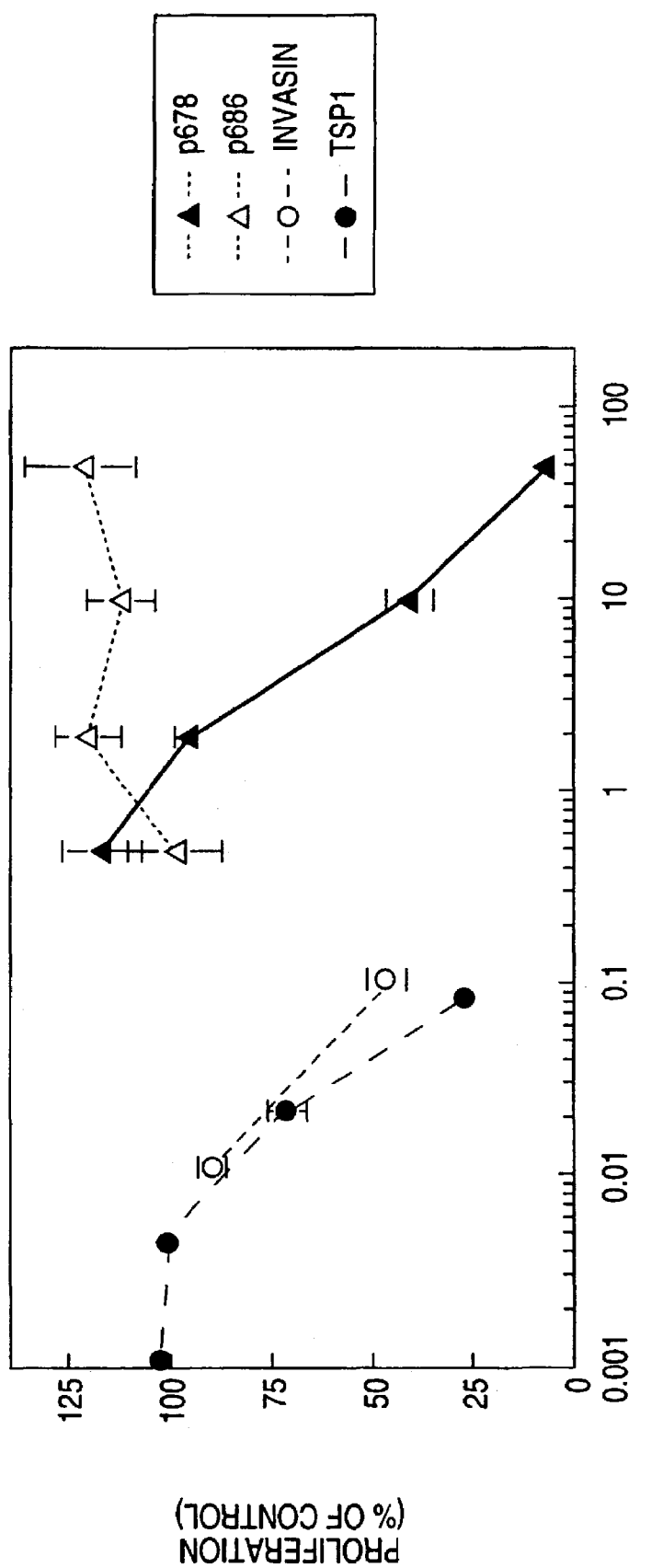
Figure 20B:
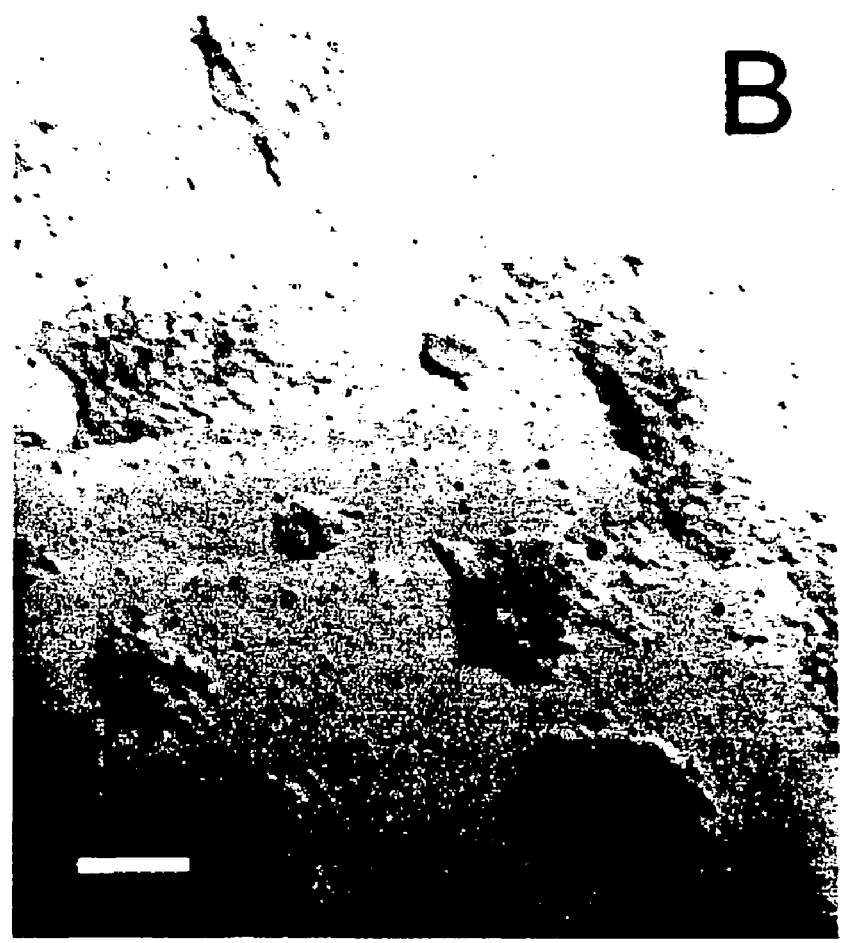
Figure 20C:
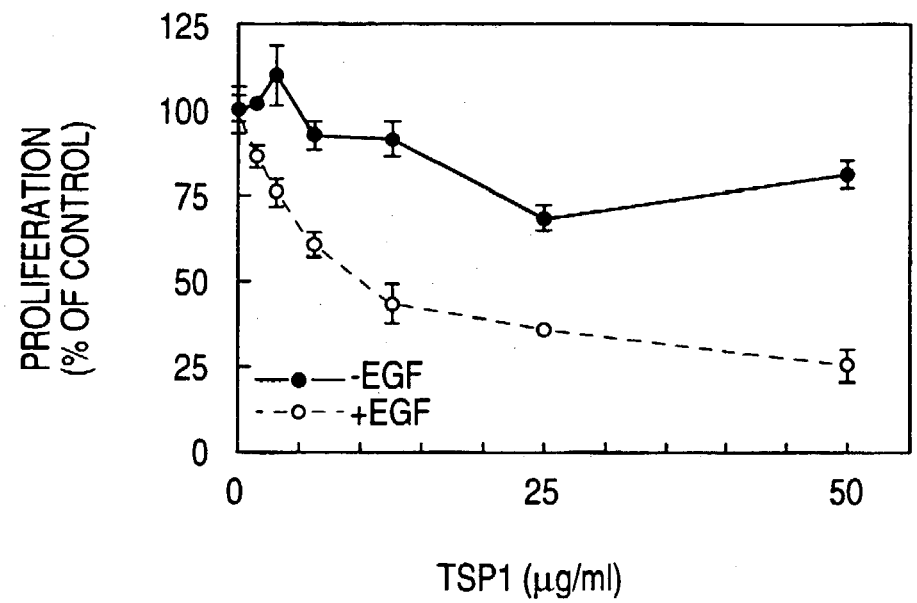
Figure 20D:
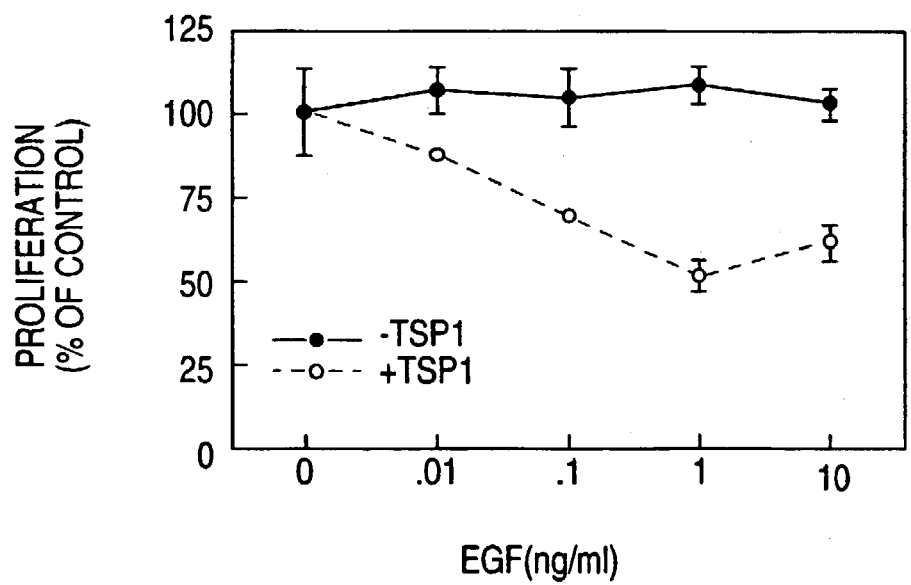
Figure 20E:
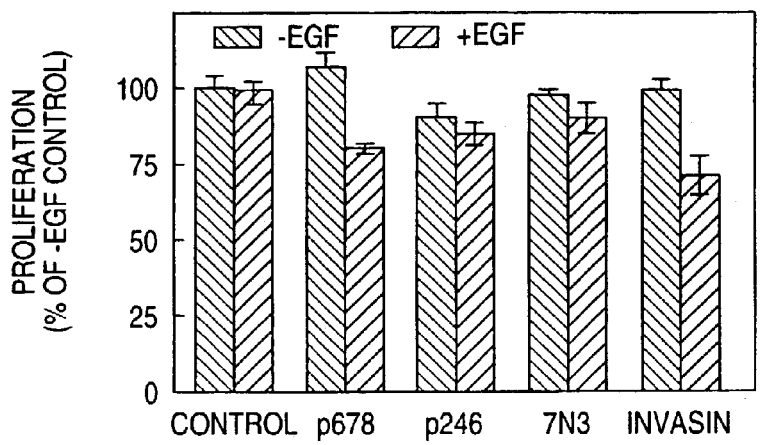

TSP1 and an α3β1 Integrin-Binding Peptide from TSP1 (Peptide 678) Inhibit SCLC Proliferation:

TSP1 is known to modulate growth of several cell types (reviewed in Roberts et al., 1996). Addition of soluble TSP1 to nonadherent OH-1 cells markedly inhibited their proliferation, with an $IC_{50}$ of 40 nM (FIG. 20A). This inhibition may result from ligation of the α3β1 integrin, because two additional ligands for this integrin, MBP-invasin ($IC_{50}$=80 nM) and the TSP1 peptide 678 ($IC_{50}$=6 μM), also inhibited OH1 cell proliferation (FIG. 20A). The activity of peptide 678 was specific in that the analog 686, in which the essential Asn residue was substituted by Ala was inactive. A heparin-binding peptide from the type 1 repeats only weakly inhibited OH1 cell proliferation at the same concentrations (data not shown), further indicating that inhibition by the integrin binding peptide from TSP1 is specific. When OH1 cells were plated on a TSP1 substrate, the attached SCLC cells continued to grow and formed extended flattened colonies on the TSP1 substrate (FIG. 20B). In the absence of TSP1, the cells remained as floating aggregates with no substrate adhesion. Adhesion of OH1 cells on a substrate coated with TSP1 only weakly inhibited proliferation of OH-1 cells in their growth medium (FIG. 20C). The effect of immobilized TSP1 on proliferation of OH1 cells in the presence of the growth facto EGF was also examined. Surprisingly, OH1 cell proliferation was much more sensitive to inhibition by immobilized TSP1 in the presence of EGF (FIG. 20C). Addition of EGF alone had no significant effect on proliferation of OH1 cells, but in the presence of TSP1 it produced a dose-dependent inhibition of proliferation (FIG. 20D). Inhibition of proliferation on a TSP1 substrate by EGF was specific in that IGF1 and bombazine did not display synergism with TSP1 to inhibit proliferation (data not shown). Inhibition of proliferation by a TSP1 substrate in the presence of EGF may also be mediated by the α3β1 integrin, because substrates coated with TSP1 peptide 678 or MBP-invasin showed similar cooperative effects with EGF to inhibit OH1 cell proliferation (FIG. 20E). TSP1 peptides that bind to CD47 (7N3) or heparin (p246) did not synergize with EGF, indicating that the activity of TSP1 peptide 678 is specific (FIG. 20E). Thus, EGF specifically and synergistically suppressed proliferation of SCLC cells attached on TSP1 or an α3β1-binding sequence from TSP1.

To examine the role of the α3β1 binding sequence of TSP1 in endothelial cell motility, the effect of peptide 678 and its D-reverse analog ri-FQGVLQNVRFVF (peptide 709) on endothelial scratch wound repair was determined (FIG. 21). Cells were arrested using 5-fluorouracil to measure effects on endothelial cell motility in the absence of proliferation. Peptide 678 was a dose-dependent inhibitor of BAE cell migration into the wound as was its D-reverse analog (peptide 709). These peptides were specific, in that the inactive control peptide 690 did not inhibit cell motility in this assay.

The β1 integrin recognition sequence in TSP1 may also contribute to angiogenesis, because peptide 678 (FQGVLQNVRFVF; SEQ ID NO:6) inhibited angiogenesis in the CAM assay (Table 5). The results of dose dependent inhibition of angiogenic response for various peptides (including peptide 678) are presented in Table 5.

TABLE 5

Angiogenetic response (% inhibition) of various peptides determined by chick chorioallantoic membrane (CAM) angiogenesis assay. Vitrogen gels containing peptides at the indicated concentrations were placed on CAMs in triplicate. Angiogenesis was assessed by injecting FITC-dextrans after 24 h and imaging the resulting vascular bed in the gels. Results are presented as percent inhibition relative to control gels without peptides, mean ± SD.

| Peptide | SEQ ID NO: | 5 μM | 10 μM | 20 μM |
|---|---|---|---|---|
| FQGVLQNVRFVF | 6 | 2 ± 5 | 17 ± 7 | 37 ± 9 |
| FQGVLQAVRFVF | 10 | 3 ± 4 | 4 ± 6 | 15 ± 7 |
| FQGVLQNVAFVF | 11 | 3 ± 3 | 5 ± 3 | 2 ± 5 |
| FAGVLQNVRFVF | 26 | 5 ± 2 | 9 ± 3 | 12 ± 4 |
| D-ri-FQGVLQNVRFVF | — | 5 ± 4 | 25 ± 13 | 39 ± 13 |

The results indicate that peptides with the consensus sequence (-NVRF-) inhibit vascularization in the chick CAM assay, whereas the peptide FQGVLQNVAFVF in which the Arg residue is substituted with Ala is inactive. The peptide FQGVLQAVRFVF has reduced activity due to substitution of the Asn residue in the required consensus. The D-reverse analog ri-FQGVLQNVRFVF also inhibits in the CAM assay and exhibits enhanced activity relative to the corresponding L-forward peptide, as expected due to its increased resistance to enzymatic degradation in vivo. This demonstrates that D-reverse analogs of the integrin antagonist peptides are functional in vivo and may have increased bioactivity due to their enhanced stability.

The dose dependence for inhibition was consistent with its reported IC50 for blocking of α3β1-dependent adhesion (Chandrasekaran et al., 1999). Inhibition of angiogenesis by peptide 678 is specific in that substitution of the essential Arg residue with Ala abolished inhibitory activity in the CAM assay.

In contrast to heparin binding peptides, which only inhibit angiogenesis stimulated by FGF2, Peptide 678 inhibited angiogenesis induced by either VEGF or FGF2. At 20 micromolar, peptide 678 inhibited angiogenesis stimulated by VEGF to 73±7% of control, inhibited angiogenesis stimulated by FGF2 to 68±5% of control, and inhibited angiogenesis stimulated by a mixture of both growth factors to 59±5% of control.

Although TSP1 is generally recognized as an inhibitor of angiogenesis (Good et al., 1990; Iruela-Arispe, 1999), conflicting reports about the effects of TSP1 on endothelial cell adhesion, motility, and proliferation have precluded a clear understanding of the mechanism for its anti-angiogenic activity (Good et al., 1990; Taraboletti et al., 1990; Iruela Arispe, 1991; Canfield et al., 1995; BenEzra et al., 1993; Nicosia et al., 1994). Recognizing that endothelial cells can modulate their expression or activation state of specific TSP1 receptors that transduce opposing signals may lead to a resolution of this conflict. It has now been demonstrated that sparse endothelial cells recognize an α3β1 integrin-binding sequence in TSP1 that stimulates endothelial cell spreading and proliferation when immobilized on a substratum. Addition of this TSP1 peptide in solution inhibits endothelial cell spreading on TSP1, proliferation, and migration in vitro and angiogenesis in vivo, presumably by inhibiting TSP1 interactions with this integrin. It has also now been demonstrated that the activity of this integrin to recognize TSP1 is suppressed in a confluent endothelial cell monolayer. Loss of endothelial cell—cell contact during wound repair in vitro or angiogenesis in vivo could therefore activate this receptor and make endothelial cells responsive to TSP1 signaling through the α3β1 integrin.

The activity of a second TSP1 receptor on endothelial cells that mediates inhibition of growth factor-stimulated migration, CD36, is regulated by differential expression in endothelial cells from large vessels versus capillaries (Swerlick et al., 1992; Dawson et al., 1997). Thus, CD36-negative endothelial cells with activated α3β1 integrin may recognize TSP1 primarily as an angiogenic signal, whereas CD36-positive endothelial cells with inactive α3β1 integrin would receive only an anti-angiogenic signal. Antagonism of FGF2-mediated angiogenic signals by heparin-binding sequences in TSP1 is a second pathway through which TSP1 can inhibit angiogenesis (Vogel et al., 1993; Iruela-Arispe et al., 1999). The responsiveness of this pathway has not been demonstrated to be regulated by endothelial cells. Therefore, endothelial cells receive both pro- and anti-angiogenic signals from TSP1, and the net balance of these signals is controlled by environmental signals that regulate the expression and activity of each TSP1 receptor.

TSP1 expression in endothelial cells is also regulated by cell—cell contact (Mumby et al., 1984; Canfield et al., 1990). Cells without mature cell—cell contacts produce more TSP1 than confluent cells (Mumby et al., 1984). Reports that TSP1 is involved in endothelial cell outgrowth in wound repair assays (Vischer et al., 1988; Munjal et al., 1990), combined with the data presented herein showing that the TSP1-binding integrin α3β1 is activated under the same conditions that stimulate TSP1 production, suggest that coordinate induction of TSP1 expression and activation of the TSP1 receptor α3β1 integrin are important for endothelial wound repair. This is consistent with the pattern of TSP1 expression induced in vascular injury (Reed et al., 1995). Although induction of TSP1 expression during angiogenic responses has been interpreted as a negative feedback pathway to limit angiogenesis (Suzuma et al., 1999), the possibility should be considered that TSP1 also participates as a positive regulator of neovasvcularization. This positive signal would be limited, because the α3β1 integrin becomes inactive when endothelial cell—cell contact is established.

Involvement of β1 integrins in endothelial cell adhesion on TSP1 is consistent with several recent studies of TSP1-endothelial interactions. Binding of soluble TSP1 to HUVEC was shown to be mediated mostly by heparin sulfate proteoglycans, with some involvement of αvβ3 integrin but not of CD36 (Gupta et al., 1999). However, combinations of these inhibitors could not completely inhibit TSP1 binding to HUVEC, suggesting that additional TSP1 receptors are present on endothelial cells. More relevant to the present studies, HDME cell adhesion on TSP1 was not RGD- or CD36-dependent, and was concluded to be mediated by an undefined TSP1 receptor (Chen et al., 1996). Based on the present data, the α3β1 integrin mediates this adhesive interaction of HDME cells with TSP1.

Several other matrix proteins are known to have both positive and negative effects on cell proliferation. Altering the architecture of fibronectin (Sechler et al., 1998) or type I collagen matrices (Koyama et al., 1996) can reverse their effects on cell cycle progression. Differential expression of integrins can reverse the effects of laminins and tenascin on cell proliferation (Yokosaki et al., 1996; Mainiero et al., 1997). TSP1 expresses both pro- and anti-proliferative activities toward other cell types, but its activity toward endothelial cells has been generally regarded as purely anti-angiogenic. However, it has been disclosed herein that interaction with immobilized intact TSP1 or the TSP1 peptide 678 through the endothelial α3β1 integrin stimulates proliferation of endothelial cells. Binding of laminin-5 to the α3β1 integrin was recently demonstrated to stimulate proliferation of mammary epithelial cells (Gonzales et al., 1999), suggesting that the growth promoting activity of TSP1 for endothelial cells may be a general response to α3β1 ligand binding. Since this peptide also inhibits endothelial cell motility in the absence of proliferation, α3β1 integrin interaction with intact TSP1 may stimulate both proliferation and motility. Defining the specific sequences in TSP1 and the respective endothelial cell receptors that are responsible for both its pro- and anti-angiogenic activities may allow one to isolate each activity and lead to development of peptides, gene therapy approaches, or small molecule analogs of TSP1 with more specific anti-angiogenic activities.

Each of the documents referred to above is incorporated herein in its entirely and for all purposes by reference. Except in the Examples, or where otherwise explicitly indicated, all numerical quantities in this description specifying amounts of materials, concentrations, number of amino acids in a peptide, and the like, are to be understood as modified by the word "about".

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

LIST OF REFERENCES

1. Adachi, M., et al., *J. Clin. Oncol.*, 16:1060–1067, (1998).
2. Adams, J. C., *J. Cell Sci.*, 108:1977–1990, (1995).
3. Akiyama, S. K., et al., *J. Biol. Chem.*, 260:4492–4500, (1985).
4. Akiyama, S. K., et al., *J Biol. Chem.*, 260:4492–5000, (1985).
5. Almquist, R. G. et al., *J. Med. Chem.*, 23:1392–1398, (1980).
6. Aota, S., et al., *Adv. Enzymol. Relat. Areas Mol. Biol.*, 70:1–21, (1995).
7. Atherton, et al., *Solid Phase Peptide Synthesis: A Practical Approach*, IRL Press (1989).
8. Bagavandoss, P., et al., *Biochem Biophys Res Commun.*, 170:867–72, (1990).
9. Beckmann, G., et al., *J. Mol. Biol.*, 275:725–730, (1998).
10. BenEzra, D., et al., *Invest Ophthalmol Vis Sci.*, 34:3601–8, (1993).
11. *Bioreversible Carriers in Drug Design. Theory and Application*, Roche (ed.), Pergamon Press, (1987).
12. Bornstein, P., "Thrombospondins: structure and regulation of expression,"*FASEB J.* 6:3290–3299, (1992).
13. Bornstein, P., "Diversity of function is inherent in matricellular proteins: an appraisal of thrombospondin 1," *J. Cell Biol.*, 130:503–506, (1995).
14. Brooks, P. C., et al., *Science*, 264:569–71, (1994).
15. Brooks, P. C., et al., *J Clin Invest.*, 96:1815–22, (1995).
16. Brunswick, et al., "Picogram quantities of anti-Ig antibodies coupled to dextran induce B cell proliferation," *J. Immunol.*, 140:3364–3372, (1988).
17. Canfield, A. E., et al., *Biochem J.*, 268:225–30, (1990).
18. Canfield, A. E., et al., *J Cell Sci.*, 108:797–809, (1995).
19. Chandrasekaran, S., et al., *J. Biol. Chem.*, 274:11408–11416, (1999).
20. Chen, Z. S., et al., *J Invest Dermatol.*, 106:215–20, (1996).
21. Chorev, M., et al., *Acc. Chem. Res.*, 26:266–273, (1993).
22. Clezardin, P., et al., *Biochem. J.*, 321:819–827, (1997).
23. Crawford, S. E., et al., *Cell*, 93:1159–1170, (1998).
24. Dameron, K. M., et al., *Science*, 265:1582–4, (1994).
25. Dawson, D. W., et al., *J. Cell Biol.*, 138:707–717, (1997).
26. DeFreitas, M. F., et al., *Neuron*, 15:333–343, (1995).
27. Delwel, G. O., et al., *Mol. Biol. Cell*, 5:203–215, (1994).
28. Eble, J. A., et al., *Biochemistry*, 37:10945–10955, (1998).
29. Elices, M. J., et al., *J. Cell Biol.*, 112:169–181, (1991).
30. Emsley, J., et al., *Nature*, 367:338–345, (1994).
31. Evans et al., *J. Med. Chem*, 30:1229, (1987).
32. Fauchere, J., *Adv. Drug Res.*, 15:29, (1986).
33. Fenczik, C. A., et al., *Nature*, 390:81–5, (1997).
34. Fernandez, C., et al., *Frontiers Biosci.*, 3:684–700, (1998).
35. Folkman, J., "Angiogenesis in cancer, vascular, rheumatoid and other disease," *Nat Med.*, 1:27–31, (1995).
36. Gao, A. G., et al., *J. Biol. Chem.*, 271:21–24, (1996).
37. Gao, A. G., et al., *J. Cell Biol.*, 135:533–44, (1996).
38. Gehlsen, K. R., et al., *J. Cell Biol.*, 117:449–459, (1992).
39. Gilman et al. (eds), *Goodman and Gilman's: The Pharmacological Bases of Therapeutics*, 8th Ed., Pergamon Press (1990).
40. Godyna, S., et al., *J. Cell Biol.*, 129:1403–10, (1995).
41. Gonzales, M., et al., *Mol. Biol. Cell*,. 10:259–270, (1999).
42. Good, D. J., et al., *Proc Natl Acad Sci USA.*, 87:6624–8, (1990).
43. Goodman, M., et al., *Acc. Chem. Res.*, 12:1–7, (1979).

44. Greisler, H. P., *New Biologic and Synthetic Vascular Prostheses*, R. G. Landes, Co., Austin, Tex. (1991).
45. Gresham, H. D., et al., *J. Biol. Chem.*, 271:30587–30594, (1996).
46. Guo, N. H., et al., *Proc. Natl. Acad. Sci. U.S.A.*, 89:3040–3044, (1992).
47. Guo, N. H., et al., *J. Biol. Chem.*, 267:19349–19355, (1992).
48. Guo, N. H., et al., *J. Peptide Res.*, 50:210–221, (1997).
49. Guo, N., et al., *Cancer Res.*, 57:1735–42, (1997).
50. Guo, N., et al., *Cancer Res.*, 58:3154–3162(1998).
51. Gupta, K., et al., *Biochim Biophys Acta.*, 1453:63–73 (1999).
52. Hann, M. M., *J. Chem. Soc. Perkin Trans. I*, pgs. 307–314, (1982).
53. Hanahan, D., et al., "Patterns and emerging mechanisms of the angiogenic switch during tumorigenesis," *Cell*, 86:353–364, (1996).
54. Hemler, M. E., et al., *Cell Differ. Dev.*, 32:229–238, (1990).
55. Hemler, M. E., et al., *J. Immunol.*, 132:3011–3018, (1984).
56. Holladay, M. W. et al., *Tetrahedron Lett.*, 24:4401–4404, (1983).
57. Hruby, V. J., *Life Sci.*, 31:189–199, (1982).
58. Hsu, S. C., et al., *Cancer Res.* 56:5684–91, (1996).
59. Hudson, D. et al., *Int. J. Pept. Prot. Res.*, 14:177–185, (1979).
60. Inman, J. K. "Thymus-independent antigens: The preparation of covalent, hapten-FICOLL conjugates," *J. Immunol.*, 114:704–709, (1975).
61. Iruela Arispe, et al., *Proc Natl Acad Sci USA*, 88:5026–30, (1991).
62. Iruela-Arispe, et al., *Circulation. in press*, (1999).
63. Jennings-White, C. et al., *Tetrahedron Lett.*, 23:2533, (1982).
64. Joyce, N. C., et al., *Invest. Ophthalmol. Vis. Sci.*, 30:1548–1559, (1989).
65. Keenan, R. M., et al., *J Med. Chem.*, 40:2289–92, (1997).
66. Koyama, H., et al., *Cell.*, 87:1069–1078, (1996).
67. Kreidberg, J. A., et al., *Development*, 122:3537–3547, (1996).
68. Krukonis, E. S., et al., *J. Biol. Chem.*, 273:31837–31843, (1998).
69. Krutzsch, H. C., et al., *J. Biol. Chem.*, 274:24080–24086, (1999).
70. Lahav, J., *Exp Cell Res.* 177:199–204, (1988).
71. Lawler, J., R., et al., *J. Cell Biol.*, 107:2351–61, (1988).
72. Lawrence, C. E., et al., *Science*, 262:208–214, (1993).
73. Legrand, C., et al., *Blood*, 79:1995–2003, (1992).
74. Mainiero, F., et al., *Embo J.*, 16:2365–75, (1997).
75. MERCK INDEX, Merck & Co., Rahway, N.J.
76. Merrifield, *J. Amer. Chem. Soc.*, 85:2149–2456, (1963).
77. Merrifield, *Science*, 232:341–347, (1986).
78. Miles, A. J., et al., *J. Biol. Chem.*, 270:29047–29050, (1995).
79. Mongini, P. K. A. et al., *J. Immunol.*, 148:3892–3901, (1992).
80. Morandi, V., F., et al., *In Vitro Cell Dev Biol Anim.*, 29A:585–91, (1993).
81. Morelli, D., et al., *Clin Cancer Res.*, 4:1221–5, (1998).
82. Morley, J. S., *Trends Pharm. Sci.*, pp. 463–468, (1980).
83. Mumby, S. M., et al., *J. Cell. Physiol.*, 120:280–288 (1984).
84. Munjal, I. D., et al., *Eur J. Cell Biol.*, 52:252–63, (1990).
85. Murphy-Ullrich, J. E., et al., *J. Biol. Chem.*, 268: 26784–26789, (1993).
86. Murphy-Ullrich, J. E., et al., *J. Cell Biol.*, 109:1309–19, (1989).
87. Nicosia, R. F., et al., *J. Cell Biol.*, 124:183–93, (1994).
88. Norris (ed.), *Novel Drug Delivery Systems*, 2nd Ed., Marcel Dekker Inc. (1989).
89. Panetti, T. S., et al., *J Lab Clin Med.*, 129:208–16, (1997).
90. Passaniti, A., et al., *Lab Invest.*, 67:519–28, (1992).
91. Polyerini, P. J., "The pathophysiology of angiogenesis," *Crit. Rev. Oral Biol. Med.*, 6:230–247, (1995).
92. Prater, C. A., et al., *J. Cell Biol.*, 112:1031–1040, (1991).
93. Reed, M. J., et al., *American Journal of Pathology.*, 147:1068–1080, (1995).
94. Remington's Pharmaceutical Sciences
95. Roberts, A. B., et al., *Proc Natl Acad Sci USA.*, 83:4167–4171, (1986).
96. Roberts, D. D., "Regulation of tumor growth and metastasis by thrombospondin-1," *FASEB J.*, 10:1183–1191, (1996).
97. Roberts, D. D., et al., *J. Tissue Cult Methods*, 16:217–222, (1994).
98. Ruoslahti, E., *Ann. Rev. Cell Dev. Biol.*, 12:697–715, (1996).
99. Sambrook et al., *Molecular Cloning: A Laboratory Manual* $2^{nd}$ ed., Volumes 1–3, Cold Spring Harbor Laboratory, (1989).
100. Schuler, G. D., et al., *Prot. Struct. Funct. Genet.*, 9:180–190, (1991).
101. Schultz-Cherry, S., et al., *J. Cell Biol.*, 122:923–32, (1993).
102. Sechler, J. L., et al., *J. Biol. Chem.*, 273:25533–25536 (1998).
103. Sheibani, N., et al., *Proc Natl Acad Sci USA.*, 92:6788–92, (1995).
104. Shrive, A. K., et al., *Nature Struct. Biol.*, 3:346–353, (1996).
105. Sipes, J. M., et al., Cooperation between thrombospondin-1 type 1 repeat peptides and integrin $\alpha v\beta 3$ ligands to promote melanoma cell spreading and focal adhesion formation. *J. Biol. Chem. in press*, (1999).
106. Spatola, A. F., "Chemistry and Biochemistry of Amino Acids, Peptides, and Proteins," B. Weinstein, eds., Marcel Dekker, New York, p. 267 (1983).
107. Spatola, A. F., "Peptide Backbone Modifications," *Vega Data*, vol. 1 no. 3 (March 1983).
108. Spatola, A. F. et al., *Life Sci.*, 38:1243–1249, (1986).
109. Stahl, S., et al., *J. Cell Sci.*, 110:55–63, (1997).
110. Suzuma, K., et al., *Am J Pathol.* 154:343–54, (1999).
111. Swerlick, R. A., et al., *J. Immunol.*, 148:78–83, (1992).
112. Szelke, M. et al., European Appln. EP 45665 (1982) CA: 97:39405 (1982).
113. Taraboletti, G., et al., *J. Cell Biol.*, 111:765–72, (1990).
114. Tolsma, S. S., et al., *Microvasc Res,.* 54:13–26, (1997).
115. Tolsma, S. S., et al., *J. Cell Biol.*, 122:497–511, (1993).
116. Veber et al., *TINS*, p. 392 (1985).
117. Vischer, P., et al., *Eur J. Cell Biol.*, 73:332–43, (1997).
118. Vischer, P., et al., *Eur J. Cell Biol.* 47:36–46, (1988).
119. Vogel, T., et al., *J. Cell Biochem.*, 53:74–84, (1993).
120. Volpert, O. V., et al., *Proc Natl Acad Sci USA.*, 95:6343–8, (1998).
121. Volpert, O. V., et al., *Biochem Biophys Res Commun.*, 217:326–332, (1995).
122. Weinstat-Saslow, D. L., *Cancer Res.*, 54:6504–11, (1994).

123. Weitzman, J. B., et al., *Cell Adhes. Commun.*, 4:41–52, (1996).
124. Weitzman, J. B., et al., *J. Biol. Chem.*, 268:8651–8657, (1993).
125. Wu, C., et al., *J. Cell Sci.*, 108:2511–2523, (1995).
126. Yabkowitz, R., et al., *J. Immunol.*, 151:149–58, (1993).
127. Yamada, K. M., *J. Biol. Chem.*, 266:12809–12812, (1991).
128. Yanez-Mo, M., et al., *J. Cell Biol.*, 141:791–804, (1998).
129. Yokosaki, Y., et al., *J. Biol. Chem.*, 271:24144–24150, (1996).

What is claimed is:

1. A peptide that binds α3β1 integrin, wherein said peptide consists of a sequence selected from the group consisting of FQGVLQQVRFVF (SEQ ID NO:20), FQGVLQSVRFVF (SEQ ID NO:21), acQGVLQNVRF (SEQ ID NO:22), FQGVLNNVRFVF (SEQ ID NO:24), AQGVLQNVRFVF (SEQ ID NO:25), FAGVLQNVRFVF (SEQ ID NO:26), FQGVAQNVRFVF (SEQ ID NO:27), FQGVLQNVRFVA (SEQ ID NO:28), FQGVLANVRFVF (SEQ ID NO:29), FQGVLQNVRFV (SEQ ID NO:30), QGVLQNVRFVF (SEQ ID NO:31), and FQGVLQNVRF (SEQ ID NO:32).

2. A peptide consisting of the sequence $R_1$-$X_1$-$X_2$-$X_3$-$X_4$-$R_2$ or full retro-inverso sequences thereof, wherein $X_1$ is selected from the group consisting of N and Q; $X_2$ is V; $X_3$ is R; and $X_4$ is F; $R_1$ is a hydrogen or from 1 to 6 amino acids, an acyl or an aryl group; and $R_2$ is from 1 to 3 amino acids, a hydroxide or an amide, provided that the peptide binds α3β1 integrin, and wherein the $X_1$-$X_2$-$X_3$-$X_4$ portion of the sequence is NVRF (SEQ ID NO:51) or QVRF (SEQ ID NO:53).

3. A peptide consisting of the sequence FQGVLQNVRFVF (SEQ ID NO:6) wherein every amino acid in said sequence is a D-amino acid.

4. A composition comprising a peptide according to claim 2 and a pharmaceutically acceptable carrier.

5. A composition comprising a peptide according to claim 2 in a sterile aqueous solution.

6. A peptide consisting of the sequence $R_1$-$X_1$-$X_2$-$X_3$-$X_4$-$R_2$ or full retro-inverso sequences thereof, wherein $X_1$ is D; $X_2$ is V; $X_3$ is R; and $X_4$ is F; $R_1$ is a hydrogen or from 1 to 6 amino acids, an acyl or an aryl group; and $R_2$ is 2 or 3 amino acids, a hydroxide or an amide, provided that the peptide binds α3β1 integrin.

7. The peptide according to claim 6 consisting of the sequence FQGVLQDVRFVF (SEQ ID NO:19).

8. The peptide of claim 6, wherein the peptide contains the sequence DVRF (SEQ ID NO:54) and is up to 12 amino acids in length.

9. The peptide of claim 6 wherein $R_1$ is a peptide consisting of the sequence selected from the group consisting of FQGVLQ (SEQ ID NO:13), FAGVLQ (SEQ ID NO:14), FQGVAQ (SEQ ID NO:15), FQGVLA (SEQ ID NO:16), and FQGVLN (SEQ ID NO:17).

10. A peptide consisting of the sequence $R_1$-$X_1$-$X_2$-$X_3$-$X_4$-$R_2$ or full retro-inverso sequences thereof, wherein $X_1$ is D; $X_2$ is V; $X_3$ is R; and $X_4$ is F; $R_1$ is a hydrogen or from 1 to 6 amino acids, an acyl or an aryl group; and $R_2$ is 2 or 3 amino acids, a hydroxide or an amide provided that the peptide binds α3β1 integrin, wherein at least one amino acid is a D-amino acid.

11. A composition comprising a peptide according to claim 6 and a pharmaceutically acceptable carrier.

12. A composition comprising a peptide according to claim 6 in a sterile aqueous solution.

13. A retro-inverso synthetic peptide consisting of the amino acid sequence, from C-terminal (left) to N-terminal (right): ri- $R'_1$-D-V-R-F-$R'_2$, wherein ri denotes a retro-inverso peptide sequence and all amino acids are D amino acids and D-V-R-F is SEQ ID NO:54; $R'_1$ is a hydrogen or from 1 to 6 amino acids, a hydroxide or an amide; and $R'_2$ is 2 or 3 amino acids, a hydroxide or an amide, provided that the peptide binds α3β1 integrin.

14. The peptide of claim 13, wherein the peptide contains the sequence DVRF (SEQ ID NO:54) and is up to 12 amino acids in length.

15. An in vitro method of inhibiting adhesion of a cell expressing α3β1 integrin to an extracellular matrix comprising contacting said cell with a peptide according to claim 2.

16. The method of claim 15 wherein the extracellular matrix comprises TSP1 or laminins.

17. The method of claim 15 wherein said cell comprises an epithelial or an endothelial cell.

18. The method of claim 15 wherein said cell is a tumor cell.

19. The method of claim 15 wherein said cell is a breast carcinoma cell or a small cell lung carcinoma.

20. An in vitro method of inhibiting α3β1 integrin-mediated cell motility, comprising contacting a cell with a peptide according to claim 2.

21. The method of claim 20 wherein the cell is an epithelial cell, an endothelial cell or a malignant cell.

22. An in vitro method of inhibiting proliferation of endothelial cells, comprising contacting said cells with a peptide according to claim 2.

23. An in vitro method of inhibiting proliferation of small cell lung carcinoma cells, comprising contacting said cells with a peptide according to claim 2.

* * * * *